US009062059B2

(12) United States Patent
Cox et al.

(10) Patent No.: US 9,062,059 B2
(45) Date of Patent: Jun. 23, 2015

(54) PYRIMIDINE PDE10 INHIBITORS

(75) Inventors: Christopher D. Cox, Harleysville, PA (US); Vadim Y. Dudkin, Lansdale, PA (US); Jeffrey Kern, Gilbertsville, PA (US); Mark E. Layton, Harleysville, PA (US); Izzat T. Raheem, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/239,603

(22) PCT Filed: Aug. 20, 2012

(86) PCT No.: PCT/US2012/051522
§ 371 (c)(1),
(2), (4) Date: Feb. 19, 2014

(87) PCT Pub. No.: WO2013/028590
PCT Pub. Date: Feb. 28, 2013

(65) Prior Publication Data
US 2014/0228368 A1 Aug. 14, 2014

Related U.S. Application Data

(60) Provisional application No. 61/527,392, filed on Aug. 25, 2011.

(51) Int. Cl.
C07D 487/04 (2006.01)
C07D 239/47 (2006.01)
C07D 401/14 (2006.01)
C07D 417/14 (2006.01)
A61K 31/506 (2006.01)

(52) U.S. Cl.
CPC .............. *C07D 487/04* (2013.01); *A61K 31/506* (2013.01); *C07D 239/47* (2013.01); *C07D 401/14* (2013.01); *C07D 417/14* (2013.01)

(58) Field of Classification Search
CPC .. A61K 31/506; C07D 401/14; C07D 403/14; C07D 417/14; C07D 413/14; C07D 487/04
USPC ........................... 514/256; 544/295, 296, 328
See application file for complete search history.

(56) References Cited

U.S. PATENT DOCUMENTS

| 8,785,467 B2 * | 7/2014 | Cox et al. ...................... 514/274 |
| 2008/0167297 A1 | 7/2008 | Thomas et al. |
| 2011/0166135 A1 | 7/2011 | Morimoto et al. |
| 2011/0230472 A1 | 9/2011 | Mitsuoka et al. |

FOREIGN PATENT DOCUMENTS

| CN | 101184752 | 5/2008 |
| WO | WO2005120514 | 12/2005 |
| WO | WO2006044372 | 4/2006 |
| WO | WO2006072828 | 7/2006 |
| WO | WO2007129183 | 11/2007 |
| WO | WO2010/030027 | 3/2010 |
| WO | WO2010027097 | 3/2010 |
| WO | WO2011/008931 | 1/2011 |
| WO | WO2011008931 | 1/2011 |
| WO | WO2011/089132 | 7/2011 |
| WO | WO2012044561 | 4/2012 |
| WO | WO2012044562 | 4/2012 |
| WO | WO 2012044561 A2 * | 5/2012 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
Becker et al., Phosphodiesterase Inhibitors—Are They Potential Neuroleptic Drugs?, Behavioural Brain research, 2008, pp. 155-160, 186.
Fujishige et al., Cloning and Characterization of a Novel Human Phosphodiesterase That Hydrolyzes Both cAMP and cGMP (PDE10A), J. of Biological Chemistry, Jun. 25, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Mosser et al., Automation of In Vitro Dose-Inhibition Assays Utlizing the Tecan Genesis and an Integratd Software Package to Support the Drug Discovery Process, JALA, 2003, pp. 54-63, 8, Sage Publications.
Schmidt et al., Pre-clincal Characterization of Selective Phosphodiesterease 10A Inhibitors: A New Therapeutic Approach to the Treatment of Schizophrenia, J. of Pharmacology and Experimental Therapeutics, 2008, pp. 690-690, 325.
Siuciak et al., Inhibiton of the Striatum-Enriched Phosphodiesterease PDE10A: A novel Approach to the Treatment of Psychosis, Neuropharmacology, 2006, pp. 386-396, 51.
Soderling et al., Isolation and Characterization of a Dual-Substrate Phosphodiesterase Gene Family: PDE10A, Proc. Natl. Acad. Sci. USA, Jun. 1999, pp. 7071-7076, 96.
Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.
China Patent Agent (H.K.) Ltd letter dated Jan. 30, 2015; 4 pages.

* cited by examiner

*Primary Examiner* — Alexander R Pagano
(74) *Attorney, Agent, or Firm* — Sylvia A. Ayler; John C. Todaro

(57) ABSTRACT

The present invention is directed to pyrimidine compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

37 Claims, No Drawings

PYRIMIDINE PDE10 INHIBITORS

CROSS REFERENCE TO RELATED APPLICATIONS

This application is the National Stage of International Application No. PCT/US2012/051522 filed on Aug. 20, 2012, which claims the benefit under 35 U.S.C. 119(e) of U.S. Provisional Application No. 61/527,392, filed Aug. 25, 2011.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olarizapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS, USA* (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to pyrimidine compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

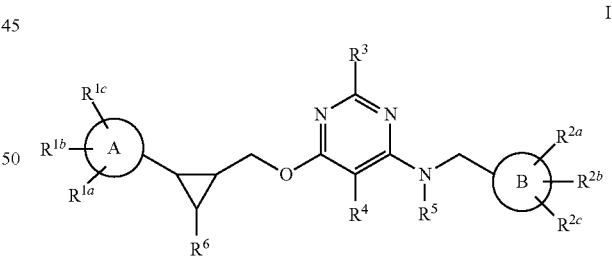

wherein:
A is selected from the group consisting of:
  (1) pyridyl,
  (2) quinolinyl,
  (3) naphthyridinyl,
  (4) thiazolyl,
  (5) pyridazinyl,
  (6) oxazolyl, and
  (7) pyrazolyl,
  (8) dihydropyrrolopyrazolyl,
  (9) dihydrocyclopentapyridinyl,
  (10) imidazopyridazinyl, and
  (11) pyrazolopyrimidinyl;

B is selected from the group consisting of:
(1) thiazolyl,
(2) pyrazolyl,
(3) thiadiazolyl,
(4) isoxazolyl,
(5) isothiazolyl,
(6) pyridyl, and
(7) pyrimidinyl;

$R^{1a}$, $R^{1b}$ and $R^{1c}$ are independently selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-naphthyl, where the phenyl or naphthyl is unsubstituted or substituted with one or more substituents selected from $R^{13}$,
(9) —(C=O)$_m$—O$_n$-heteroaryl, where the heteraryl is unsubstituted or substituted with one or more substituents selected from $R^{13}$,
(10) —(C=O)$_m$—NR$^{10}$R$^{11}$,
(11) —S(O)$_2$—NR$^{10}$R$^{11}$,
(12) —S(O)$_q$—R$^{12}$, where q is 0, 1 or 2 and where $R^{12}$ is selected from the definitions of $R^{10}$ and $R^{11}$,
(13) —CO$_2$H,
(14) —CN, and
(15) —NO$_2$;

$R^{2a}$, $R^{2b}$ and $R^{2c}$ are independently selected from the group consisting of:
(1) hydrogen,
(2) halogen,
(3) hydroxyl,
(4) —(C=O)$_m$—O$_n$—C$_{1-6}$alkyl, where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-naphthyl, where the phenyl or naphthyl is unsubstituted or substituted with one or more substituents selected from $R^{13}$,
(9) —(C=O)$_m$—O$_n$-heterocyclyl, where the heterocyclyl is unsubstituted or substituted with one or more substituents selected from $R^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^3$ is selected from the group consisting of:
(1) CH$_3$,
(2) CF$_3$,
(3) CH$_2$F,
(4) CH$_2$CH$_3$,
(5) cyclopropyl,
(6) cyano,
(7) hydrogen,
(8) NH$_2$,
(9) C(O)OR$^5$,
(10) —O—C$_{1-6}$alkyl,
(11) —(CO)NH$_2$,
(12) C$_{1-6}$alkylOH,
(13) C(O)C$_{1-6}$alky, and
(14) halogen;

$R^4$ is selected from the group consisting of:
(1) hydrogen,
(2) halo,
(3) —C$_{1-6}$alkyl, and
(4) cyano, $R^5$ is selected from the group consisting of:
(1) hydrogen, and
(2) C$_{1-6}$alkyl;

$R^6$ is selected from the group consisting of:
(1) hydrogen,
(2) C$_{1-6}$alkyl, and
(3) OC$_{1-6}$alkyl;

$R^{10}$ and $R^{11}$ are independently selected from the group consisting of:
(a) hydrogen,
(b) C$_{1-6}$alkyl, which is unsubstituted or substituted with $R^{14}$,
(c) C$_{3-6}$alkenyl, which is unsubstituted or substituted with $R^{14}$,
(d) C$_{3-6}$alkynyl, which is unsubstituted or substituted with $R^{14}$,
(e) C$_{3-6}$cycloalkyl which is unsubstituted or substituted with $R^{14}$,
(f) C$_{1-6}$alkoxyl, which is unsubstituted or substituted with $R^{14}$,
(g) phenyl, which is unsubstituted or substituted with $R^{14}$, and
(h) heteroaryl, which is unsubstituted or substituted with $R^{14}$, $R^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from $R^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from $R^{14}$,
(6) —(C=O)$_m$—C$_{2-4}$alkenyl, where the alkenyl is unsubstituted or substituted with one or more substituents selected from $R^{14}$,
(7) —(C=O)$_m$—C$_{2-4}$alkynyl, where the alkynyl is unsubstituted or substituted with one or more substituents selected from $R^{14}$,
(8) —(C=O)$_m$—O$_n$-phenyl or —(C=O)$_m$—O$_n$-naphthyl, where the phenyl or naphthyl is unsubstituted or substituted with one or more substituents selected from $R^{14}$, (9) —(C=O)$_m$—O$_n$-heteroaryl, where the heteroaryl is unsubstituted or substituted with one or more substituents selected from R$^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heteroaryl,
(10) —CO$_2$H, and
(11) —CN;

or a pharmaceutically acceptable salt thereof.

An embodiment of the present invention includes compounds of the formula Ia:

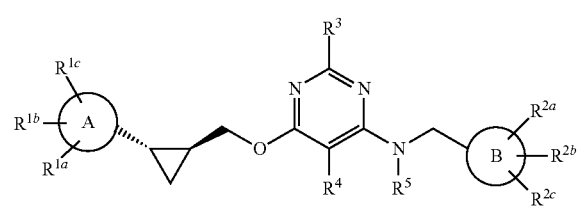

Ia wherein A, B, R$^{1a}$, R$^{1b}$, R$^{1c}$, R$^{2a}$, R$^{2b}$, R$^{2c}$, R$^3$, R$^4$, and R$^5$ are defined herein; or a pharmaceutically acceptable salt thereof.

An embodiment of the present invention includes compounds of the formula Ib:

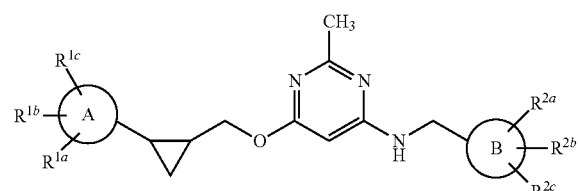

Ib wherein A, B, R$^{1a}$, R$^{1b}$, R$^{1c}$, R$^{2a}$, R$^{2b}$, and R$^{2c}$ are defined herein; or a pharmaceutically acceptable salt thereof.

An embodiment of the present invention includes compounds wherein A is selected from the group consisting of:
(1) pyridyl,
(2) quinolinyl,
(3) naphthyridinyl,
(4) thiazolyl,
(5) pyridazinyl,
(6) oxazolyl, and
(7) pyrazolyl.

An embodiment of the present invention includes compounds wherein A is selected from the group consisting of:
(1) pyridyl,
(2) quinolinyl, and
(3) naphthyridinyl.

An embodiment of the present invention includes compounds wherein A is selected from the group consisting of:

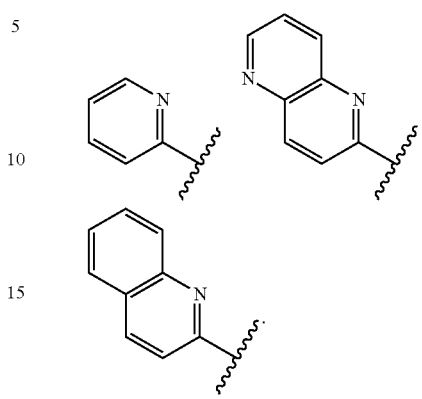

An embodiment of the present invention includes compounds wherein A is pyridyl. An embodiment of the present invention includes compounds wherein A is quinolinyl. An embodiment of the present invention includes compounds wherein A is naphthyridinyl.

An embodiment of the present invention includes compounds wherein the cyclopropyl group which connects the group A to the —CH$_2$O— group is substituted in an (S,S) stereochemical orientation.

An embodiment of the present invention includes compounds of the formula Ic:

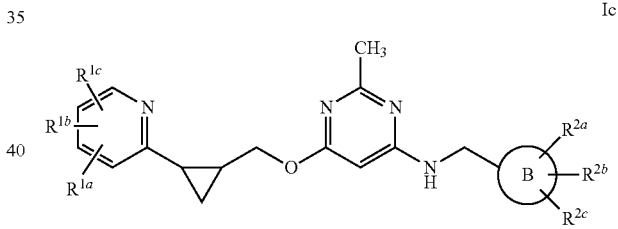

Ic wherein B, R$^{1a}$, R$^{1b}$, R$^{1c}$, R$^{2a}$, R$^{2b}$, and R$^{2c}$ are defined herein; or a pharmaceutically acceptable salt thereof.

An embodiment of the present invention includes compounds wherein B is selected from the group consisting of:
(1) thiazolyl,
(2) pyrazolyl, and
(3) thiadiazolyl.

An embodiment of the present invention includes compounds wherein B is thiazolyl. An embodiment of the present invention includes compounds wherein B is pyrazolyl. An embodiment of the present invention includes compounds wherein B is thiadiazolyl.

An embodiment of the present invention includes compounds wherein B is selected from the group consisting of:

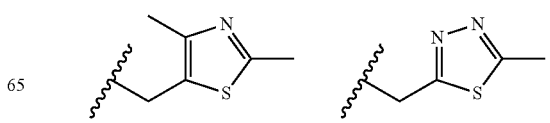

-continued

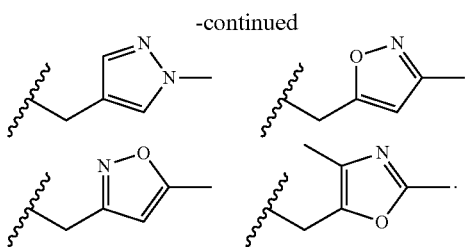

An embodiment of the present invention includes compounds wherein B is selected from the group consisting of:

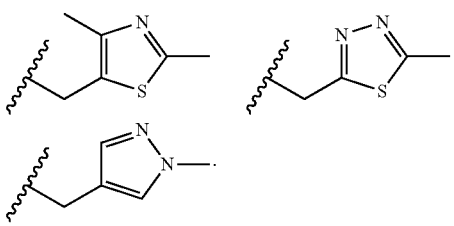

An embodiment of the present invention includes compounds wherein B is:

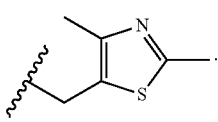 [SMILES: *Cc1sc(C)nc1C]

An embodiment of the present invention includes compounds wherein B is:

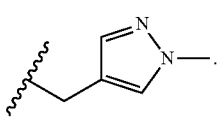 [SMILES: *Cc1cnn(C)c1]

An embodiment of the present invention includes compounds wherein B is:

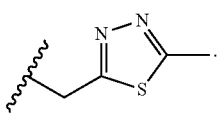 [SMILES: *Cc1nnc(C)s1]

An embodiment of the present invention includes compounds wherein $R^{1a}$, $R^{1b}$, $R^{1c}$ are selected from the group consisting of:
  (1) $C_{1-6}$alkyl, which is unsubstituted or substituted with halogen or hydroxyl,
  (2) —O—$C_{1-6}$alkyl, which is unsubstituted or substituted with halogen or hydroxyl,
  (3) phenyl, which is unsubstituted or substituted with halogen, hydroxyl, —$NH_2$, —NH—$C_{1-6}$alkyl, or —N($C_{1-6}$alkyl)($C_{1-6}$alkyl), —O—$C_{1-6}$ alkyl or $C_{1-6}$alkyl, which is unsubstituted or substituted with fluoro,
  (4) heteroaryl, which is unsubstituted or substituted with halogen, hydroxyl, —$NH_2$, —NH—$C_{1-6}$alkyl, or —N($C_{1-6}$alkyl)($C_{1-6}$alkyl), —O—$C_{1-6}$alkyl or $C_{1-6}$alkyl, which is unsubstituted or substituted with fluoro,
  (5) —O-phenyl, which is unsubstituted or substituted with halogen, hydroxyl, —$NH_2$, —NH—$C_{1-6}$alkyl, or —N($C_{1-6}$alkyl)($C_{1-6}$alkyl), —O—$C_{1-6}$alkyl or $C_{1-6}$alkyl, which is unsubstituted or substituted with fluoro, and
  (6) —O-heteroaryl, which is unsubstituted or substituted with halogen, hydroxyl, —$NH_2$, —NH—$C_{1-6}$alkyl, or —N($C_{1-6}$alkyl)($C_{1-6}$alkyl), —O—$C_{1-6}$alkyl or $C_{1-6}$alkyl, which is unsubstituted or substituted with fluoro.

An embodiment of the present invention includes compounds wherein $R^{1a}$, $R^{1b}$, $R^{1c}$ are selected from the group consisting of:
  (1) hydrogen,
  (2) chloro,
  (3) fluoro,
  (4) bromo,
  (5) methyl,
  (6) methoxy,
  (7) (methyl)cyclopropyl-,
  (8) cyclopropyl,
  (9) (methoxy)phenyl-, and
  (10) (methyl)phenyl-.

An embodiment of the present invention includes compounds wherein $R^{2a}$, $R^{2b}$ and $R^{2c}$ are independently selected from the group consisting of:
  (1) hydrogen,
  (2) halogen,
  (3) hydroxyl,
  (4) $C_{1-6}$alkyl, which is unsubstituted or substituted with halogen, hydroxyl or phenyl or naphthyl,
  (5) —O—$C_{1-6}$alkyl, which is unsubstituted or substituted with halogen, hydroxyl or phenyl,
  (6) heterocyclyl, wherein heterocyclyl is selected from imidazolyl, isothiazolyl, oxazolyl, morpholinyl, pyrazolyl, pyridyl, tetrazolyl, and thiazolyl, which is unsubstituted or substituted with halogen, hydroxyl, $C_{1-6}$alkyl, —O—$C_{1-6}$alkyl or —$NO_2$, and
  (7) phenyl, which is unsubstituted or substituted with halogen, hydroxyl, $C_{1-6}$alkyl, —O—$C_{1-6}$alkyl or —$NO_2$.

An embodiment of the present invention includes compounds wherein is $R^{2c}$ is hydrogen and $R^{2a}$ and $R^{2b}$ are independently selected from the group consisting of:
  (1) hydrogen,
  (2) chloro,
  (3) fluoro,
  (4) bromo,
  (5) methyl,
  (6) cyclopropyl;
  (7) isopropoxy,
  (8) methoxy, and
  (9) t-butoxy.

An embodiment of the present invention includes compounds wherein is $R^{2c}$ is hydrogen and $R^{2a}$ and $R^{2b}$ are independently selected from the group consisting of:
  (1) hydrogen,
  (2) methyl, and
  (3) cyclopropyl.

An embodiment of the present invention includes compounds wherein is $R^{2c}$ is hydrogen, $R^{2b}$ is hydrogen or methyl and $R^{2a}$ is methyl or cyclopropyl.

An embodiment of the present invention includes compounds wherein $R^3$ is selected from the group consisting of $CH_3$, $CF_3$, and $CH_2F$.

An embodiment of the present invention includes compounds wherein $R^3$ is $CH_3$.

An embodiment of the present invention includes compounds wherein $R^4$ is selected from the group consisting of hydrogen and fluoro. An embodiment of the present invention includes compounds wherein $R^4$ is hydrogen.

An embodiment of the present invention includes compounds wherein $R^5$ is selected from the group consisting of hydrogen and methyl. An embodiment of the present invention includes compounds wherein $R^5$ is hydrogen.

Specific embodiments of the present invention include a compound which is selected from the group consisting of the subject compounds of the Examples herein and pharmaceutically acceptable salts thereof and individual enantiomers and diastereomers thereof.

As appreciated by those of skill in the art, halogen or halo as used herein are intended to include fluorine, chlorine, bromine and iodine. Similarly, "alkyl", as well as other groups having the prefix "alk", such as alkoxy, alkanoyl, means carbon chains which may be linear or branched or combinations thereof. $C_{1-6}$, as in $C_{1-6}$alkyl is defined to identify the group as having 1, 2, 3, 4, 5 or 6 carbons in a linear or branched arrangement, such as methyl, ethyl, n-propyl, isopropyl, n-butyl, iso-butyl, sec-butyl, tert-butyl, pentyl, hexyl, and the like. "Alkylene" means a straight or branched chain of carbon atoms with a group substituted at both ends, such as —$CH_2CH_2$— and —$CH_2CH_2CH_2$—. "Alkenyl" means a carbon chain which contains at least one carbon-carbon double bond, and which may be linear or branched or combinations thereof such that $C_{2-6}$alkenyl is defined to identify the group as having 2, 3, 4, 5 or 6 carbons which incorporates at least one double bond, which may be in a E- or a Z-arrangement, including vinyl, allyl, isopropenyl, pentenyl, hexenyl, heptenyl, 1-propenyl, 2-butenyl, 2-methyl-2-butenyl, and the like. "Alkynyl" means a carbon chain which contains at least one carbon-carbon triple bond, and which may be linear or branched or combinations thereof, such as ethynyl, propargyl, 3-methyl-1-pentynyl, 2-heptynyl and the like. "Cycloalkyl" means a mono-, bi- or tri-cyclic structure, optionally combined with linear or branched structures, having the indicated number of carbon atoms, such as cyclopropyl, cyclopentyl, cycloheptyl, adamantyl, cyclododecylmethyl, 2-ethyl-1-bicyclo[4.4.0]decyl, and the like. "Alkoxy" means an alkoxy group of a straight or branched chain having the indicated number of carbon atoms. $C_{1-6}$alkoxy, for example, includes methoxy, ethoxy, propoxy, isopropoxy, and the like. The term "heterocyclyl" as used herein includes both unsaturated heterocyclic moieties comprising a mono- or bicyclic aromatic rings with at least one ring containing a heteroatom selected from N, O and S, and each ring containing 5 or 6 atoms (i.e. "heteroaryl") and saturated heterocyclic moieties comprising mono- or bicyclic saturated rings with at least one ring containing a heteroatom selected from N, O and S, and each ring containing 3, 5 or 6 atoms. Examples of "heteroaryl" include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, furo(2,3-b)pyridyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof. Examples of saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

A group which is designated as being substituted with substituents may be substituted with multiple numbers of such substituents. A group which is designated as being independently substituted with substituents may be independently substituted with multiple numbers of such substituents. The term "substituted" means that one or more hydrogens on the designated group is(are) replaced with a selection from the indicated group, provided that the designated group's normal valency under the existing circumstances is not exceeded, and that the substitution results in a stable compound. Combinations of substituents and/or variables are permissible only if such combinations result in stable compounds. A reference to a "stable compound" or "stable structure" means that the compound is sufficiently robust to survive isolation to a useful degree of purity from a reaction mixture, and to survive formulation into an efficacious therapeutic agent.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art. The small molecule X-ray crystal structure of the compound of Example 2-29 indicated that the absolute sterochemical designation at the 1- and the 2-positions of the cylopropyl ring was (S,S). The absolute stereochemical designation for all of the other compounds in the Examples was assigned based on this structural determination of the compound of Example 2-29.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^{2}$H and $^{3}$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{23}$I and 125I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds are useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE10 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, may provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum may result in increased cAMP/cGMP signaling and striatal output, which has the potential to restore behavioral inhibition that is impaired in cognitive disease such as schizophrenia. Regulation and integration of glutamatergic and dopaminergic inputs may enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temperal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy. Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., *J. Biomol Screen*, 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product # R7506), at a final concentration of 50 nM are made in the assay buffer (10 mM Tris HCl, pH 7.2, 10 mM $MgCl_2$, 0.05% $NaN_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

$$\text{Polarization}(mP) = 1000 * (S/So - P/Po)/(S/So + P/Po).$$

Dose-inhibition profiles for each compound were characterized by fitting the mP data to a four-parameter equation given below. The apparent inhibition constant ($K_I$) the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA*, 2003, 8: 54-63, using the following equation:

$$mP = \frac{(0\% \ mP - 100\% \ mP)(Imax - Imin)}{1 + \left[\frac{[\text{Drug}]}{\left(10^{-pK_1}\left(1 + \frac{[\text{Substrate}]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 mL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

All of the final compounds of the following examples had activity in inhibiting the human PDE10 enzyme in the aforementioned assays, generally with an Ki of less than about 1 µM. In particular, all of the final compounds of the following examples had activity in inhibiting the human PDE10 enzyme in the aforementioned assays, generally with an Ki of less than about 0.1 µM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 µM, preferably less than or about 0.1 µM. The present invention also includes compounds within the generic scope of the invention which possess activity as inhibitors of other phosphodiesterase enzymes. With respect to 2-alkoxy pyrimidine compounds, the present compounds exhibit unexpected properties, such as regarding increased potency, oral bioavailability, metabolic stability, and/or decreased off target activity.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

REACTION SCHEME A

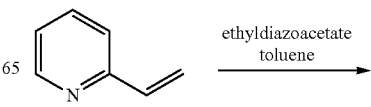

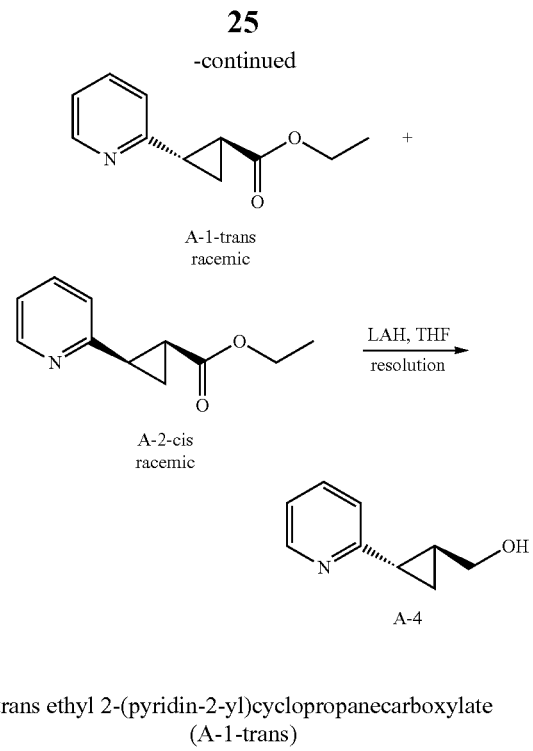

trans ethyl 2-(pyridin-2-yl)cyclopropanecarboxylate (A-1-trans)

A solution of 2-vinylpyridine (2 g, 19.02 mmol) in toluene (40 mL) was treated with ethyl diazoacetate (1.973 ml, 19.02 mmol) and stirred at reflux overnight. The mixture was concentrated in vacuo and the residue was purified by gradient elution on silica gel (0 to 50% EtOAc in hexanes) to elute peak 1 (A-1-trans) (1.6 g, 44%), then the solvent gradient was increased to 100% EtOAc to elute peak 2 (A-2-cis). (914 mg, 25%), both as yellow oils. Enantiomers of A-1-trans can be resolved by chiral preparative supercritical fluid chromatography (SFC) (3.0 cm i.d.×25 cm ChiralTech IC, 7% EtOH/$CO_2$, 70 mL/min) and analyzed by chiral analytical SFC (4.6 mm i.d.×25 cm ChiralTech IC, 7% EtOH/$CO_2$, 2.4 mL/min) $ent_1$=3.6 min, $ent_2$=4.1 min to give the title compound. $^1$H NMR δ (500 MHz, $CDCl_3$): 8.44 (m, 1H), 7.56 (td, J=7.6, 1.7 Hz, 1H), 7.22 (dd, J=7.8, 1.0 Hz, 1H), 7.08 (ddd, J=7.6, 4.9, 1.2 Hz, 1H), 4.17 (q, J=7.3 Hz, 2H), 2.58 (ddd, J=10.0, 6.1, 3.9 Hz, 1H), 2.25 (ddd, J=9.5, 5.6, 3.9 Hz, 1H), 1.61, (m, 2H), 1.28 (t, J=7.1 Hz, 3H). LRMS (ES) calculated M+H for C11H13NO2S: 192.2. Found: 192.1.

(S,S) trans 2-(pyridin-2-yl)cyclopropyl]methanol (A-4)

A solution of A-1-trans (751 mg, 3.93 mmol) in THF (20 mL) was cooled to 0° C. and treated slowly with lithium aluminum hydride (3.93 mL, 3.93 mmol, 1 M solution in THF). The solution was warmed to room temperature and stirred for 20 min. The reaction mixture was then re-cooled to 0° C. and treated sequentially dropwise with 0.15 mL of water, 0.15 ml of 15% NaOH, and 0.45 mL of water. Sodium sulfate was added to the mixture. After stirring at room temperature for 10 min, the mixture was filtered through a pad of Celite and the filtrate was concentrated in vacuo to afford the title compound as a pale yellow oil. The material was sufficiently pure to use in the subsequent step without further purification. $^1$H NMR (500 MHz, $CDCl_3$): δ 8.41 (d, J=4.2 Hz, 1H), 7.52 (td, J=7.6, 1.7 Hz, 1H), 7.10 (d, J=7.8 Hz, 1H), 7.03 (ddd, J=7.3, 4.9, 0.7 Hz, 1H), 3.72 (dd, J=11, 2, 6.4 Hz, 1H), 3.57 (dd, J=11.2, 7.1 Hz, 1H), 2.26 (bs, 1H), 1.98 (m, 1H), 1.74 (m, 1H), 1.25 (m, 1H), 0.96 (m, 1H) ppm; LRMS (ES) calculated M+H for $C_9H_{11}NO$: 150.2. Found: 150.1. As an alternate means to resolving enantiomers of this building block, the enantiomer A-4 was resolved from its corresponding enantiomer by chiral preparative SFC (3.0 cm i.d.×25 cm ChiralPak AD-H, 3:7:90 MeCN/MeOH/$CO_2$, 70 mL/min) and analyzed by chiral analytical SFC (4.6 mm i.d.×25 cm ChiralPak AD-H, 3:7:90 MeCN/MeOH/$CO_2$, 2.4 mL/min) $ent_1$=7.5 min, $ent_2$=8.4 min. Using this method, the (S,S) enantiomer was determined to be the second eluting peak and was isolated in 98.7% ee.

REACTION SCHEME B

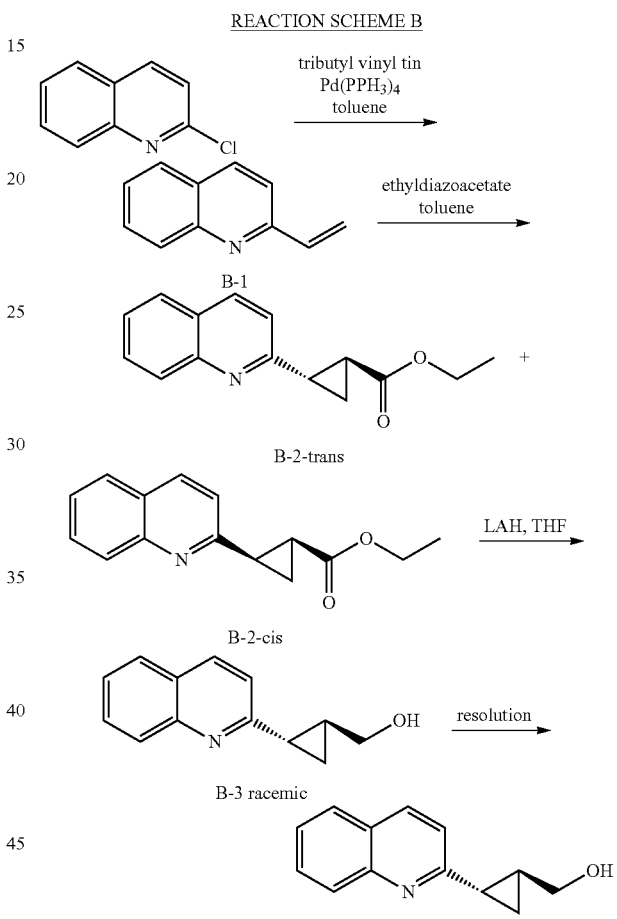

2-vinylquinoline (B-1)

A solution of 2-chloroquinoline (1 g, 6.11 mmol) and vinyl tributyl tin (2.69 mL, 9.17 mmol) in toluene (30 mL) was treated with $Pd(PPh_3)_4$ (0.706 g, 0.611 mmol) and heated to reflux for 1.5 h. The reaction mixture was concentrated and the resulting material was purified directly by gradient elution on silica gel (0 to 25% EtOAc in hexanes) to afford the title compound as a colorless oil (941 mg, 99%). LRMS m/z (M+H) 156.1 found, 156.2 required.

ethyl 2-(quinolin-2-yl)cyclopropanecarboxylate (B-2-trans)

A solution of B-1 (941 mg, 6.06 mmol) in toluene (20 ml) was treated with ethyl diazoacetate (0.629 mL, 6.06 mmol)

and stirred at reflux overnight. The mixture was concentrated and the residue was purified by gradient elution on silica gel (0 to 30% EtOAc in hexanes) to elute peak 1 (trans diastereomer). The eluent was then ramped up (50% EtOAc in hexanes) to elute peak 2 (cis diastereomer). This afforded the title compound as a pale yellow oil (706 mg, 40%, ca. 70% pure), which could be used in the subsequent step without further purification. LRMS m/z (M+H) 242.2 found, 242.3 required.

(S,S) 2-(quinolin-2-yl)cyclopropyl]methanol (B-4)

A solution of the B-2-trans (200 mg, 0.829 mmol) in THF (20 mL) was cooled to 0° C. and treated slowly with a 1M THF solution of LiAlH$_4$ (0.829 mL, 0.829 mmol). The solution was warmed to room temperature and stirred for 20 min. The mixture was re-cooled to 0° C. and treated dropwise with 0.03 mL of water, 0.03 ml of 15% NaOH, and 0.09 mL of water successively. Sodium sulfate was added to the mixture, and after stirring at room temperature for 10 min, the mixture was filtered through Celite, eluting exhaustively with CH$_2$Cl$_2$ and MeOH. The filtrate was concentrated in vacuo, and the resulting residue was purified by gradient elution on silica gel (0 to 100% EtOAc in hexanes) to afford the title compound as a colorless oil (130 mg, 79%). $^1$H NMR (500 MHz, CDCl$_3$): δ 7.93 (d, J=3.5 Hz, 1 H), 7.90 (d, J=3.5 Hz, 1 H), 7.67 (d, J=8.1 Hz, 1H), 7.59 (td, J=7.6, 1.4 Hz, 1 H), 7.38 (td, J=7.6, 1.0 Hz, 1 H), 7.09 (d, J=8.5 Hz, 1 H), 3.76 (dd, J=11.4, 6.0 Hz, 1H), 3.56 (dd, J=11.4, 7.2 Hz, 1H), 2.15 (dt, J=8.5, 4.4 Hz, 1H), 1.84 (m, 1H), 1.33 (dt, J=8.6, 4.4 Hz, 1H), 1.01 (ddd, J=10.4, 5.9, 1.1 Hz, 1H) ppm; LRMS m/z (M+H) 200.1 found, 200.2 required. The enantiomer B-4 was resolved from its corresponding enantiomer by chiral preparative SFC (3.0 cm i.d.×25 cm ChiralPak AD-H, 30% MeOH/CO$_2$+0.1% DEA, 70 mL/min) and analyzed by chiral analytical SFC (4.6 mm i.d.×25 cm ChiralPak AD-H, 30% MeOH/CO$_2$+0.1% DEA, 2.4 mL/min) ent$_1$=2.8 min, ent$_2$=3.5 min. Using this method, the (S,S) enantiomer was determined to be the first eluting peak and was isolated in >99%.

REACTION SCHEME C

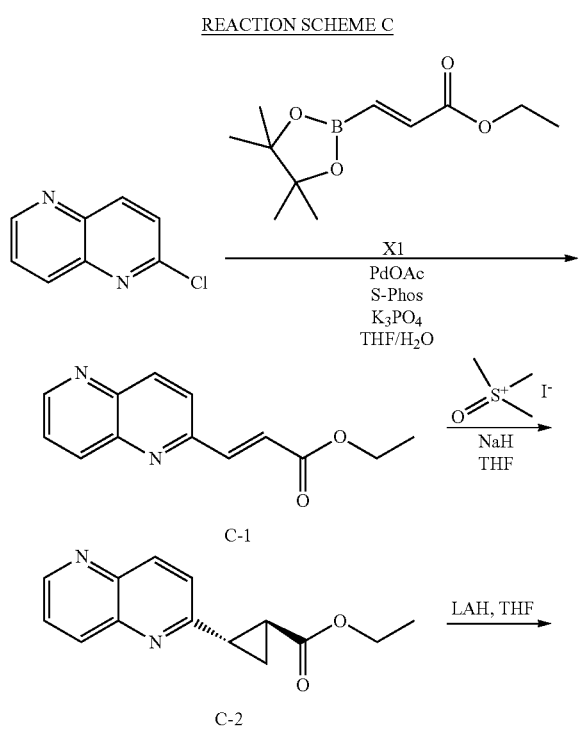

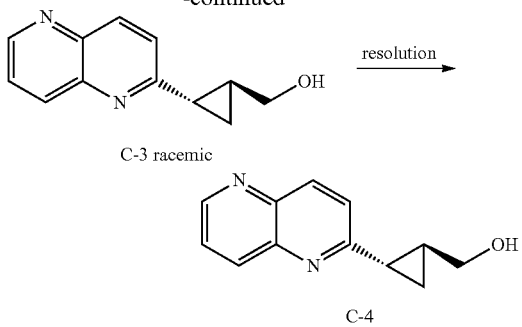

ethyl 3-(1,5-naphthyridin-2-yl)prop-2-enoate (C-1)

2-chloro-1,5-naphthyridine (101 mg, 0.614 mmol), boronate ester X1 (195 mg, 0.920 mmol), S-Phos (25.2 mg, 0.061 mmol), K$_3$PO$_4$ (391 mg, 1.84 mmol) and PdOAc$_2$ (6.89 mg, 0.031 mmol) were combined in a 5-mL microwave vial in THF (2.5 mL) and water (500 µl). The reaction mixture was heated at 100° C. for 15 min. The reaction mixture was diluted with EtOAc (20 mL), washed with sat. aq. NaHCO$_3$ (25 mL) and brine (25 mL), dried over MgSO$_4$, filtered, and concentrated in vacuo. The resulting residue was purified by gradient elution on silica gel (10 to 100% EtOAc in hexanes) to afford the title compound as a pale orange solid (118 mg, 90%). $^1$H NMR (500 MHz, DMSO): δ 9.02 (dd, J=4.1, 1.6 Hz, 1 H), 8.48 (d, J=8.8 Hz, 1 H), 8.48-8.42 (m, 1 H), 8.25 (d, J=8.7 Hz, 1 H), 7.84-7.79 (m, 2 H), 7.13 (d, J=16.0 Hz, 1 H), 4.25 (q, J=7.1 Hz, 2 H), 1.30 (t, J=7.1 Hz, 3 H) ppm; LRMS m/z (M+H) 229.2 found, 229.1 required.

ethyl 2-(1,5-naphthyridin-2-yl)cyclopropanecarboxylate (C-2)

To a 5-mL sealed vial was added trimethyl sulfoxonium iodide (170 mg, 0.770 mmol), DMSO (2567 µl), and NaH (26.7 mg, 0.668 mmol). This mixture was stirred for 40 min at 50° C. The reaction mixture was then cooled to room temperature and to it was added a solution of C-1 (110 mg, 0.513 mmol) in DMSO (1.5 mL). The reaction mixture was stirred at room temperature for 5 min, and then diluted with EtOAc (75 mL) and washed with sat. aq. NaHCO$_3$ (4×20 mL). The organics were dried over MgSO$_4$, filtered, and concentrated in vacuo. The resulting residue was purified by gradient elution on silica gel (20 to 100% EtOAc in hexanes) to afford the title compound (67 mg, 57%). $^1$H NMR (500 MHz, CDCl$_3$): δ 8.89 (dd, J=4.2, 1.6 Hz, 1H), 8.28 (d, J=8.6 Hz, 1H), 8.23 (d, J=8.6 Hz, 1H), 7.60-7.57 (m, 2H), 4.20 (q, J=7.1 Hz, 2H), 2.82-2.77 (m, 1H), 2.47-2.42 (m, 1H), 1.79 (ddd, J=8.6, 6.0, 3.8 Hz, 1H), 1.71 (ddd, J=8.9, 5.6, 3.8 Hz, 1H), 1.29 (t, J=7.2 Hz, 3H) ppm; LRMS m/z (M+H) 243.3 found, 243.3 required.

(S,S) [2-(1,5-naphthyridin-2-yl)cyclopropyl]methanol (C-4)

The title compound was prepared from C-2 according to the protocol outlined in Scheme A to afford the title compound as a brown gum. $^1$H NMR (500 MHz, CDCl$_3$): δ 8.86 (dd, J=4.2, 1.6 Hz, 1H), 8.21-8.26 (m, 2H), 7.57 (dd, J=8.5, 4.2 Hz, 1H), 7.44 (d, J=8.7 Hz, 1H), 3.77 (dd, J=11.3, 6.3 Hz, 1H), 3.68 (dd, J=11.3, 6.9 Hz, 1H), 2.21 (dt, J=8.6, 4.5 Hz, 1H), 1.99-1.92 (m, 1H), 1.48-1.42 (m, 1H), 1.16-1.10 (m, 1H); LRMS m/z (M+H) 201.3 found, 201.2 required. The enantiomer C-4 was resolved from its corresponding enantiomer by chiral preparative SFC (3.0 cm i.d.×25 cm ChiralPak AD-H, 30% MeOH/CO$_2$+0.1% DEA, 70 mL/min) and analyzed by chiral analytical SFC (4.6 mm i.d.×25 cm ChiralPak AD-H, 30% MeOH/CO$_2$+0.1% DEA, 2.4 mL/min) ent$_1$=3.4 min, ent$_2$=4.7 min. Using this method, the (S,S) enantiomer was determined to be the second eluting peak and was isolated in >99% ee.

REACTION SCHEME D

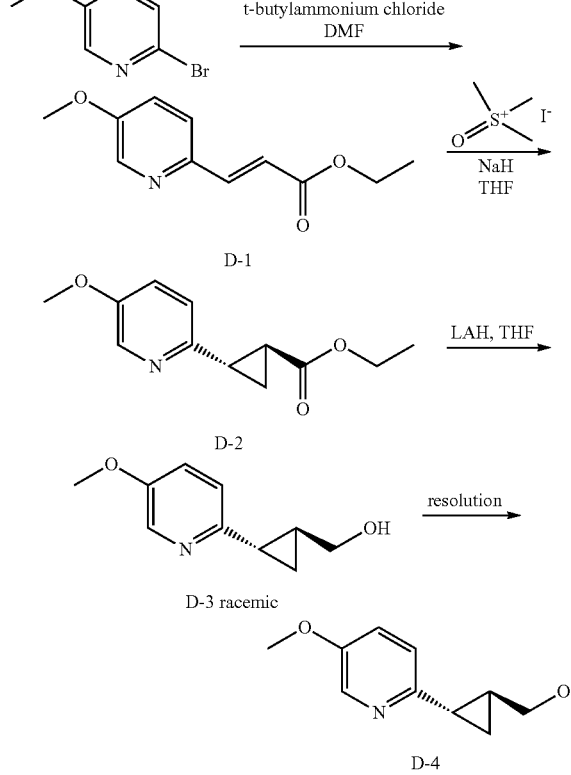

ethyl 3-(5-methoxypyridin-2-yl)prop-2-enoate (D-1)

To a 25-mL microwave vial was added 2-bromo-5-methoxy pyridine (1.88 g, 10 mmol), ethyl acrylate (5.44 ml, 50.0 mmol), Pd(OAc)$_2$ (0.225 g, 1.000 mmol), K$_2$CO$_3$ (4.15 g, 30.0 mmol), and t-butylammonium chloride hydrate (2.96 g, 10.00 mmol). The slurry was heated in the microwave at 160° C. for 1 h. Upon cooling to room temperature, the mixture was diluted with EtOAc (100 mL) and washed with sat. aq. NaHCO3 (100 mL). The aqueous layer was extracted with additional EtOAc (2×50 mL). The combined organic layers were then washed with water and brine, dried over Na$_2$SO$_4$, filtered, and concentrated in vacuo. The resulting residue was purified by gradient elution on silica gel (0 to 50% EtOAc in hexanes) to afford the title compound (1.5 g, 72%). $^1$H NMR (500 MHz, CDCl$_3$): δ 8.35 (d, J=3.0 Hz, 1H), 7.65 (d, J=15.7 Hz, 1H), 7.38 (d, J=8.6 Hz, 1H), 7.18 (dd, J=8.6, 3.0 Hz, 1H), 6.76 (d, J=15.7 Hz, 1H), 4.26 (q, J=7.1 Hz, 2H), 3.89 (s, 3H), 1.33 (t, J=7.1 Hz, 3H) ppm; LRMS m/z (M+H) 208.0 found, 208.2 required.

ethyl 2-(5-methoxypyridin-2-yl)cyclopropanecarboxylate (D-2)

The title compound was prepared from D-1 according to the protocol outlined in Scheme C to afford D-2 as a light yellow solid. $^1$H NMR (500 MHz, CDCl$_3$): δ 8.15 (d, J=2.9 Hz, 1H), 7.14 (d, J=8.0 Hz, 1H), 7.10 (dd, J=8.0, 2.9 Hz, 1H), 4.16 (q, J=7.1 Hz, 2H), 3.82 (s, 3H), 2.58-2.52 (m, 1H), 2.18-2.12 (m, 1H), 1.56 (m, 1H), 1.54 (m, 1H), 1.27 (t, J=7.1 Hz, 3H) ppm; LRMS m/z (M+H) 222.3 found, 222.3 required.

(S,S) [2-(5-methoxypyridin-2-yl)cyclopropyl]methanol (D-4)

The title compound was prepared from D-2 according to the protocol outlined in Scheme A to afford D-4 as a light yellow oil. $^1$H NMR (500 MHz, CDCl$_3$): δ 8.14 (d, J=2.9 Hz, 1H), 7.09 (dd, J=8.6, 2.9 Hz, 1H), 7.04 (d, J=8.6 Hz, 1H), 3.82 (s, 3H), 3.72-3.66 (m, 1H), 3.61-3.55 (m, 1H), 1.97-1.91 (m, 1H), 1.69-1.62 (m, 1H), 1.20-1.14 (m, 1H), 0.91 (1 H, dt, J=8.71, 5.06 Hz) ppm; LRMS m/z (M+H) 180.1 found, 180.1 required. The enantiomer D-4 was resolved from its corresponding enantiomer by chiral preparative SFC (3.0 cm i.d.× 25 cm ChiralPak AD-H, 6.7/13.3/80 MeCN/MeOH/CO$_2$, +0.1% DEA, 70 mL/min) and analyzed by chiral analytical SFC (4.6 cm i.d.×25 cm ChiralPak AD-H, 6.7/13.3/80 MeCN/MeOH/CO$_2$, +0.1% DEA, mL/m) ent$_1$=3.7 min, ent$_2$=4.4 min. Using this method, the (S,S) enantiomer was determined to be the second eluting peak and was isolated in >99% ee.

REACTION SCHEME E

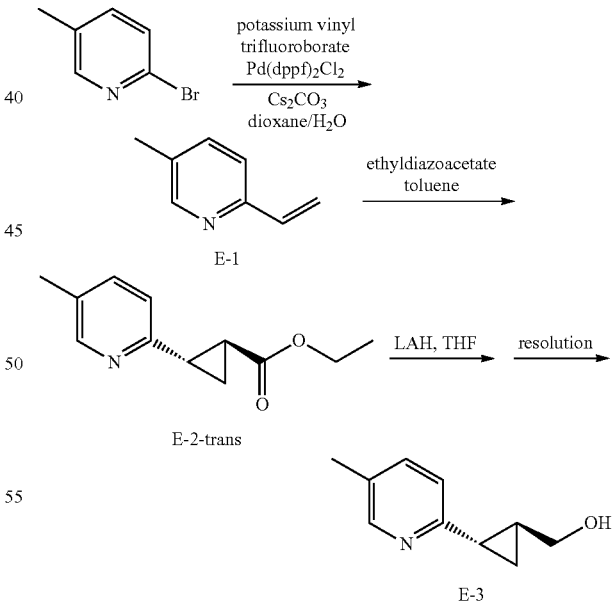

2-bromo-5-(fluoromethyl)pyridine (E-1)

To a stirred solution of 2-bromo-5-methylpyridine (23.8 g, 138.0 mmol) and potassium vinyl trifluoroborate (20.39 g, 152.0 mmol) in dioxane (235 mL) under nitrogen was added Pd(dppf)$_2$Cl$_2$ (11.30 g, 13.8 mmol), cesium carbonate (135.0 g, 415.0 mmol), and water (41.5 mL). The resulting mixture heated to 100° C. for 2 hours. The reaction was partitioned between ethyl acetate and saturated sodium bicarbonate solution. The organic phase was concentrated and flash column separation using a 0-30% ethyl acetate/hexane gradient gave E-1 as a volatile oil, which was carried on directly to next step.

ethyl 2-(5-methylpyridin-2-yl)cyclopropanecarboxylate (E-2-trans)

To a stirred solution of E-1 (16.44 g, 138.0 mmol) in toluene (300 mL) was added ethyl diazoacetate (42.9 ml, 414.0 mmol) and the resulting mixture was heated to 100° C. for 3 hours. The mixture was allowed to cool and partitioned between ethyl acetate and saturated sodium bicarbonate solution. The organic phase was concentrated and flash column separation using a 0-20% ethyl acetate/hexane gradient gave E-2-trans as an oil. (11.7 g, 41%). LRMS (ES) (M+H)$^+$: observed=206.2, calculated=206.2.

(S,S) 2-(5-methylpyridin-2-yl)cyclopropyl]methanol (E-3)

A solution of E-2-trans (5.0 g, 24.36 mmol) in THF (80 mL) was cooled to 0° C. and treated slowly with lithium aluminum hydride (55.0 mL, 55.0 mmol, 1 M solution in THF). The solution was stirred for 30 min at 0° C. The reaction mixture was then treated sequentially dropwise with 2.0 mL of water, 2.0 ml of 15% NaOH, and 6.0 mL of water. Sodium sulfate was added to the mixture. After stirring at room temperature for 4 hours, the mixture was filtered and the filtrate was concentrated in vacuo to afford the title compound as a pale yellow oil. (3.4 g, 85.4%). LRMS (ES) (M+H)$^+$: observed=164.2, calculated=164.2. $^1$H NMR (400 MHz, DMSO-$d_6$): δ 8.21 (m, 1H), 7.41 (m, 1H), 7.12 (m, 1H), 4.57 (m, 1H) 3.44 (m, 1H), 3.33 (m, 1H), 2.21 (s, 3H), 1.88 (m, 1H), 1.44 (m, 1H), 0.98 (m, 1H), 0.81 (m, 1H). The enantiomer E-3 was resolved from its corresponding enantiomer by chiral preparative SFC (3.0 cm i.d.×25 cm ChiralPak AS-H, 10% iPrOH/CO$_2$+0.1% DEA, 80 mL/min) and analyzed by chiral analytical SFC (4.6 mm i.d.×15 cm ChiralPak AS-H, 15% iPrOH/CO$_2$+0.1% DEA, 2.4 mL/min) ent$_1$=3.7 min, ent$_2$=4.5 min to give the title compound. Using this method, the (S,S) enantiomer was determined to be the second eluting peak and was isolated in >99% ee.

REACTION SCHEME F

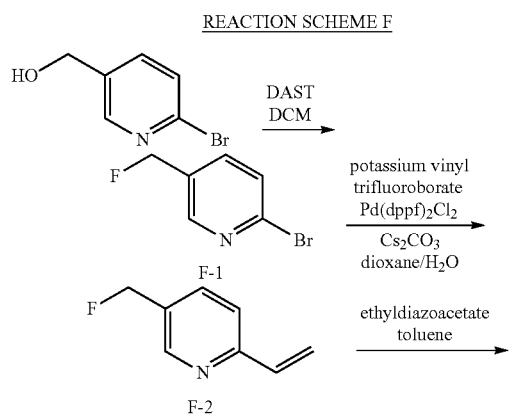

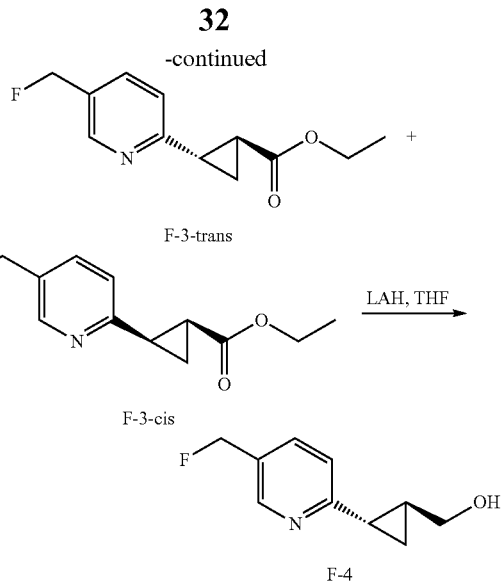

2-bromo-5-(fluoromethyl)pyridine (F-1)

To a stirred solution of (6-bromopyridin-3-yl)methanol (1.00 g, 5.32 mmol) in dichloromethane (25 mL) at 0° C. was added DAST (0.70 mL, 5.32 mmol) and the resulting solution was stirred at 0° C. for one hour. The mixture was washed with a saturated sodium bicarbonate solution and concentrated. Flash column separation using a 0-10% ethyl acetate/hexane gradient gave F-1 (0.37 g, 37%). LRMS (ES) (M+14)$^+$: observed=190.0/192.0, calculated=190.0/192.0.

5-(fluoromethyl)-2-vinylpyridine (F-2)

To a stirred solution of F-1 (1.09 g, 5.74 mmol) and potassium vinyl trifluoroborate (1.54 g, 11.47 mmol) in dioxane (9.75 mL) under nitrogen was added Pd(dppf)$_2$Cl$_2$ (0.47 g, 0.57 mmol), cesium carbonate (5.61 g, 17.21 mmol), and water (1.72 mL). The resulting mixture heated to 100° C. for 90 minutes. The reaction was partitioned between ethyl acetate and saturated sodium bicarbonate solution. The organic phase was concentrated and flash column separation using a 0-15% ethyl acetate/hexane gradient gave F-2 as an oil (0.53 g, 67%). LRMS (ES) (M+H)$^+$: observed=138.0, calculated=138.1.

ethyl 2-(5-(fluoromethyl)pyridin-2-yl)cyclopropanecarboxylate (F-3-trans)

The title compound was prepared from F-2 according to the protocol outlined in Scheme A, carried through as the trans racemate without chiral resolution, to afford F-3-trans as a brown oil. LRMS (ES) (M+H)$^+$: observed=224.2, calculated=224.2.

2-(5-(fluoromethyl)pyridin-2-yl)cyclopropyl)methanol (F-4)

The title compound was prepared from F-3-trans according to the protocol outlined in Scheme A to afford F-4 as a yellow oil. LRMS (ES) (M+H)$^+$: observed=182.2, calculated=182.2.

REACTION SCHEME G

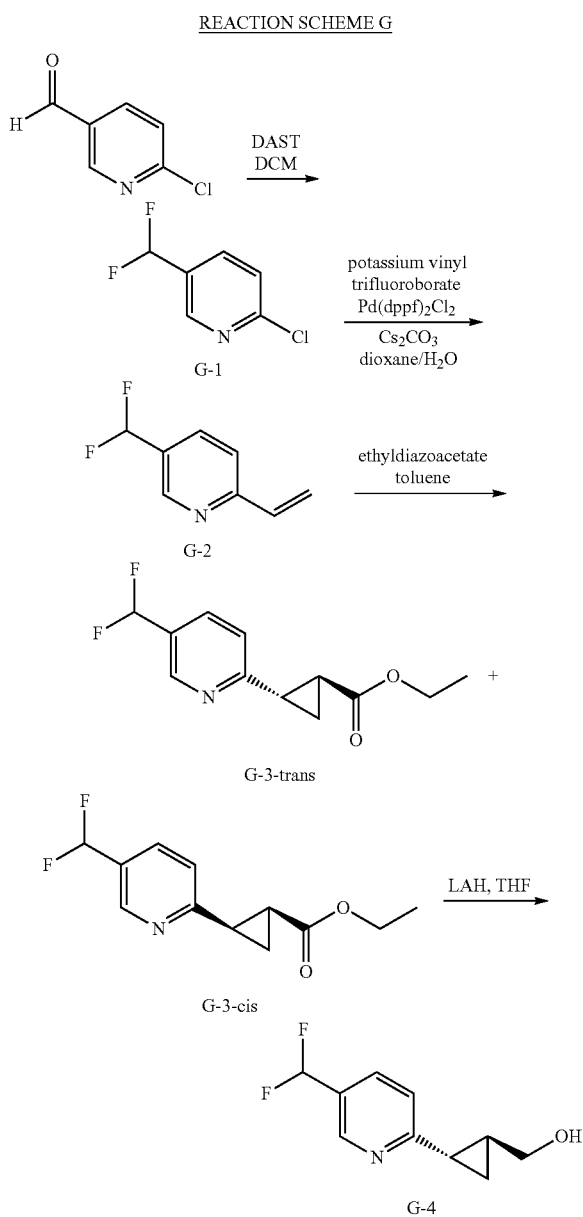

2-chloro-5-(difluoromethyl)pyridine (G-1)

The title compound was prepared from 2-chloro-5-pyridinecarboxaldehyde according to the protocol outlined in Scheme F to afford G-1. LRMS (ES) (M+H)+: observed=164.1, calculated=164.5.

5-(difluoromethyl)-2-vinylpyridine (G-2)

The title compound was prepared from G-1 according to the protocol outlined in Scheme F to afford G-2 as an oil. LRMS (ES) (M+H)+: observed=156.1, calculated=156.1.

ethyl 2-(5-(difluoromethyl)pyridin-2-yl)cyclopropanecarboxylate (G-3-trans)

The title compound was prepared from G-2 according to the protocol outlined in Scheme A, carried through as the trans racemate without chiral resolution, to afford G-3-trans as an oil. LRMS (ES) (M+H)+: observed=242.2, calculated=242.2.

2-(5-(difluoromethyl)pyridin-2-yl)cyclopropyl)methanol CG-4)

The title compound was prepared from G-3-trans according to the protocol outlined in Scheme A to afford G-4 as a yellow oil. LRMS (ES) (M+H)+: observed=200.2, calculated=200.2.

REACTION SCHEME H

3-methyl-6-vinylpyridazine (H-1)

The title compound was prepared from 3-chloro-6-methylpyridazine according to the protocol outlined in Scheme F to afford H-1 as an oil. LRMS (ES) (M+H)+: observed=121.1, calculated=121.1.

ethyl 2-(6-methylpyridazin-3-yl)cyclopropanecarboxylate (H-2-trans)

The title compound was prepared from H-1 according to the protocol outlined in Scheme A, carried through as the trans racemate without chiral resolution to afford H-2-trans as an oil. LRMS (ES) (M+H)+: observed=207.2, calculated=207.2.

2-(6-methylpyridazin-3-yl)cyclopropyl)methanol (H-3)

The title compound was prepared from H-2-trans according to the protocol outlined in Scheme A to afford H-3 as an oil. LRMS (ES) (M+H)+: observed=165.2, calculated=165.2.

REACTION SCHEME I

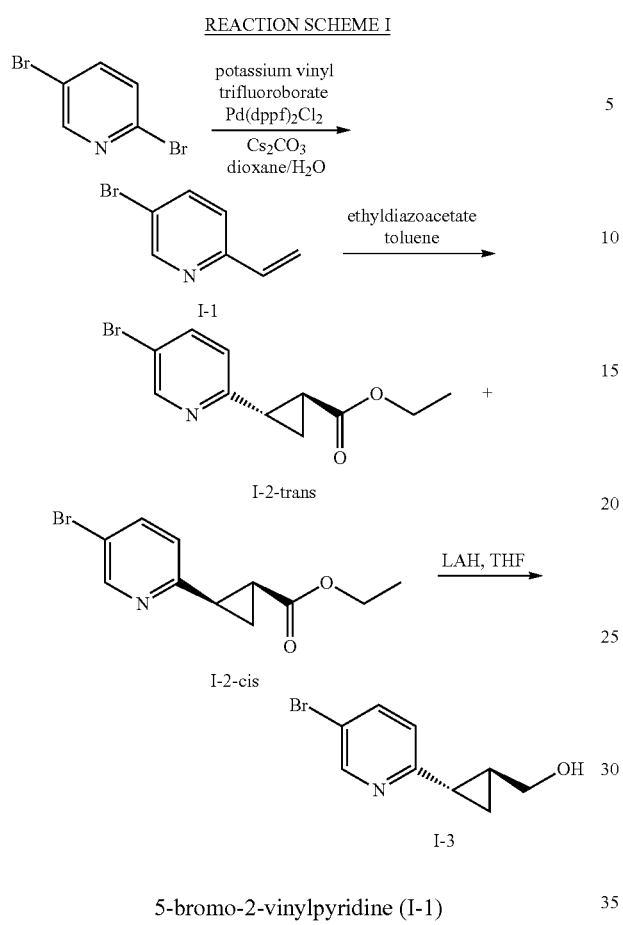

5-bromo-2-vinylpyridine (I-1)

The title compound was prepared from 2,5-dibromopyridine according to the protocol outlined in Scheme F to afford I-1 as an oil. LRMS (ES) (M+H)+: observed=184.0/186.0, calculated=184.0/186.0.

ethyl 2-(5-bromopyridin-2-yl)cyclopropanecarboxylate (I-2-trans)

The title compound was prepared from I-1 according to the protocol outlined in Scheme A, carried through as the trans racemate without chiral resolution, to afford I-2-trans as an oil. LRMS (ES) (M+H)+: observed=270.1/272.1, calculated=270.1/272.1.

2-(5-bromopyridin-2-yl)cyclopropyl)methanol (I-3)

The title compound was prepared from I-2-trans according to the protocol outlined in Scheme A to afford I-3 as an oil. LRMS (ES) (M+H)+: observed=228.1/230.1, calculated=228.1/230.1.

REACTION SCHEME J

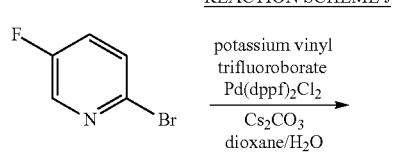

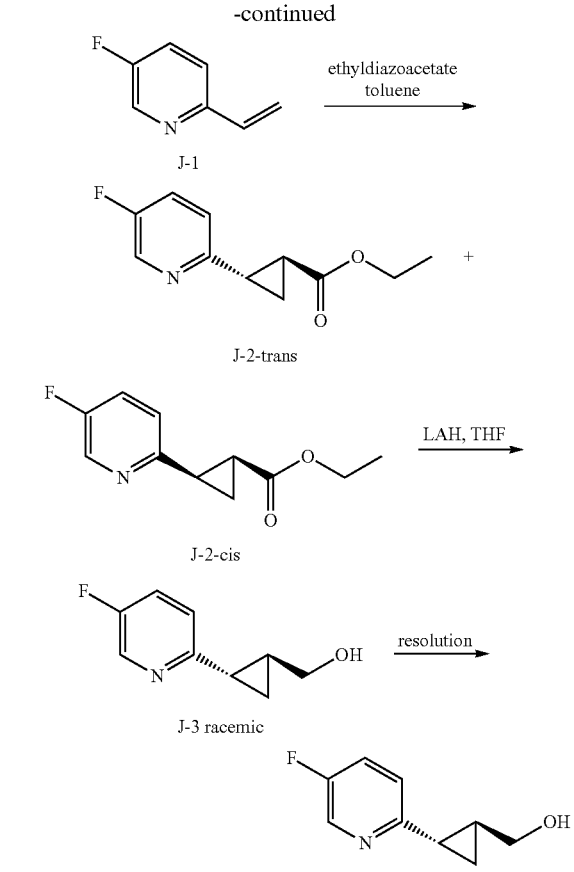

ethyl 2-(5-fluoropyridin-2-yl)cyclopropanecarboxylate (J-2-trans)

2-bromo-5-fluoropyridine was used to prepare J-1 according to the protocol outlined in Scheme F. J-1 was used directly to prepare the title compound according to the protocol outlined in Scheme A to afford J-2-trans as an oil. LRMS (ES) (M+H)+: observed=210.2, calculated=210.2.

2-(5-fluoropyridin-2-yl)cyclopropyl)methanol (J-4)

The title compound was prepared from J-2-trans according to the protocol outlined in Scheme A to afford J-4 as an oil. LRMS (ES) (M+H)+: observed=168.0, calculated=168.2.

REACTION SCHEME K

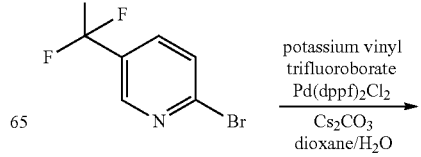

-continued

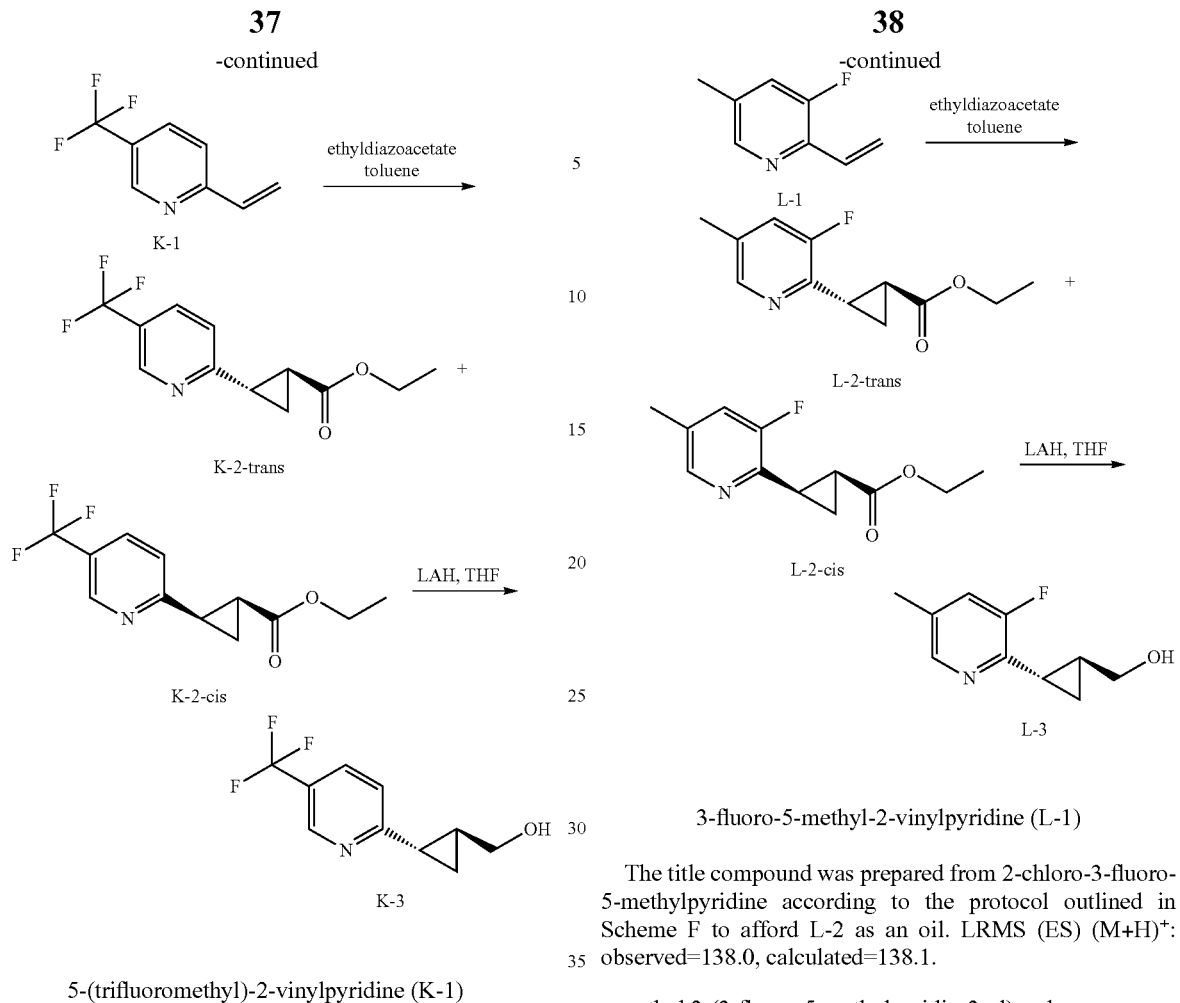

5-(trifluoromethyl)-2-vinylpyridine (K-1)

The title compound was prepared from 2-bromo-5-trifluoromethylpyridine according to the protocol outlined in Scheme F to afford K-1 as an oil. LRMS (ES) (M+H)+: observed=174.0, calculated=174.1.

ethyl 2-(5-(trifluoromethyl)pyridin-2-yl)cyclopropanecarboxylate (K-2-trans)

The title compound was prepared from K-1 according to the protocol outlined in Scheme A, carried through as the trans racemate without chiral resolution, to afford K-3-trans as an oil. LRMS (ES) (M+H)+: observed=260.1, calculated=260.2.

2-(5-(trifluoromethyl)pyridin-2-yl)cyclopropyl)methanol (K-3)

The title compound was prepared from K-3-trans according to the protocol outlined in Scheme A to afford K-4 as an oil. LRMS (ES) (M+H)+: observed=218.1, calculated=218.2.

REACTION SCHEME L

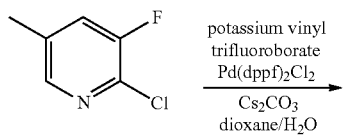

3-fluoro-5-methyl-2-vinylpyridine (L-1)

The title compound was prepared from 2-chloro-3-fluoro-5-methylpyridine according to the protocol outlined in Scheme F to afford L-2 as an oil. LRMS (ES) (M+H)+: observed=138.0, calculated=138.1.

ethyl 2-(3-fluoro-5-methylpyridin-2-yl)cyclopropanecarboxylate (L-2-trans)

The title compound was prepared from L-1 according to the protocol outlined in Scheme A, carried through as the trans racemate without chiral resolution, to afford L-2-trans as an oil. LRMS (ES) (M+H)+: observed=224.2, calculated=224.2.

2-(3-fluoro-5-methylpyridin-2-yl)cyclopropyl)methanol (L-3)

The title compound was prepared from L-2-trans according to the protocol outlined in Scheme A, to afford L-3 as an oil. LRMS (ES) (M+H)+: observed=182.1, calculated=182.2.

REACTION SCHEME M

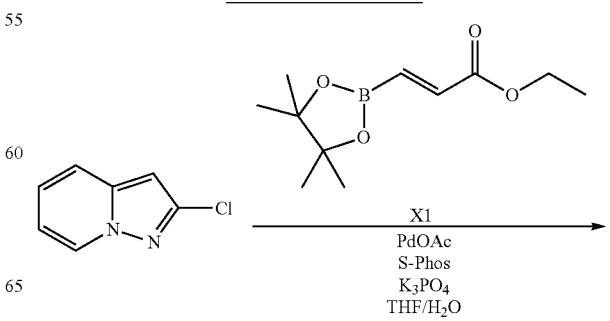

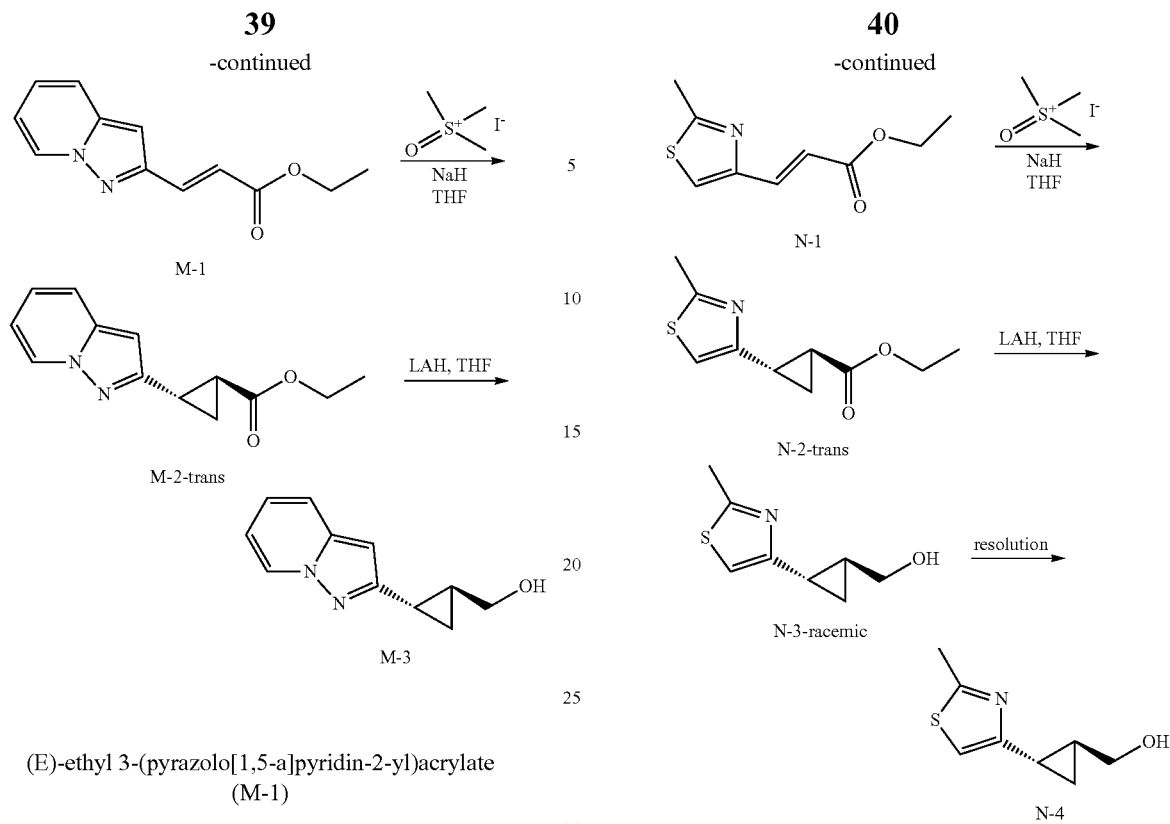

(E)-ethyl 3-(pyrazolo[1,5-a]pyridin-2-yl)acrylate (M-1)

The title compound was prepared from 2-chloropyrazolo[1,5-a]pyridine according to the protocol outlined in Scheme C to afford M-1 as a solid. LRMS (ES) (M+H)$^+$: observed=203.2, calculated=203.2.

ethyl 2-(pyrazolo[1,5-a]pyridin-2-yl)cyclopropanecarboxylate (M-2-trans)

The title compound was prepared from M-1 according to the protocol outlined in Scheme C, carried through as the trans racemate without chiral resolution to afford M-2-trans as a solid. LRMS (ES) (M+H)$^+$: observed=217.1, calculated=217.2.

2-(pyrazolo[1,5-a]pyridin-2-yl)cyclopropyl)methanol (M-3)

The title compound was prepared from M-2-trans according to the protocol outlined in Scheme A, to afford M-3 as an oil. LRMS (ES) (M+H)$^+$: observed=189.2, calculated=189.2.

REACTION SCHEME N

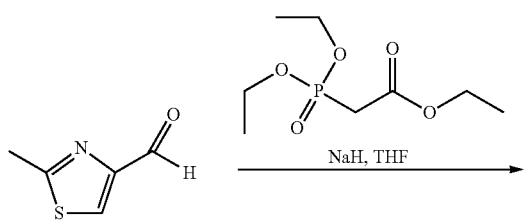

ethyl 3-(2-methylthiazol-4-yl)acrylate (N-1)

To a stirred solution of sodium hydride (1.04 g, 26.0 mmol) in THF (47.2 mL) was added triethyl phosphonoacetate (5.19 mL, 26.0 mmol) portionwise at room temperature. The resulting mixture was stirred for 30 minutes at room temperature. To this mixture was added a solution of 2-methylthiazole-4-carbaldehyde (3.0 g, 23.6 mmol) dissolved in THF (30 mL) with vigorous stirring. The reaction was stirred for 1 hour, partitioned between ethyl acetate and saturated sodium bicarbonate solution. The organic phase was washed with brine, dried over sodium sulfate, and concentrated to give the title compound as a yellow oil (4.3 g, 92%). LRMS (ES) (M+H)$^+$: observed=198.1, calculated=198.2.

ethyl 2-(2-methylthiazol-4-yl)cyclopropanecarboxylate (N-2-trans)

The title compound was prepared from N-1 according to the protocol outlined in Scheme C to afford N-2-trans. LRMS (ES) (M+H)$^+$: observed=212.2, calculated=212.2.

2-(2-methylthiazol-4-yl)cyclopropyl)methanol (N-4)

The title compound was prepared from N-2-trans according to the protocol outlined in Scheme A to afford N-4 as a solid. LRMS (ES) (M+H)$^+$: observed=170.1, calculated=170.2.

REACTION SCHEME O

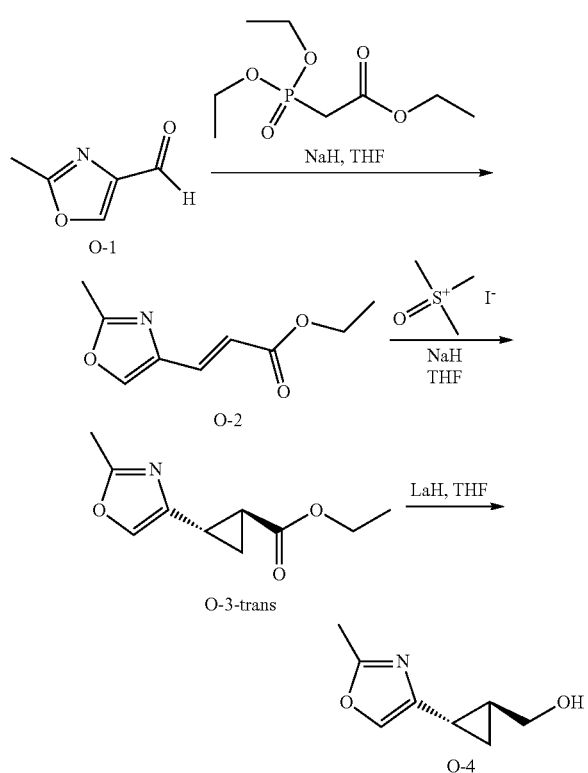

(E)-ethyl 3-(2-methyloxazol-4-yl)acrylate (O-2)

The title compound was prepared from O-1 according to the protocol outlined in Scheme N, to afford O-2. LRMS (ES) (M+H)+: observed=182.1, calculated=182.1.

ethyl 2-(2-methyloxazol-4-yl)cyclopropanecarboxylate (O-3-trans)

The title compound was prepared from O-2 according to the protocol outlined in Scheme C, carried through as the trans racemate without chiral resolution to afford O-3-trans as an oil. LRMS (ES) (M+H)+: observed=196.2, calculated=196.2.

2-(2-methyloxazol-4-yl)cyclopropyl)methanol (O-4)

The title compound was prepared from O-3-trans according to the protocol outlined in Scheme A, to afford O-4 as a solid. LRMS (ES) (M+H)+: observed=154.1, calculated=154.1.

REACTION SCHEME P

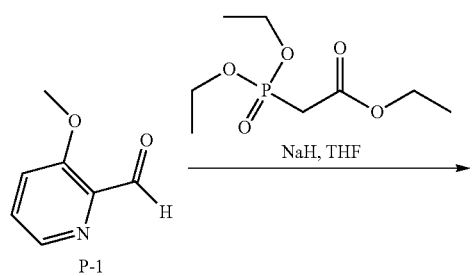

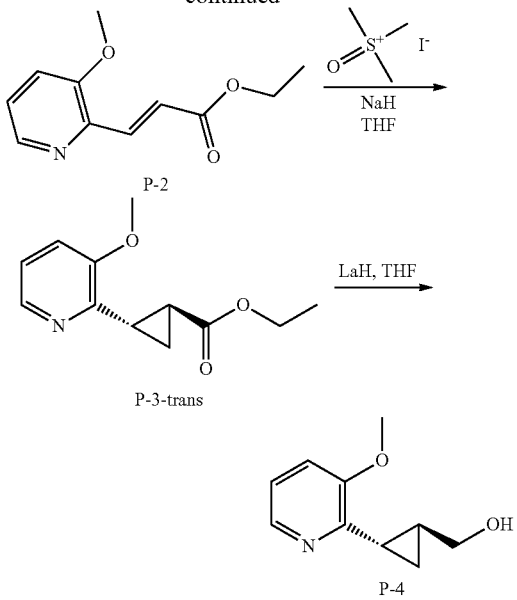

(E)-ethyl 3-(3-methoxypyridin-2-yl)acrylate (P-2)

The title compound was prepared from P-1 according to the protocol outlined in Scheme N, to afford P-2. LRMS (ES) (M+H)+: observed=208.1, calculated=208.2.

ethyl 2-(3-methoxypyridin-2-yl)cyclopropanecarboxylate (P-3-trans)

The title compound was prepared from P-2 according to the protocol outlined in Scheme C, carried through as the trans racemate without chiral resolution to afford P-3-trans as an oil. LRMS (ES) (M+H)+: observed=222.2, calculated=222.2.

2-(3-methoxypyridin-2-yl)cyclopropyl)methanol (P-4)

The title compound was prepared from P-3-trans according to the protocol outlined in Scheme A, to afford P-4 as a solid. LRMS (ES) (M+H)+: observed=180.2, calculated=180.2.

REACTION SCHEME Q

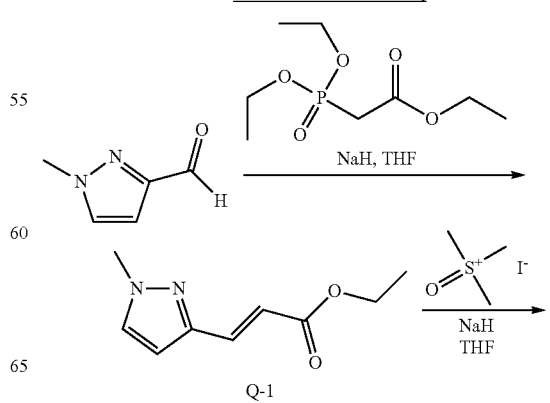

-continued

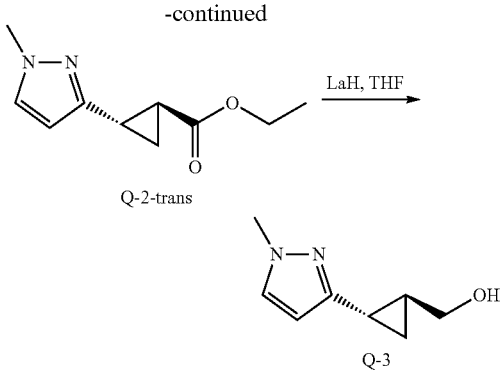

ethyl 2-(1-methyl-1H-pyrazol-3-yl)cyclopropanecarboxylate (Q2-trans)

The title compound was prepared from 1-methyl-1H-pyrazole-3-carbaldehyde according to the protocol outlined in Scheme N to afford Q-1, which was carried on directly using the protocol outlined in Scheme C, carried through as the trans racemate without chiral resolution, to afford Q-2-trans as an oil. LRMS (ES) (M+H)+: observed=195.3, calculated=195.2.

2-(1-methyl-1H-pyrazol-3-yl)cyclopropyl)methanol (Q-3)

The title compound was prepared from Q-2-trans according to the protocol outlined in Scheme A to afford Q-3 as a solid. LRMS (ES) (M+H)+: observed=153.2, calculated=153.2.

REACTION SCHEME R

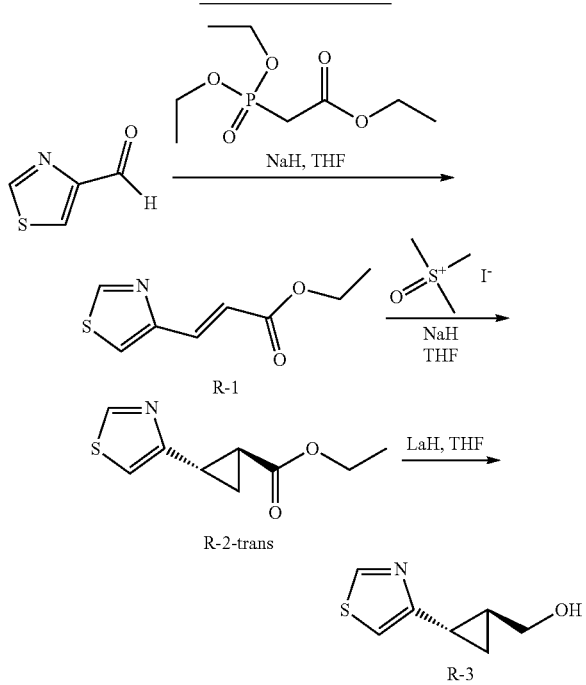

(E)-ethyl 3-(thiazol-4-yl)acrylate (R-1)

The title compound was prepared from thiazole-4-carbaldehyde according to the protocol outlined in Scheme N to afford R-2. LRMS (ES) (M+H)+: observed=184.1, calculated=184.2.

ethyl 2-(thiazol-4-yl)cyclopropanecarboxylate (R-2-trans)

The title compound was prepared from R-1 according to the protocol outlined in Scheme C, carried through as the trans racemate without chiral resolution, to afford R-2-trans. LRMS (ES) (M+H)+: observed=198.1, calculated=198.2.

2-(thiazol-4-yl)cyclopropyl)methanol (R-3)

The title compound was prepared from R-2-trans according to the protocol outlined in Scheme A to afford R-3. LRMS (ES) (M+H)+: observed=156.1, calculated=156.2.

REACTION SCHEME S

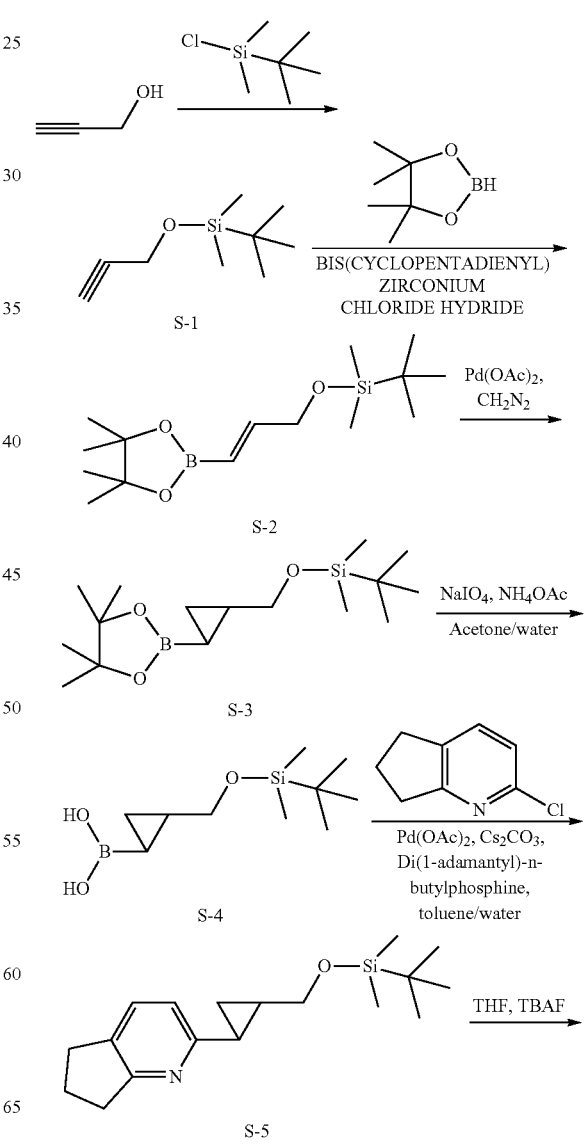

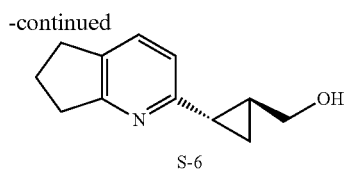

tert-butyldimethyl(prop-2-ynyloxy)silane (S-1)

To a mixture of prop-2-yn-1-ol (168 g, 3 mol), Et$_3$N (412 g, 4.08 mol) in CH$_2$Cl$_2$ (3500 mL) was added a solution of TBSCl (543 g, 3.45 mol) in CH$_2$Cl$_2$ (500 mL) at 0° C. Then the reaction mixture was warmed up to room temperature and stirred overnight. The mixture was washed by water (3000 mL), dried over Na$_2$SO$_4$, and concentrated to give crude product, which was purified by flash chromatography (petroleum ether) and distillation to give compound S-1 as a yellow liquid. (110 g, 43%)

(E)-tert-butyldimethyl(3-(4,4,5,5-tetramethyl-1,3,2-dioxaborolan-2-yl)allyloxy)silane (S-2)

The mixture of bis(cyclopentadienyl)zirconium chloride hydride (16.2 g, 0.062 mol), pinacolborane (160.5 g, 1.25 mol) and TEA (8.7 mL, 0.062 mol) in THF (1200 mL) was heated to 50° C. for 10 min and compound S-1 (106 g, 0.62 mol) was added. Then the mixture was stirred at 50° C. overnight. The reaction mixture was cooled, quenched with water and concentrated to remove majority of THF. The residue was extracted with ethyl acetate (2000 mL). The organic layer was washed with brine, dried over anhydrous Na$_2$SO$_4$ and concentrated in vacuum to give the crude product, which was purified by flash chromatography (petroleum ether) to afford compound S-2 as yellow liquid. (139 g, 74.7%)

tert-butyldimethyl((2-(4,4,5,5-tetramethyl-1,3,2-dioxaborolan-2-yl)cyclopropyl)methoxy)silane (S-3)

To a mixture of compound S-2 (65 g, 0.218 mol) and Pd(OAc)$_2$ (5 g, 0.0218 mol) in THF (200 mL) was added a solution of CH$_3$N$_2$ (fresh, 2.18 mol) in ether (1200 mL) at −78° C. Then the reaction mixture was warmed up to room temperature and stirred overnight. The mixture was filtered and the filtrate was concentrated to give crude product, which was purified by flash chromatography (petroleum ether) to afford compound S-3 as yellow oil. (27.5 g, 40%)

2-((tert-butyldimethylsilyloxy)methyl)cyclopropylboronic acid (S-4)

To a mixture of compound S-3 (36 g, 0.115 mol) in acetone (360 mL) and water (180 mL) was added NaIO$_4$ (148 g, 0.69 mol) and NaOAc (53.2 g, 0.69 mol) at room temperature. Then reaction mixture was stirred at 25° C. overnight. The mixture was filtered and the filtrate was concentrated to remove acetone, extracted with ethyl acetate (600 mL). The organic layer was washed by water, brine, dried over Na$_2$SO$_4$, and concentrated to give crude product, which was purified by chromatography (petroleum ether/ethyl acetate=10:1 to 4:1 and then MeOH/CH$_2$Cl$_2$=25:1) to give S-4 as yellow liquid. (19.3, 73%)

2-(2-((tert-butyldimethylsilyloxy)methyl)cyclopropyl)-6,7-dihydro-5H-cyclopenta[b]pyridine (S-5)

To a stirred solution of S-4 (3.0 g, 13.0 mol) in toluene (50 mL) was added 2-chloro-6,7-dihydro-5H-cyclopenta[b]pyridine (2.0 g, 13.0 mmol), palladium acetate (0.29 g, 1.30 mmol), di(1-adamantyl)-n-butylphosphine (1.40 g, 3.91 mmol), cesium carbonate (12.74 g, 39.10 mmol) and water (16.6 mL). The resulting mixture was heated to 100° C. overnight. The reaction was partitioned between ethyl acetate and saturated sodium bicarbonate solution. The organic phase was concentrated and flash column separation using a 0-10% ethyl acetate/hexane gradient gave S-5 as an oil. (3.19 g, 65%)

((1S,2S)-2-(6,7-dihydro-5H-cyclopenta[b]pyridin-2-yl)cyclopropyl)methanol (S-6)

To a stirred solution of S-5 (3.19 g, 10.5 mmol) in THF (40 mL) was added tetrabutyl ammonium fluoride solution 1M (10.5 mL, 10.5 mmol). The resulting mixture was stirred 2 hours at room temperature and concentrated. Flash column separation using a 10-100% ethyl acetate/hexane gradient gave S-6 as an oil. (1.44 g, 72%)

EXAMPLE 1

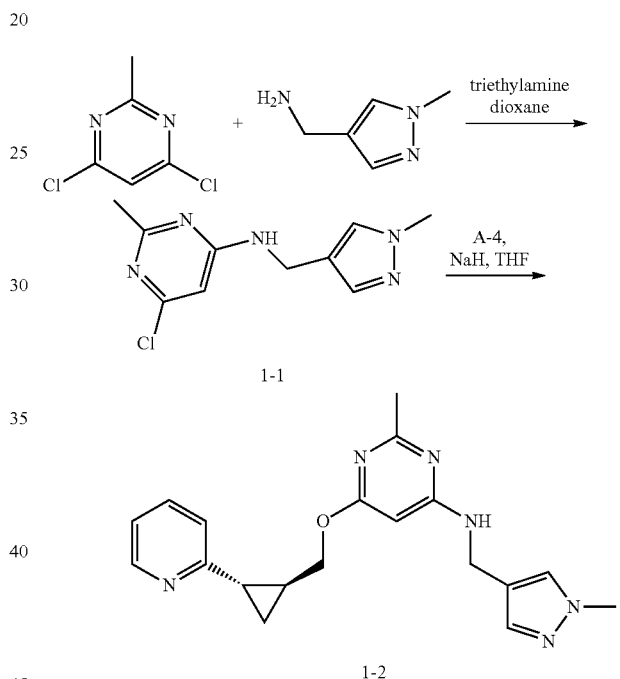

6-chloro-2-methyl-N-((1-methyl-1H-pyrazol-4-yl)methyl)pyrimidin-4-amine (1-1)

To a stirred solution of 4,6-dichloro-2-methylpyrimidine (100 mg, 0.61 mmol) in dioxane (1 mL) was added triethylamine (0.3 mL, 2.15 mmol) and (1-methyl-1H-pyrazol-4-yl)methanamine (68 mg, 0.61 mmol). The resulting mixture was microwave irradiated at 150° C. for 30 minutes. The reaction was diluted with ethyl acetate and washed with saturated sodium bicarbonate solution. The organic phase was concentrated and flash column separation using a 10-100% ethyl acetate/hexane gradient gave 1-1 as a white solid (121 mg, 83%). MS (M+H)$^+$: observed=238.0857, calculated=238.0854.

2-methyl-N-[(1-methyl-1H-pyrazol-4-yl)methyl]-6-[(2-pyridin-2-ylcyclopropyl)methoxy]pyrimidin-4-amine (1-2)

To a stirred solution of A-4 (188 mg, 1.26 mmol) in THF (2.5 mL) was added sodium hydride 60% dispersion (74 mg, 1.85 mmol) and the resulting solution was stirred at room temperature for 20 minutes. To this was added 1-1 (200 mg, 0.84 mmol) and the resulting mixture was microwave irradiated at 100° C. for 90 minutes. The reaction was concentrated and purified using reverse phase chromatography (10-30%, 0.1% TFA in H$_2$O/acetonitrile) to give 1-2 as a white solid (231 mg, 78%). MS (M+H)$^+$: observed=351.1927, calculated=351.1928.

EXAMPLE 2

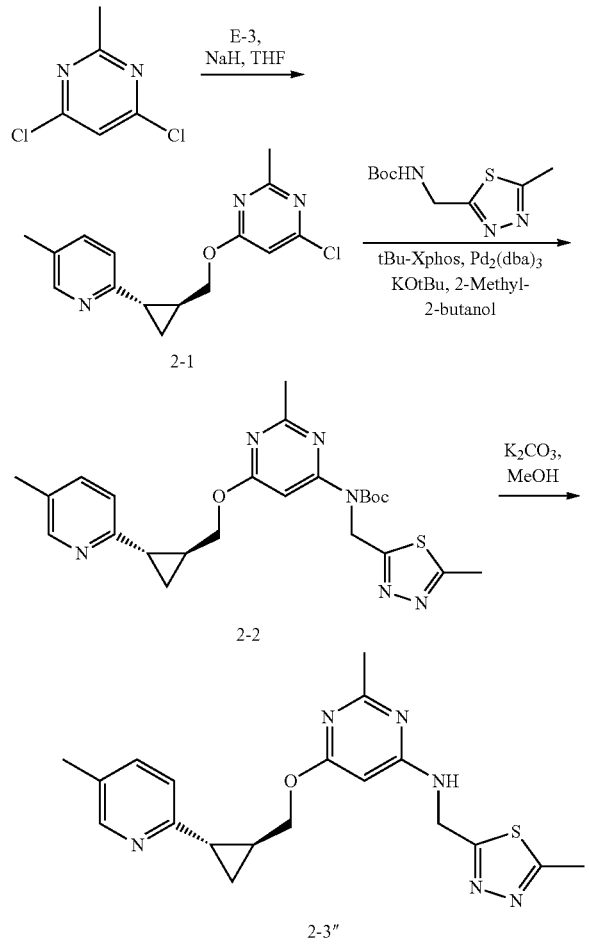

4-Chloro-2-methyl-6-(((1S,2S)-2-(5-methylpyridin-2-yl)cyclopropyl)methoxy)-pyrimidine (2-1)

To a suspension of sodium hydride (103 mg, 2.57 mmol) in THF (6.0 mL) was added (S,S) E-3 (350 mg, 2.14 mmol). The resulting mixture was stirred for 30 min before 4,6-dichloro-2-methylpyridine (419 mg, 2.57 mmol) was added. After heating at 80° C. for 1 hour, the reaction was diluted with ethyl acetate and washed with water and brine. The organic phase was concentrated and flash column chromatography using a 0-40% ethyl acetate/hexane gradient gave 2-1 as a colorless oil (453 mg, 73%). MS (M+H)$^+$: observed=290.35, calculated=290.10.

tert-Butyl ((5-methyl-1,3,4-thiadiazol-2-yl)methyl) (2-methyl-6-(((1S,2S)-2-(5-methylpyridin-2-yl)cyclopropyl)methoxy)pyrimidin-4-yl)carbamate (2-2)

A solution of 2-1 (100 mg, 0.35 mmol), tert-butyl ((5-methyl-1,3,4-thiadiazol-2-yl)methyl)carbamate (119 mg, 0.52 mmol; for preparation, see D. C. Pryde et al. *J. Med. Chem.* 2006, 49, 4409-4424), 1 M potassium tert-butoxide (1.03 mL in THF) and 2-di-tert-butylphosphino-2',4',6'-triisopropylbiphenyl (14.6 mg, 0.035 mmol) in 2-Methyl-2-butanol (1.7 ml) was purged with N$_2$ for 5 min. Tris(dibenzylideneacetone)-dipalladium(0) (31.6 mg, 0.035 mmol) was added and the mixture was heated at 60° C. for 1 hour. The reaction was cooled to room temperature and diluted with ethyl acetate and sat. NaHCO$_3$. The organic phase was washed with water, brine and concentrated. The residue was purified by flash column chromatography using a 20-60% ethyl acetate/hexane gradient gave 2-2 as a colorless oil (117 mg, 70%). MS (M+H)$^+$: observed=483.10, calculated=483.21.

2-Methyl-6-{[(1S,2S)-2-(5-methylpyridin-2-yl)cyclopropyl]methoxy}-N-[(5-methyl-1,3,4-thiadiazol-2-yl)methyl]pyrimidin-4-amine (2-3")

To a solution of 2-2 (51.0 mg, 0.11 mmol) in MeOH (0.53 mL) was added K$_2$CO$_3$ (17.5 mg, 0.13 mmol). The resulted suspension was stirred at 70° C. for 2 hour. The mixture was diluted with EtOAc, and then extracted with 1N HCl. The aqueous layer was basified with 5N NaOH and extracted with DCM three times. The combined DCM layers were dried over Na$_2$SO$_4$ and concentrated to give 2-3" as an off white solid (29 mg, 72%). MS (M+H)$^+$: observed=383.1654, calculated=383.1649. $^1$H NMR (400 MHz, DMSO-d$_6$): δ 8.22 (s, 1H), 7.82 (br t, J=5.0 Hz, 1H), 7.45 (d, J=7.9 Hz, 1H), 7.17 (d, J=7.7 Hz, 1H), 5.64 (s, 1H), 4.76 (d, J=5.0 Hz, 2H), 4.23 (m, 1H), 4.14 (m, 1H), 2.65 (s, 3H), 2.31 (s, 3H), 2.22 (s, 3H), 2.09 (m, 1H), 1.71 (m, 1H), 1.12 (m, 1H), 0.98 (m, 1H)

TABLE 1

The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.

| Cpd | Structure | Name | HRMS/LRMS |
|---|---|---|---|
| 2-3 | 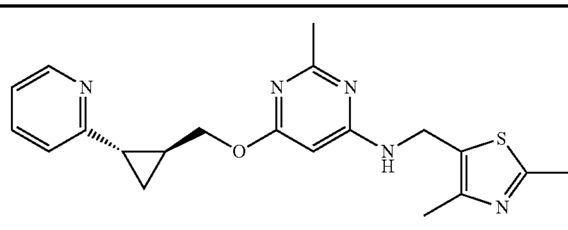 | S,S-N-[(2,4-dimethyl-1,3-thiazol-5-yl)methyl]-2-methyl-6-[(2-pyridin-2-ylcyclopropyl)methoxy]pyrimidin-4-amine | C20H23N5OS [M + H] calc 382.1696 obs 382.1700 |

TABLE 1-continued

*The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.*

| Cpd | Structure | Name | HRMS/LRMS |
|---|---|---|---|
| 2-4 | 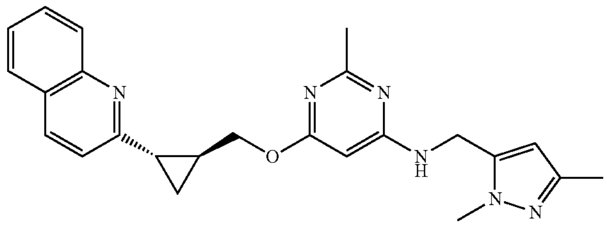 [SMILES: Cc1cc(CNc2cc(OC[C@H]3C[C@@H]3c3ccc4ccccc4n3)nc(C)n2)n(C)n1] | S,S-N-[(1,3-dimethyl-1H-pyrazol-5-yl)methyl]-2-methyl-6-[(2-quinolin-2-ylcyclopropyl)methoxy]pyrimidin-4-amine | C24H26N6O [M + H] calc 415.2241 obs 415.2242 |
| 2-5 | 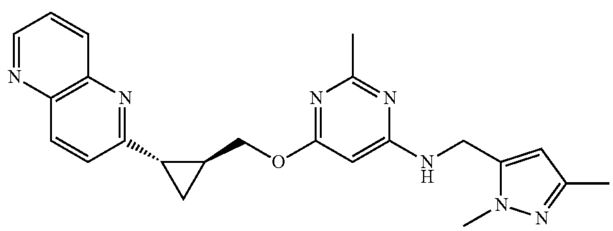 [SMILES: Cc1cc(CNc2cc(OC[C@H]3C[C@@H]3c3ccc4ncccc4n3)nc(C)n2)n(C)n1] | S,S-N-[(1,3-dimethyl-1H-pyrazol-5-yl)methyl]-2-methyl-6-{[2-(1,5-naphthyridin-2-yl)cyclopropyl]methoxy}pyrimidin-4-amine | C23H25N7O [M + H] calc 416.2193 obs 416.2192 |
| 2-6 | 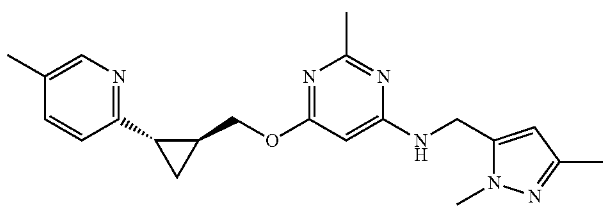 | S,S-N-[(1,3-dimethyl-1H-pyrazol-5-yl)methyl]-2-methyl-6-{[2-(5-methylpyridin-2-yl)cyclopropyl]methoxy}pyrimidin-4-amine | C21H26N6O [M + H] calc 379.2241 obs 379.2244 |
| 2-7 | 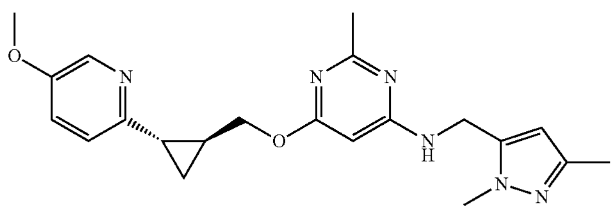 [SMILES: COc1ccc([C@H]2C[C@@H]2COc2cc(NCc3cc(C)nn3C)nc(C)n2)nc1] | S,S-N-[(1,3-dimethyl-1H-pyrazol-5-yl)methyl]-6-{[2-(5-methoxypyridin-2-yl)cyclopropyl]methoxy}-2-methylpyrimidin-4-amine | C21H26N6O2 [M + H] calc 395.2190 obs 395.2191 |
| 2-8 | 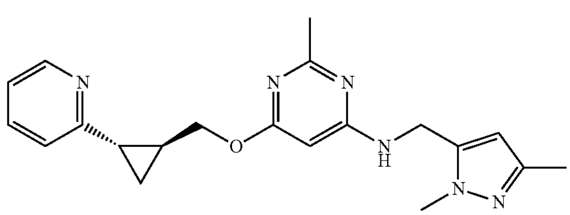 [SMILES: Cc1cc(CNc2cc(OC[C@H]3C[C@@H]3c3ccccn3)nc(C)n2)n(C)n1] | S,S-N-[(1,3-dimethyl-1H-pyrazol-5-yl)methyl]-2-methyl-6-[(-2-pyridin-2-ylcyclopropyl)-methoxy]pyrimidin-4-amine | C20H24N6O [M + H] calc 365.2084 obs 365.2092 |
| 2-9 | 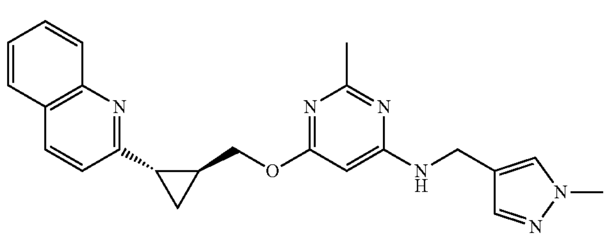 [SMILES: Cc1nc(NCc2cnn(C)c2)cc(OC[C@H]2C[C@@H]2c2ccc3ccccc3n2)n1] | S,S-2-methyl-N-[(1-methyl-1H-pyrazol-4-yl)methyl]-6-[(2-quinolin-2-ylcyclopropyl)methoxy]pyrimidin-4-amine | C23H24N6O [M + H] calc 401.2084 obs 401.2066 |

TABLE 1-continued

*The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.*

| Cpd | Structure | Name | HRMS/LRMS |
|---|---|---|---|
| 2-10 | 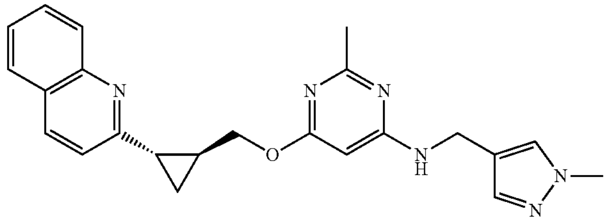 [SMILES: Cc1nc(NCc2cnn(C)c2)cc(OC[C@H]2C[C@@H]2c2ccc3ccccc3n2)n1] | S,S-2-methyl-N-[(1-methyl-1H-pyrazol-4-yl)methyl]-6-[(2-quinolin-2-ylcyclopropyl)methoxy]pyrimidin-4-amine | C23H24N6O [M + H] calc 401.2084 obs 401.2088 |
| 2-11 | 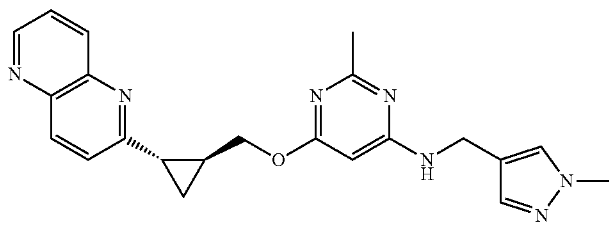 [SMILES: Cc1nc(NCc2cnn(C)c2)cc(OC[C@H]2C[C@@H]2c2ccc3ncccc3n2)n1] | S,S-2-methyl-N-[(1-methyl-1H-pyrazol-4-yl)methyl]-6-{[2-(1,5-naphthyridin-2-yl)cyclopropyl]methoxy}pyrimidin-4-amine | C22H23N7O [M + H] calc 402.2037 obs 402.2040 |
| 2-12 | 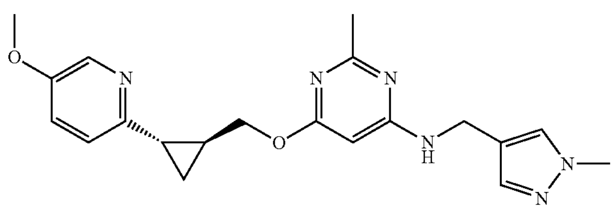 [SMILES: COc1ccc([C@H]2C[C@@H]2COc2cc(NCc3cnn(C)c3)nc(C)n2)nc1] | S,S-6-{[2-(5-methoxypyridin-2-yl)cyclopropyl]methoxy}-2-methyl-N-[(1-methyl-1H-pyrazol-4-yl)methyl]pyrimidin-4-amine | C20H24N6O2 [M + H] calc 381.2034 obs 381.2039 |
| 2-13 | 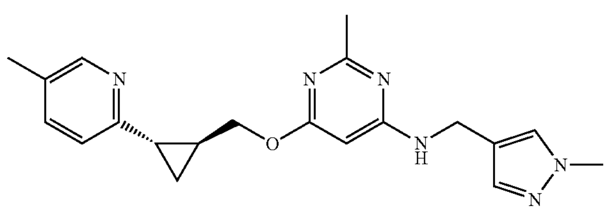 | S,S-2-methyl-N-[(1-methyl-1H-pyrazol-4-yl)methyl]-6-{[-2-(5-methylpyridin-2-yl)cyclopropyl]methoxy}pyrimidin-4-amine | C20H24N6O [M + H] calc 365.2084 obs 365.2091 |
| 2-14 | 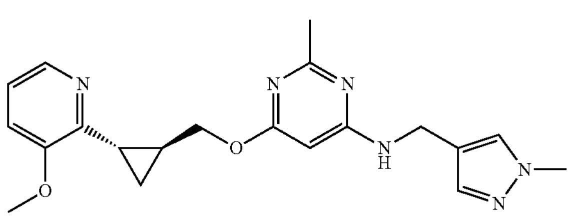 [SMILES: COc1cccnc1[C@H]1C[C@@H]1COc1cc(NCc2cnn(C)c2)nc(C)n1] | 6-{[2-(3-methoxypyridin-2-yl)cyclopropyl]methoxy}-2-methyl-N-[(1-methyl-1H-pyrazol-4-yl)methyl]pyrimidin-4-amine | C20H24N6O2 [M + H] calc 381.2034 obs 381.2040 |
| 2-15 | 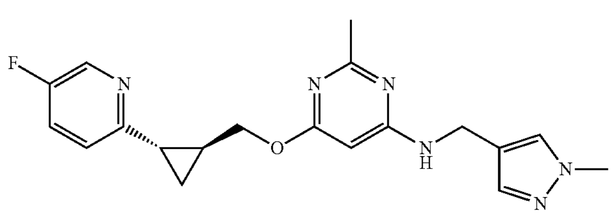 [SMILES: Cc1nc(NCc2cnn(C)c2)cc(OC[C@H]2C[C@@H]2c2ccc(F)cn2)n1] | S,S-6-{[2-(5-fluoropyridin-2-yl)cyclopropyl]methoxy}-2-methyl-N-[(1-methyl-1H-pyrazol-4-yl)methyl]pyrimidin-4-amine | C19H21FN6O [M + H] calc 369.1834 obs 369.1830 |

TABLE 1-continued

*The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.*

| Cpd | Structure | Name | HRMS/LRMS |
|---|---|---|---|
| 2-16 | 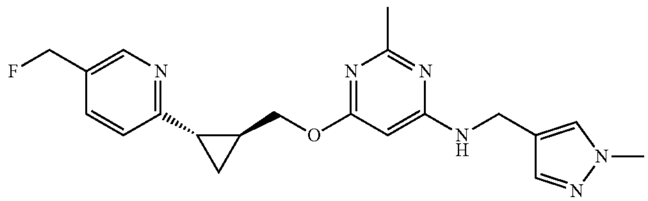 [SMILES: Cc1nc(NCc2cnn(C)c2)cc(OC[C@H]2C[C@@H]2c2ccc(CF)cn2)n1] | 6-({2-[5-(fluoromethyl)pyridin-2-yl]cyclopropyl}methoxy)-2-methyl-N-[(1-methyl-1H-pyrazol-4-yl)methyl]pyrimidin-4-amine | C20H23FN6O [M + H] calc 383.1990 obs 383.1988 |
| 2-17 | 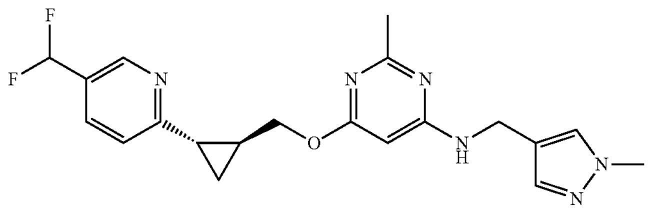 [SMILES: Cc1nc(NCc2cnn(C)c2)cc(OC[C@H]2C[C@@H]2c2ccc(C(F)F)cn2)n1] | 6-({2-[5-(difluoromethyl)pyridin-2-yl]cyclopropyl}methoxy)-2-methyl-N-[(1-methyl-1H-pyrazol-4-yl)methyl]pyrimidin-4-amine | C20H22F2N6O [M + H] calc 401.1896 obs 401.1893 |
| 2-18 | 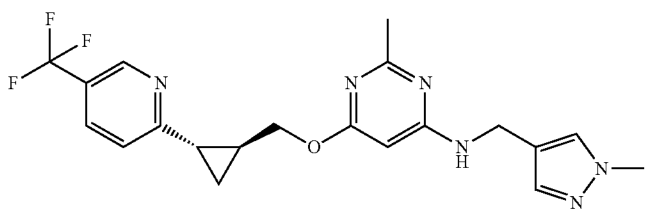 [SMILES: Cc1nc(NCc2cnn(C)c2)cc(OC[C@H]2C[C@@H]2c2ccc(C(F)(F)F)cn2)n1] | 2-methyl-N-[(1-methyl-1H-pyrazol-4-yl)methyl]-6-({2-[5-(trifluoromethyl)pyridin-2-yl]cyclopropyl}methoxy)pyrimidin-4-amine | C20H21F3N6O [M + H] calc 419.1802 obs 419.1805 |
| 2-19 | 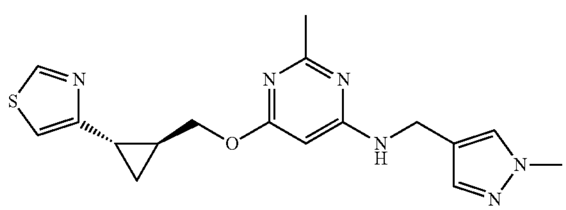 [SMILES: Cc1nc(NCc2cnn(C)c2)cc(OC[C@H]2C[C@@H]2c2cscn2)n1] | 2-methyl-N-[(1-methyl-1H-pyrazol-4-yl)methyl]-6-{[2-(1,3-thiazol-4-yl)cyclopropyl]methoxy}pyrimidin-4-amine | C17H20N6OS [M + H] calc 357.1495 obs |
| 2-20 | 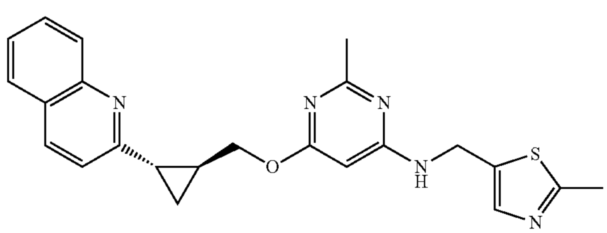 [SMILES: Cc1nc(NCc2cnc(C)s2)cc(OC[C@H]2C[C@@H]2c2ccc3ccccc3n2)n1] | S,S-2-methyl-N-[(2-methyl-1,3-thiazol-5-yl)methyl]-6-[(2-quinolin-2-ylcyclopropyl)methoxy]pyrimidin-4-amine | C23H23N5OS [M + H] calc 418.1696 obs 418.1677 |
| 2-21 | 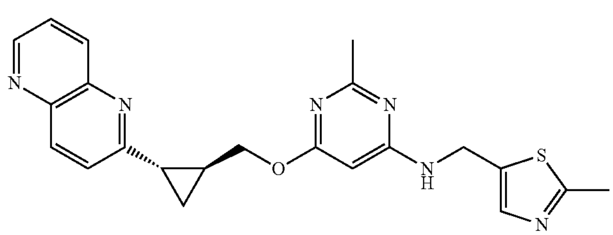 [SMILES: Cc1nc(NCc2cnc(C)s2)cc(OC[C@H]2C[C@@H]2c2ccc3ncccc3n2)n1] | S,S-2-methyl-N-[(2-methyl-1,3-thiazol-5-yl)methyl]-6-{[2-(1,5-naphthyridin-2-yl)cyclopropyl]methoxy}pyrimidin-4-amine | C22H22N6OS [M + H] calc 419.1649 obs 419.1628 |

TABLE 1-continued

*The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.*

| Cpd | Structure | Name | HRMS/LRMS |
|---|---|---|---|
| 2-22 | 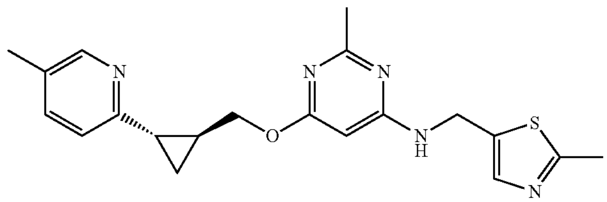 | S,S-2-methyl-6-{[2-(5-methylpyridin-2-yl)cyclopropyl]methoxy}-N-[(2-methyl-1,3-thiazol-5-yl)methyl]pyrimidin-4-amine | C20H23N5OS [M + H] calc 382.1696 obs 382.1680 |
| 2-23 | 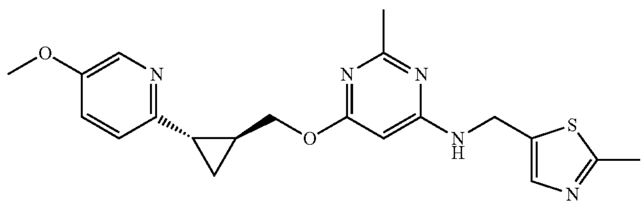 | S,S-6-{[2-(5-methoxypyridin-2-yl)cyclopropyl]methoxy}-2-methyl-N-[(2-methyl-1,3-thiazol-5-yl)methyl]pyrimidin-4-amine | C20H23N5O2S [M + H] calc 398.1645 obs 398.1628 |
| 2-24 | 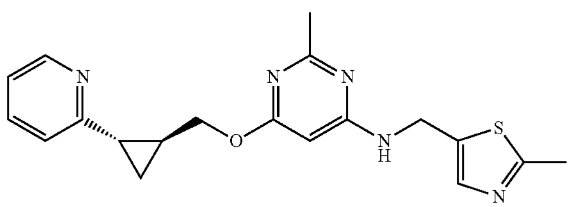 | S,S-2-methyl-N-[(2-methyl-1,3-thiazol-5-yl)methyl]-6-[(2-pyridin-2-ylcyclopropyl)methoxy]pyrimidin-4-amine | C19H21N5OS [M + H] calc 368.1540 obs 368.1526 |
| 2-25 | 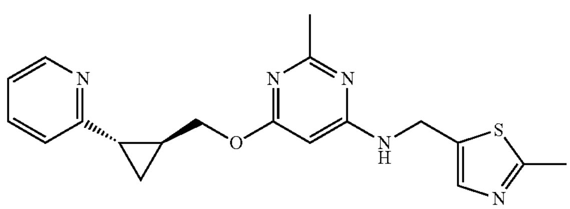 [SMILES: Cc1nc(NCc2cnc(C)s2)cc(OC[C@H]2C[C@@H]2c2ccccn2)n1] | S,S-2-methyl-N-[(2-methyl-1,3-thiazol-5-yl)methyl]-6-[(2-pyridin-2-ylcyclopropyl)methoxy]pyrimidin-4-amine | C19H21N5OS [M + H] calc 368.1540 obs 368.1545 |
| 2-26 | 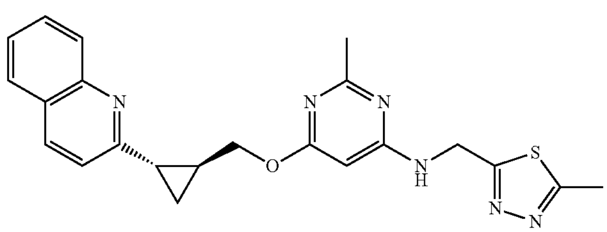 [SMILES: Cc1nc(NCc2nnc(C)s2)cc(OC[C@H]2C[C@@H]2c2ccc3ccccc3n2)n1] | S,S-2-methyl-N-[(5-methyl-1,3,4-thiadiazol-2-yl)methyl]-6-[(2-quinolin-2-ylcyclopropyl)methoxy]pyrimidin-4-amine | C22H22N6OS [M + H] calc 419.1649 obs 419.1630 |
| 2-27 | 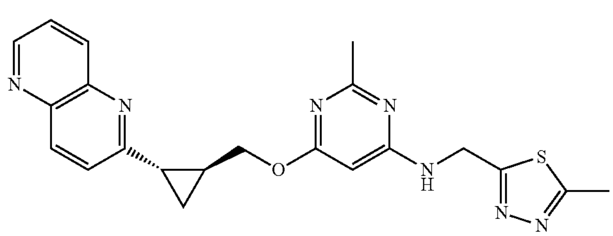 [SMILES: Cc1nc(NCc2nnc(C)s2)cc(OC[C@H]2C[C@@H]2c2ccc3ncccc3n2)n1] | S,S-2-methyl-N-[(5-methyl-1,3,4-thiadiazol-2-yl)methyl]-6-{[2-(1,5-naphthyridin-2-yl)cyclopropyl]methoxy}pyrimidin-4-amine | C21H21N7OS [M + H] calc 420.1601 obs 420.1602 |

TABLE 1-continued

The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.

| Cpd | Structure | Name | HRMS/LRMS |
|---|---|---|---|
| 2-28 | 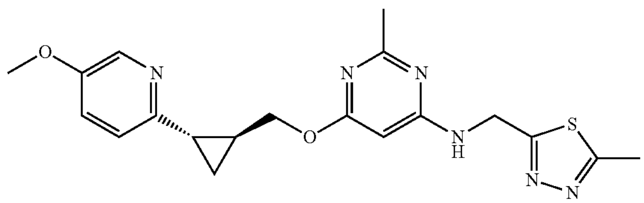 | S,S-6-{[2-(5-methoxypyridin-2-yl)cyclopropyl]methoxy}-2-methyl-N-[(5-methyl-1,3,4-thiadiazol-2-yl)methyl]pyrimidin-4-amine | C19H22N6O2S [M + H] calc 399.1598 obs 399.1586 |
| 2-29 | 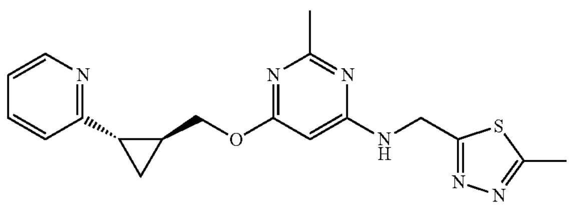 [SMILES: Cc1nc(NCc2nnc(C)s2)cc(OC[C@H]2C[C@@H]2c2ccccn2)n1] | S,S-2-methyl-N-[(5-methyl-1,3,4-thiadiazol-2-yl)methyl]-6-[(2-pyridin-2-ylcyclopropyl)methoxy]pyrimidin-4-amine | C18H20N6OS [M + H] calc 369.1492 obs 369.1493 |
| 2-30 | 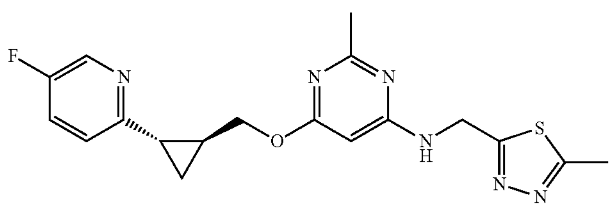 [SMILES: Cc1nc(NCc2nnc(C)s2)cc(OC[C@H]2C[C@@H]2c2ccc(F)cn2)n1] | S,S-6-{[2-(5-fluoropyridin-2-yl)cyclopropyl]methoxy}-2-methyl-N-[(5-methyl-1,3,4-thiadiazol-2-yl)methyl]pyrimidin-4-amine | C18H19FN6OS [M + H] calc 387.1398 obs 387.1393 |
| 2-31 | 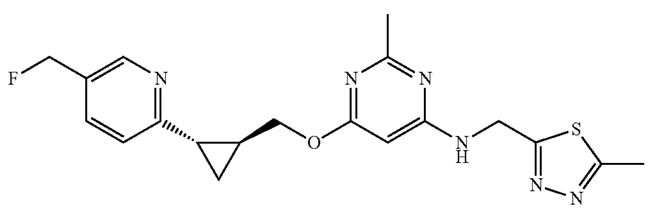 [SMILES: Cc1nc(NCc2nnc(C)s2)cc(OC[C@H]2C[C@@H]2c2ccc(CF)cn2)n1] | 6-({2-[5-(fluoromethyl)pyridin-2-yl]cyclopropyl}methoxy)-2-methyl-N-[(5-methyl-1,3,4-thiadiazol-2-yl)methyl]pyrimidin-4-amine | C19H21FN6OS [M + H] calc 401.1554 obs 401.1553 |
| 2-32 | 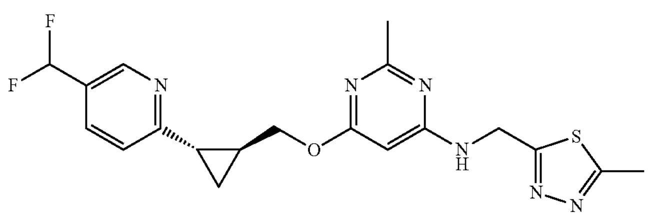 [SMILES: Cc1nc(NCc2nnc(C)s2)cc(OC[C@H]2C[C@@H]2c2ccc(C(F)F)cn2)n1] | 6-({2-[5-(difluoromethyl)pyridin-2-yl]cyclopropyl}methoxy)-2-methyl-N-[(5-methyl-1,3,4-thiadiazol-2-yl)methyl]pyrimidin-4-amine | C19H20F2N6OS [M + H] calc 419.1460 obs 419.1455 |
| 2-33 | 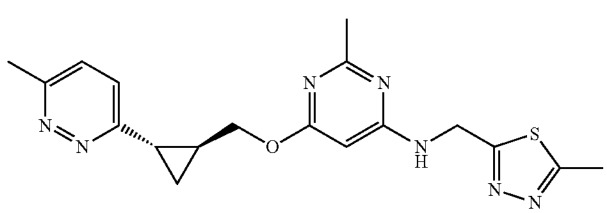 | 2-methyl-6-{[2-(6-methylpyridazin-3-yl)cyclopropyl]methoxy}-N-[(5-methyl-1,3,4-thiadiazol-2-yl)methyl]pyrimidin-4-amine | C18H21N7OS [M + H] calc 384.1601 obs 384.1614 |
| 2-34 | 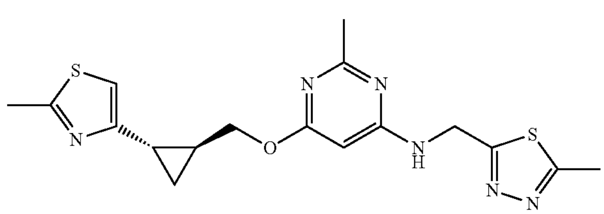 | S,S-2-methyl-N-[(5-methyl-1,3,4-thiadiazol-2-yl)methyl]-6-{[2-(2-methyl-1,3-thiazol-4-yl)cyclopropyl]methoxy}pyrimidin-4-amine | C17H20N6OS2 [M + H] calc 389.1213 obs 389.1213 |

TABLE 1-continued

The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.

| Cpd | Structure | Name | HRMS/LRMS |
|---|---|---|---|
| 2-35 | 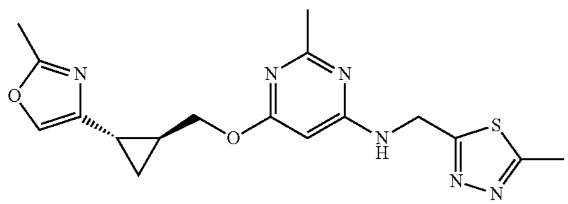 [SMILES: Cc1nc(NCc2nnc(C)s2)cc(OC[C@H]2C[C@@H]2c2coc(C)n2)n1] | 2-methyl-6-{[2-(2-methyl-1,3-oxazol-4-yl)cyclopropyl]methoxy}-N-[(5-methyl-1,3,4-thiadiazol-2-yl)methyl]pyrimidin-4-amine | C17H20N6O2S [M + H] calc 373.1441 obs 373.1440 |
| 2-36 | 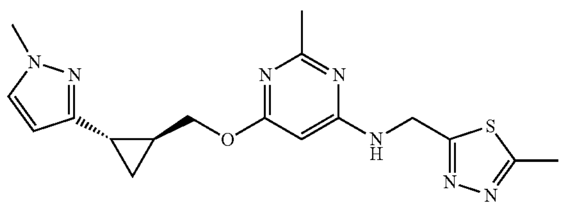 [SMILES: Cc1nc(NCc2nnc(C)s2)cc(OC[C@H]2C[C@@H]2c2ccn(C)n2)n1] | 2-methyl-6-{[2-(1-methyl-1H-pyrazol-3-yl)cyclopropyl]methoxy}-N-[(5-methyl-1,3,4-thiadiazol-2-yl)methyl]pyrimidin-4-amine | C17H21N7OS [M + H] calc 372.1601 obs 372.1592 |
| 2-37 | 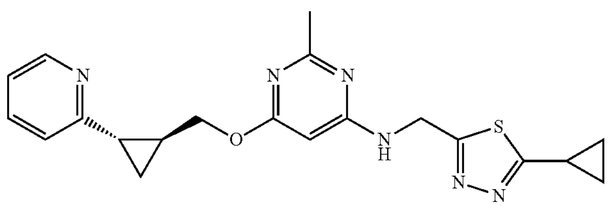 [SMILES: Cc1nc(NCc2nnc(C3CC3)s2)cc(OC[C@H]2C[C@@H]2c2ccccn2)n1] | S,S-N-[(5-cyclopropyl-1,3,4-thiadiazol-2-yl)methyl]-2-methyl-6-[(2-pyridin-2-ylcyclopropyl)methoxy]pyrimidin-4-amine | C20H22N6OS [M + H] calc 395.1649 obs 395.1651 |
| 2-38 | 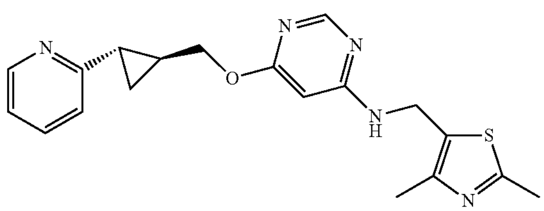 [SMILES: Cc1nc(C)c(CNc2cc(OC[C@H]3C[C@@H]3c3ccccn3)ncn2)s1] | S,S-N-[(2,4-dimethyl-1,3-thiazol-5-yl)methyl]-6-[(2-pyridin-2-ylcyclopropyl)methoxy]pyrimidin-4-amine | C19H21N5OS [M + H] calc 368.1540 obs 368.1545 |
| 2-39 | 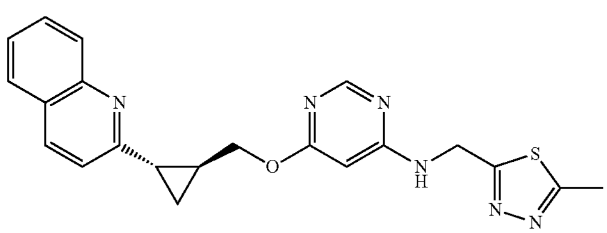 [SMILES: Cc1nnc(CNc2cc(OC[C@H]3C[C@@H]3c3ccc4ccccc4n3)ncn2)s1] | S,S-N-[(5-methyl-1,3,4-thiadiazol-2-yl)methyl]-6-[(2-quinolin-2-ylcyclopropyl)methoxy]pyrimidin-4-amine | C21H20N6OS [M + H] calc 405.1492 obs 405.1476 |
| 2-40 | 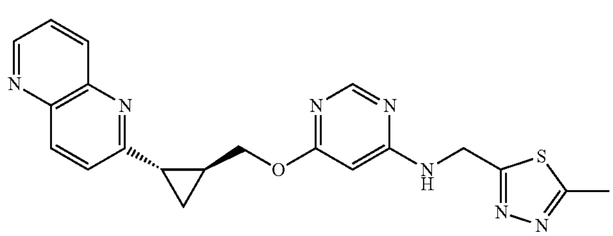 | S,S-N-[(5-methyl-1,3,4-thiadiazol-2-yl)methyl]-6-{[2-(1,5-naphthyridin-2-yl)cyclopropyl]methoxy}pyrimidin-4-amine | C20H19N7OS [M + H] calc 406.1445 obs 406.1433 |
| 2-41 | 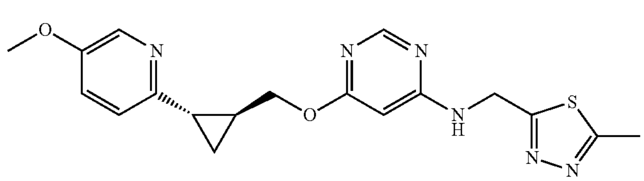 | S,S-6-{[2-(5-methoxypyridin-2-yl)cyclopropyl]methoxy}-N-[(5-methyl-1,3,4-thiadiazol-2-yl)methyl]pyrimidin-4-amine | C18H20N6O2S [M + H] calc 385.1441 obs 385.1423 |

TABLE 1-continued

The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.

| Cpd | Structure | Name | HRMS/LRMS |
|---|---|---|---|
| 2-42 | 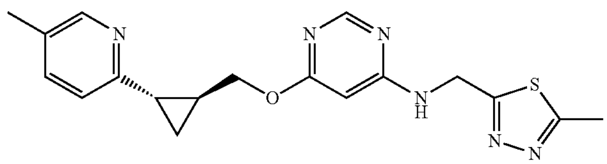 | S,S-6-{[2-(5-methylpyridin-2-yl)cyclopropyl]methoxy}-N-[(5-methyl-1,3,4-thiadiazol-2-yl)methyl]pyrimidin-4-amine | C18H20N6OS [M + H] calc 369.1492 obs 369.1477 |
| 2-43 | 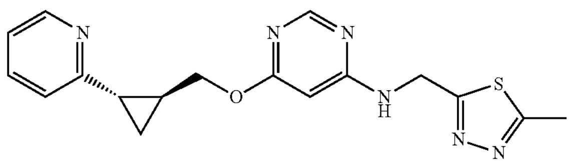 [SMILES: Cc1nnc(CNc2cc(OC[C@H]3C[C@@H]3c3ccccn3)ncn2)s1] | S,S-N-[(5-methyl-1,3,4-thiadiazol-2-yl)methyl]-6-[(2-pyridin-2-ylcyclopropyl)methoxy]pyrimidin-4-amine | C17H18N6OS [M + H] calc 355.1336 obs 355.1324 |
| 2-44 | 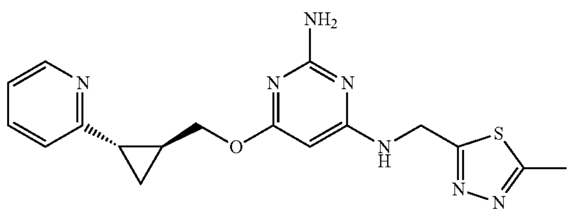 [SMILES: Cc1nnc(CNc2cc(OC[C@H]3C[C@@H]3c3ccccn3)nc(N)n2)s1] | S,S-N-4-[(5-methyl-1,3,4-thiadiazol-2-yl)methyl]-6-[(2-pyridin-2-ylcyclopropyl)methoxy]pyrimidine-2,4-diamine | C17H19N7OS [M + H] calc 370.1445 obs 370.1455 |
| 2-45 | 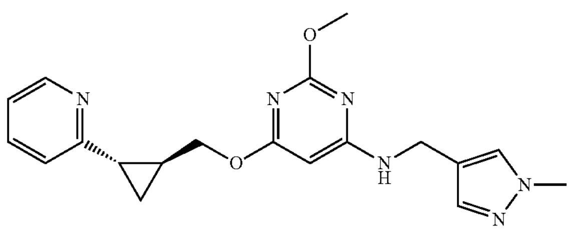 [SMILES: COc1nc(NCc2cnn(C)c2)cc(OC[C@H]2C[C@@H]2c2ccccn2)n1] | S,S-2-methoxy-N-[(1-methyl-1H-pyrazol-4-yl)methyl]-6-[(2-pyridin-2-ylcyclopropyl)methoxy]pyrimidin-4-amine | C19H22N6O2 [M + H] calc 367.1877 obs 367.1859 |
| 2-46 | 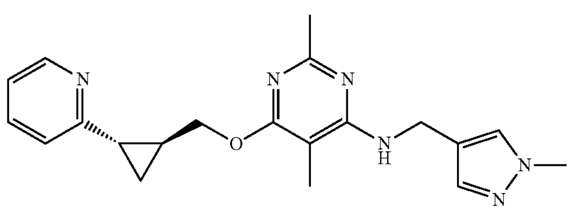 [SMILES: Cc1nc(NCc2cnn(C)c2)c(C)c(OC[C@H]2C[C@@H]2c2ccccn2)n1] | S,S-2,5-dimethyl-N-[(1-methyl-1H-pyrazol-4-yl)methyl]-6-[(2-pyridin-2-ylcyclopropyl)methoxy]pyrimidin-4-amine | C20H24N6O [M + H] calc 365.2084 obs 365.2090 |
| 2-47 | 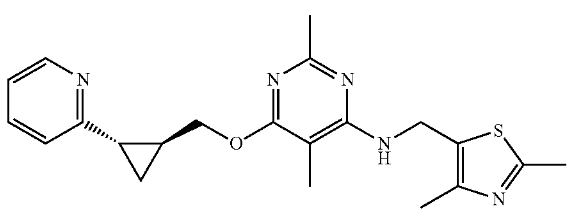 [SMILES: Cc1nc(NCc2sc(C)nc2C)c(C)c(OC[C@H]2C[C@@H]2c2ccccn2)n1] | S,S-N-[(2,4-dimethyl-1,3-thiazol-5-yl)methyl]-2,5-dimethyl-6-[(2-pyridin-2-ylcyclopropyl)methoxy]pyrimidin-4-amine | C21H25N5OS [M + H] calc 396.1853 obs 396.1858 |
| 2-48 | 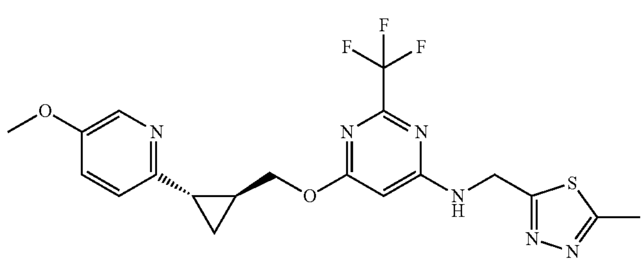 | S,S-N-6-{[2-(5-methoxypyridin-2-yl)cyclopropyl]methoxy}-N-[(5-methyl-1,3,4-thiadiazol-2-yl)methyl]-2-(trifluoromethyl)-pyrimidin-4-amine | C19H19F3N6O2S [M + H] calc 453.1315 obs 453.1309 |

TABLE 1-continued

*The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.*

| Cpd | Structure | Name | HRMS/LRMS |
|---|---|---|---|
| 2-49 | 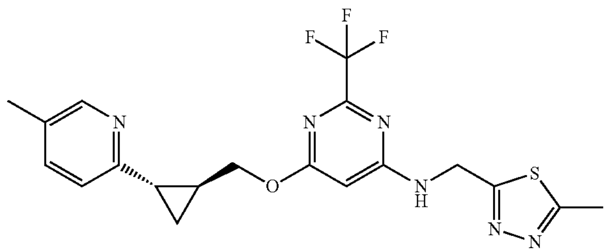 | S,S-N-6-{[2-(5-methylpyridin-2-yl)cyclopropyl]methoxy}-N-[(5-methyl-1,3,4-thiadiazol-2-yl)methyl]-2-(trifluoromethyl)-pyrimidin-4-amine | C19H19F3N6OS [M + H] calc 437.1366 obs 437.1360 |
| 2-50 | 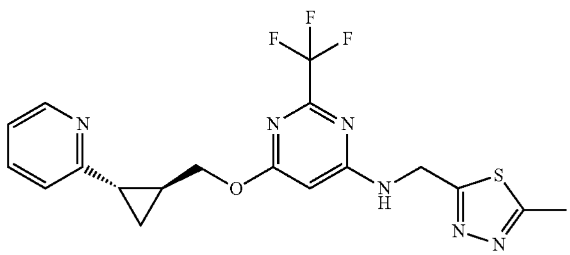 [SMILES: Cc1nnc(CNc2cc(OC[C@H]3C[C@@H]3c3ccccn3)nc(C(F)(F)F)n2)s1] | S,S-N-[(5-methyl-1,3,4-thiadiazol-2-yl)methyl]-6-[(2-pyridin-2-ylcyclopropyl)methoxy]-2-(trifluoromethyl)-pyrimidin-4-amine | C18H17F3N6OS [M + H] calc 423.1209 obs 423.1207 |
| 2-51 | 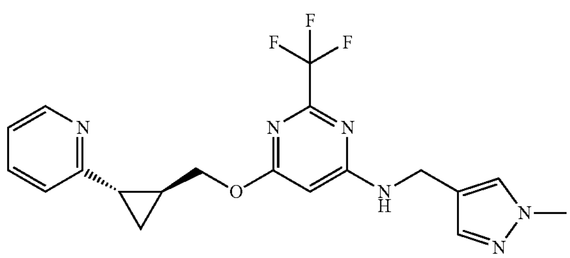 [SMILES: Cn1cc(CNc2cc(OC[C@H]3C[C@@H]3c3ccccn3)nc(C(F)(F)F)n2)cn1] | S,S-N-[(1-methyl-1H-pyrazol-4-yl)methyl]-6-[(2-pyridin-2-ylcyclopropyl)methoxy]-2-(trifluoromethyl)-pyrimidin-4-amine | C19H19F3N6O [M + H] calc 405.1645 obs 405.1626 |
| 2-52 | 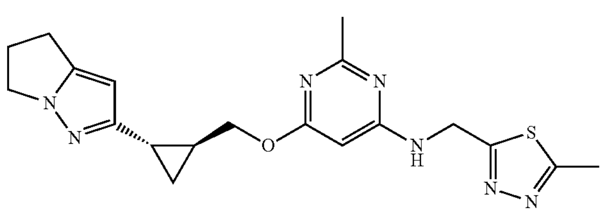 [SMILES: Cc1nc(NCc2nnc(C)s2)cc(OC[C@H]2C[C@@H]2c2cc3n(n2)CCC3)n1] | 6-{[(1S,2S)-2-(5,6-dihydro-4H-pyrrolo[1,2-b]pyrazol-2-yl)cyclopropyl]methoxy}-2-methyl-N-[(5-methyl-1,3,4-thiadiazol-2-yl)methyl]pyrimidin-4-amine | C19H23N7OS [M + H] calc 398.1758 obs 398.1757 |
| 2-53 | 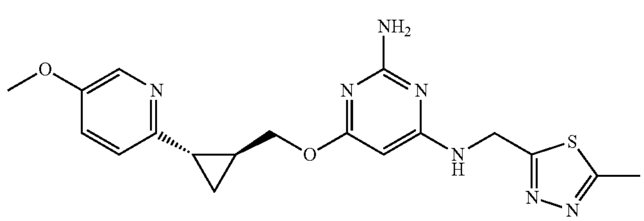 | S,S-6-{[(1S,2S)-2-(5-methoxypyridin-2-yl)cyclopropyl]methoxy}-N-4-[(5-methyl-1,3,4-thiadiazol-2-yl)methyl]pyrimidine-2,4-diamine | C18H21N7O2S [M + H] calc 400.1550 obs 400.1546 |
| 2-54 | 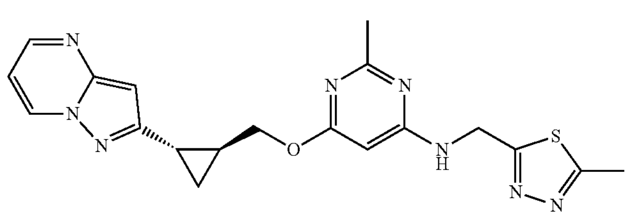 [SMILES: Cc1nc(NCc2nnc(C)s2)cc(OC[C@H]2C[C@@H]2c2cc3ncccn3n2)n1] | 2-methyl-N-[(5-methyl-1,3,4-thiadiazol-2-yl)methyl]-6-{[(1S,2S)-2-pyrazolo[1,5-a]pyrimidin-2-ylcyclopropyl]methoxy}pyrimidin-4-amine | C19H20N8OS [M + H] calc 409.1554 obs 409.1545 |

TABLE 1-continued

The following compounds were prepared in an analogous manner to Examples 1 and 2, using an appropriately substituted 4,6-dichloropyrimidine, amine, and alcohols previously described in Schemes A through R. Starting materials not previously illustrated were commercially available, described in the literature, or readily synthesized by one skilled in the art of organic synthesis without undue experimentation.

| Cpd | Structure | Name | HRMS/LRMS |
|---|---|---|---|
| 2-55 | 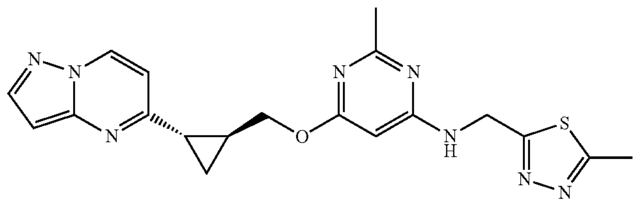 [SMILES: Cc1nc(NCc2nnc(C)s2)cc(OC[C@H]2C[C@@H]2c2ccn3nccc3n2)n1] | 2-methyl-N-[(5-methyl-1,3,4-thiadiazol-2-yl)methyl]-6-{[(1S,2S)-2-pyrazolo[1,5-a]pyrimidin-5-ylcyclopropyl]methoxy}pyrimidin-4-amine | C19H20N8OS [M + H] calc 409.1554 obs 409.1545 |
| 2-56 | 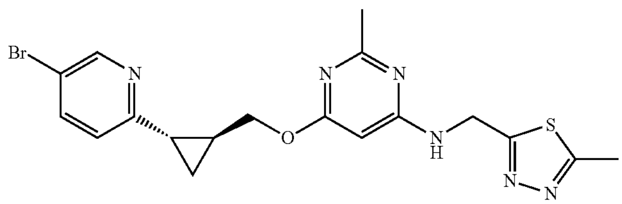 [SMILES: Cc1nc(NCc2nnc(C)s2)cc(OC[C@H]2C[C@@H]2c2ccc(Br)cn2)n1] | S,S-6-{[(1S,2S)-2-(5-bromopyridin-2-yl)cyclopropyl]methoxy}-2-methyl-N-[(5-methyl-1,3,4-thiadiazol-2-yl)methyl]pyrimidin-4-amine | C18H19BrN6OS [M + H] calc 447.0597 obs 447.0593 |
| 2-57 | 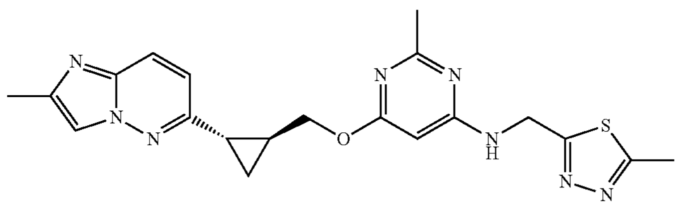 | 2-methyl-6-{[(1S,2S)-2-(2-methylimidazo[1,2-b]pyridazin-6-yl)cyclopropyl]methoxy}-N-[(5-methyl-1,3,4-thiadiazol-2-yl)methyl]pyrimidin-4-amine | C20H22N8OS [M + H] calc 423.1710 obs 423.1717 |
| 2-58 | 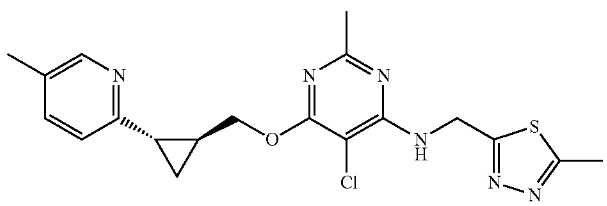 | S,S-5-chloro-2-methyl-6-{[(1S,2S)-2-(5-methylpyridin-2-yl)cyclopropyl]methoxy}-N-[(5-methyl-1,3,4-thiadiazol-2-yl)methyl]pyrimidin-4-amine | C19H21ClN6OS [M + H] calc 417.1259 obs 417.1268 |

EXAMPLE 3

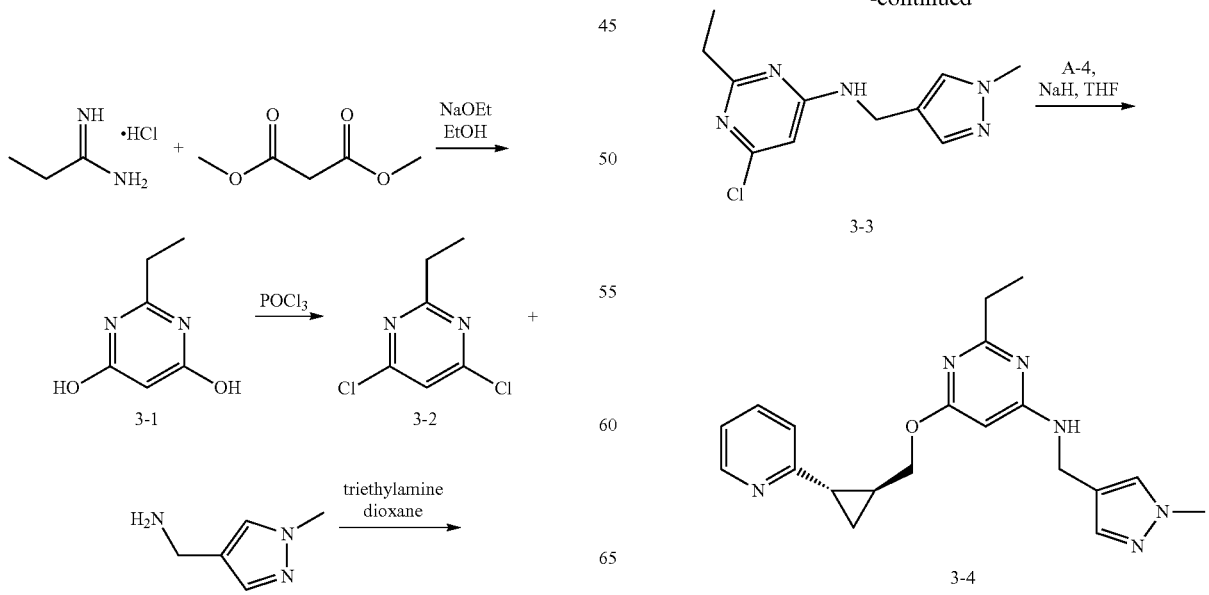

4,6-dichloro-2-ethylpyrimidine 3-2

To a stirred solution of propionimidamide hydrochloride (1.00 g, 9.21 mmol) in ethanol (35 mL) was added sodium ethoxide solution 21% in ethanol (17.25 mL). The resulting solution was stirred 20 minutes at room temperature. To this was added dimethyl malonate (0.97 g, 7.37 mmol) and the resulting solution was heated to 80° C. for 5 hours.

The solution was allowed to cool and concentrated to dryness. To this solid was added a minimum amount of water and neutralized to pH of 5 using 6N HCl solution. The solution was allowed to sit overnight during which time white solid 3-1 precipitated out. The solid 3-1 was dissolved in phosphorus oxychloride (5 mL) and heated to reflux for 90 minutes. The solution was concentrated, quenched with ice, and partitioned between ethyl acetate and a saturated sodium bicarbonate solution. The organic phase was concentrated to give 3-2 as an oil (0.60 g, 37%). LRMS (M+H)$^+$: observed=177.1, calculated=177.0.

6-chloro-2-ethyl-N-((1-methyl-1H-pyrazol-4-yl)methyl)pyrimidin-4-amine 3-3

The title compound was prepared from 2-2 according to the protocol outlined in Example 1, to afford 3-3 as a solid. LRMS (ES) (M+H)$^+$: observed=252.1, calculated=252.7.

2-ethyl-N-[(1-methyl-1H-pyrazol-4-yl)methyl]-6-[(2-pyridin-2-ylcyclopropyl)methoxy]pyrimidin-4-amine 3-4

The title compound was prepared from 3-3 according to the protocol outlined in Example 1, to afford 3-4 as a solid. HRMS (ES) (M+H)$^+$: observed=365.2090, calculated=365.2084.

TABLE 2

The following compounds were prepared in an analogous manner to Example 3, using an appropriately substituted dimethylmalonate, imidamide, and alcohols previously described in Schemes A through R.

| Cpd. | Structure | Name | HRMS/LRMS |
|---|---|---|---|
| 3-5 | 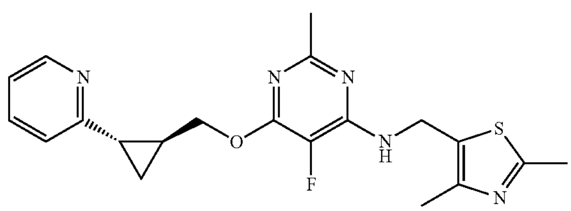 | S,S-N-[(2,4-dimethyl-1,3-thiazol-5-yl)methyl]-5-fluoro-2-methyl-6-[(2-pyridin-2-ylcyclopropyl)methoxy]pyrimidin-4-amine | C20H22FN5OS [M + H] calc 400.1602 obs 400.1608 |
| 3-6 | 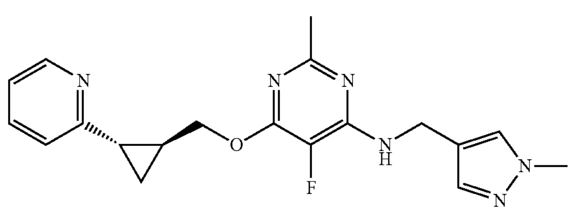 | S,S-5-fluoro-2-methyl-N-[(1-methyl-1H-pyrazol-4-yl)methyl]-6-[(-2-pyridin-2-ylcyclopropyl)methoxy]pyrimidin-4-amine | C19H21FN6O [M + H] calc 369.1834 obs 369.1840 |
| 3-7 | 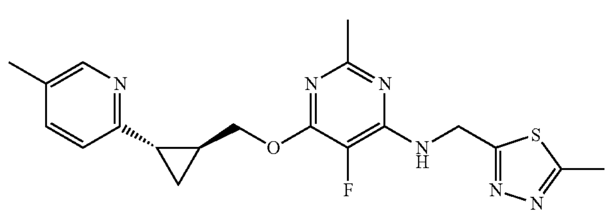 | S,S-5-fluoro-2-methyl-6-{[2-(5-methylpyridin-2-yl)cyclopropyl]methoxy}-N-[(5-methyl-1,3,4-thiadiazol-2-yl)methyl]pyrimidin-4-amine | C19H21FN6OS [M + H] calc 401.1554 obs 401.1556 |
| 3-8 | 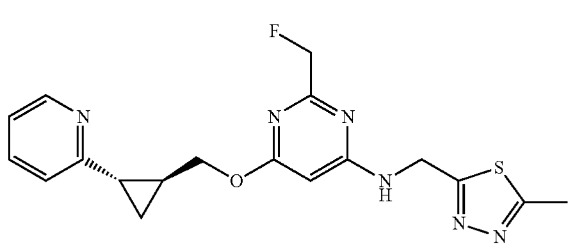 [SMILES: Cc1nnc(CNc2cc(OC[C@H]3C[C@@H]3c3ccccn3)nc(CF)n2)s1] | S,S-2-(fluoromethyl)-N-[(5-methyl-1,3,4-thiadiazol-2-yl)methyl]-6-[(2-pyridin-2-ylcyclopropyl)methoxy]pyrimidin-4-amine | C18H19FN6OS [M + H] calc 387.1398 obs 387.1396 |

TABLE 2-continued

The following compounds were prepared in an analogous manner to Example 3,
using an appropriately substituted dimethylmalonate, imidamide, and alcohols previously
described in Schemes A through R.

| Cpd. | Structure | Name | HRMS/LRMS |
| --- | --- | --- | --- |
| 3-9 | 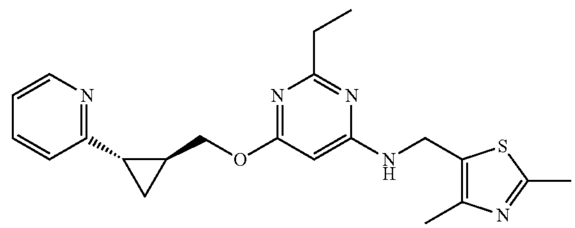 [SMILES: CCc1nc(NCc2sc(C)nc2C)cc(OC[C@H]2C[C@@H]2c2ccccn2)n1] | S,S-N-[(2,4-dimethyl-1,3-thiazol-5-yl)methyl]-2-ethyl-6-[(2-pyridin-2-ylcyclopropyl)methoxy]pyrimidin-4-amine | C21H25N5OS [M + H] calc 396.1853 obs 396.1858 |
| 3-10 | 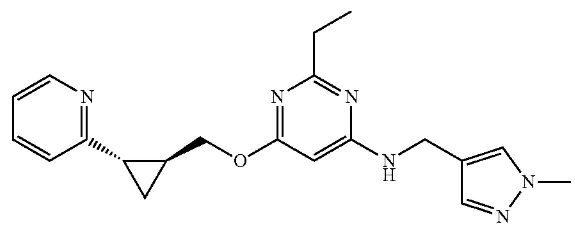 [SMILES: CCc1nc(NCc2cnn(C)c2)cc(OC[C@H]2C[C@@H]2c2ccccn2)n1] | S,S-2-ethyl-N-[(1-methyl-1H-pyrazol-4-yl)methyl]-6-[(2-pyridin-2-ylcyclopropyl)methoxy]pyrimidin-4-amine | C20H24N6O [M + H] calc 365.2084 obs 365.2090 |
| 3-11 | 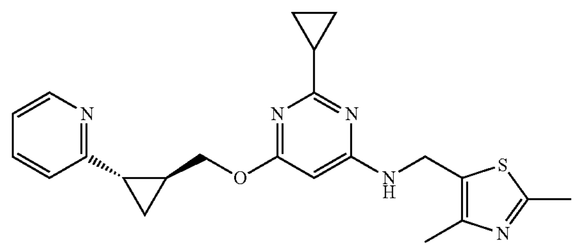 [SMILES: Cc1nc(C)c(CNc2cc(OC[C@H]3C[C@@H]3c3ccccn3)nc(C3CC3)n2)s1] | S,S-2-cyclopropyl-N-[(2,4-dimethyl-1,3-thiazol-5-yl)methyl]-6-[(2-pyridin-2-ylcyclopropyl)methoxy]pyrimidin-4-amine | C22H25N5OS [M + H] calc 408.1853 obs 408.1859 |
| 3-12 | 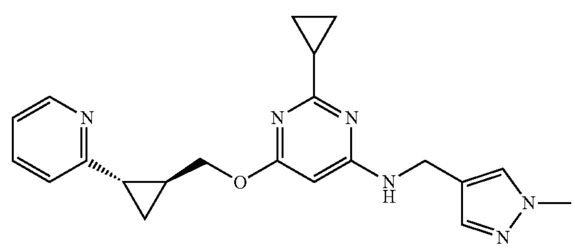 [SMILES: Cn1cc(CNc2cc(OC[C@H]3C[C@@H]3c3ccccn3)nc(C3CC3)n2)cn1] | S,S-2-cyclopropyl-N-[(1-methyl-1H-pyrazol-4-yl)methyl]-6-[(2-pyridin-2-ylcyclopropyl)methoxy]pyrimidin-4-amine | C21H24N6O [M + H] calc 377.2084 obs 377.2089 |
| 3-13 | 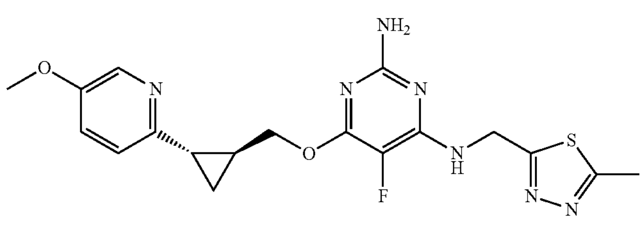 | 5-fluoro-6-{[(1S,2S)-2-(5-methoxypyridin-2-yl)cyclopropyl]methoxy}-N-4-[(5-methyl-1,3,4-thiadiazol-2-yl)methyl]pyrimidine-2,4-diamine | C18H20FN7O2S [M + H] calc 418.1456 obs 418.1447 |
| 3-14 | 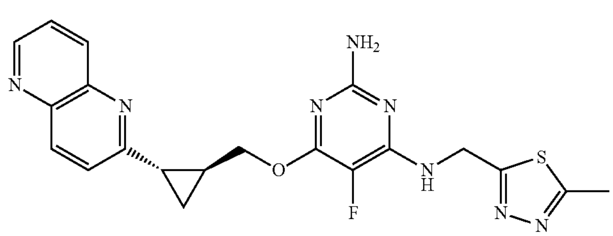 [SMILES: Cc1nnc(CNc2nc(N)nc(OC[C@H]3C[C@@H]3c3ccc4ncccc4n3)c2F)s1] | 5-fluoro-N-4-[(5-methyl-1,3,4-thiadiazol-2-yl)methyl]-6-{[(1S,2S)-2-(1,5-naphthyridin-2-yl)cyclopropyl]methoxy}pyrimidine-2,4-diamine | C20H19FN8OS [M + H] calc 439.1459 obs 439.1455 |

TABLE 2-continued

The following compounds were prepared in an analogous manner to Example 3,
using an appropriately substituted dimethylmalonate, imidamide, and alcohols previously
described in Schemes A through R.

| Cpd. | Structure | Name | HRMS/LRMS |
|---|---|---|---|
| 3-15 | 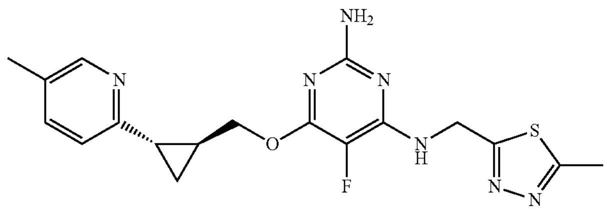 | 5-fluoro-6-{[(1S,2S)-2-(5-methylpyridin-2-yl)cyclopropyl]methoxy}-N-4-[(5-methyl-1,3,4-thiadiazol-2-yl)methyl]pyrimidine-2,4-diamine | C18H20FN7OS [M + H] calc 402.1507 obs 402.1494 |
| 3-16 | 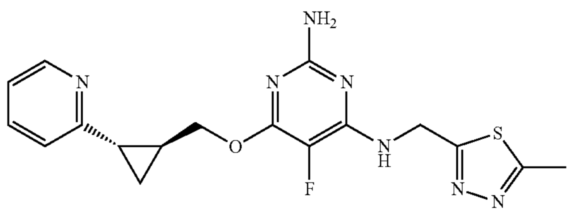 [SMILES: Cc1nnc(CNc2nc(N)nc(OC[C@H]3C[C@@H]3c3ccccn3)c2F)s1] | 5-fluoro-N-4-[(5-methyl-1,3,4-thiadiazol-2-yl)methyl]-6-{[(1S,2S)-2-pyridin-2-ylcyclopropyl]methoxy}pyrimidine-2,4-diamine | C17H18FN7OS [M + H] calc 388.1350 obs 388.1346 |
| 3-17 | 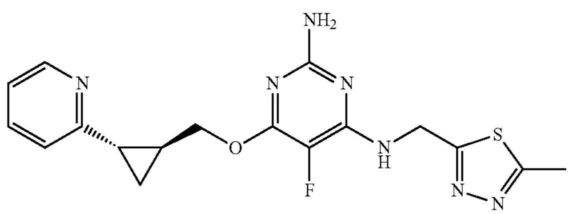 [SMILES: Cc1nnc(CNc2nc(N)nc(OC[C@H]3C[C@@H]3c3ccccn3)c2F)s1] | 5-fluoro-N-4-[(5-methyl-1,3,4-thiadiazol-2-yl)methyl]-6-{[(1S,2S)-2-pyridin-2-ylcyclopropyl]methoxy}pyrimidine-2,4-diamine | C17H18FN7OS [M + H] calc 388.1350 obs 388.1346 |
| 3-18 | 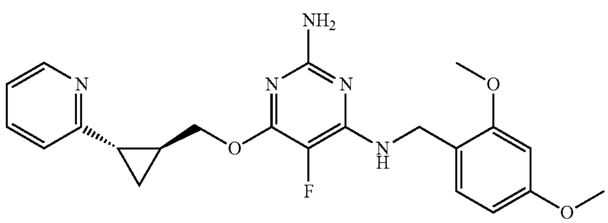 [SMILES: COc1ccc(CNc2nc(N)nc(OC[C@H]3C[C@@H]3c3ccccn3)c2F)c(OC)c1] | N-4-(2,4-dimethoxybenzyl)-5-fluoro-6-{[(1S,2S)-2-pyridin-2-ylcyclopropyl]methoxy}pyrimidine-2,4-diamine | C22H24FN5O3 [M + H] calc 426.1936 obs 426.1919 |
| 3-19 | 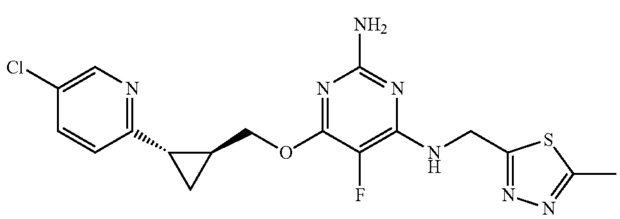 [SMILES: Cc1nnc(CNc2nc(N)nc(OC[C@H]3C[C@@H]3c3ccc(Cl)cn3)c2F)s1] | 6-{[(1S,2S)-2-(5-chloropyridin-2-yl)cyclopropyl]methoxy}-5-fluoro-N-4-[(5-methyl-1,3,4-thiadiazol-2-yl)methyl]pyrimidine-2,4-diamine | C17H17ClFN7OS [M + H] calc 422.0961 obs 422.0946 |
| 3-20 | 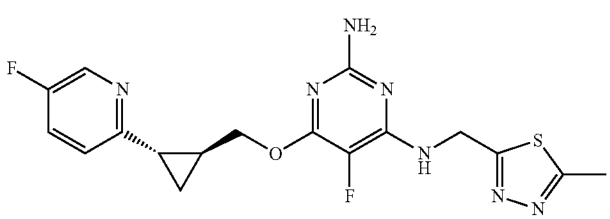 [SMILES: Cc1nnc(CNc2nc(N)nc(OC[C@H]3C[C@@H]3c3ccc(F)cn3)c2F)s1] | 5-fluoro-6-{[(1S,2S)-2-(5-fluoropyridin-2-yl)cyclopropyl]methoxy}-N-4-[(5-methyl-1,3,4-thiadiazol-2-yl)methyl]pyrimidine-2,4-diamine | C17H17F2N7OS [M + H] calc 406.1256 obs 406.1243 |
| 3-21 | 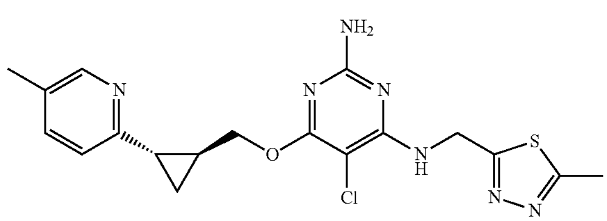 | 5-chloro-6-{[(1S,2S)-2-(5-methylpyridin-2-yl)cyclopropyl]methoxy}-N-[(5-methyl-1,3,4-thiadiazol-2-yl)methyl]pyrimidine-2,4-diamine | C18H20ClN7OS [M + H] calc 418.1211 obs 418.1195 |

TABLE 2-continued

The following compounds were prepared in an analogous manner to Example 3,
using an appropriately substituted dimethylmalonate, imidamide, and alcohols previously
described in Schemes A through R.

| Cpd. | Structure | Name | HRMS/LRMS |
|---|---|---|---|
| 3-22 | 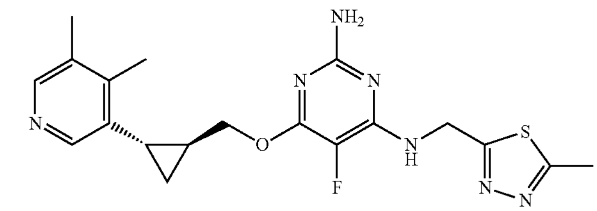 [SMILES: Cc1nnc(CNc2nc(N)nc(OC[C@H]3C[C@@H]3c3cncc(C)c3C)c2F)s1] | 6-{[(1S,2S)-2-(4,5-dimethylpyridin-2-yl)cyclopropyl]methoxy}-N-[(5-methyl-1,3,4-thiadiazol-2-yl)methyl]pyrimidine-2,4-diamine | C19H22FN7OS [M + H] calc 416.1663 obs 416.1664 |
| 3-23 | 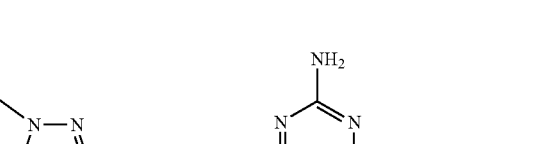 | 6-(((1S,2S)-2-(5,6-dihydro-4H-pyrrolo[1,2-b]pyrazol-2-yl)cyclopropyl)methoxy)-5-fluoro-N4-((5-methyl-1,3,4-thiadiazol-2-yl)methyl)pyrimidine-2,4-diamine | C18H21FN8OS [M + H] calc 417.1616 obs 417.1619 |
| 3-24 | 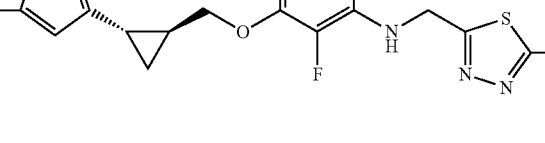 | 5-fluoro-N4-((5-methyl-1,3,4-thiadiazol-2-yl)methyl)-6-(((1S,2S)-2-(6-methylpyridin-2-yl)cyclopropyl)methoxy)pyrimidine-2,4-diamine | C18H20FN7OS [M + H] calc 402.1507 obs 402.1507 |
| 3-25 | 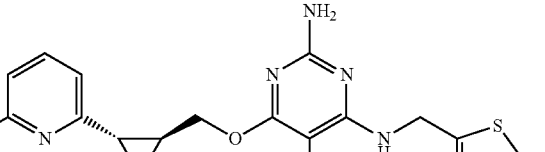 | S,S-6-(((1S,2S)-2-(6,7-dihydro-5H-cyclopenta[b]pyridin-2-yl)cyclopropyl)methoxy)-5-fluoro-N4-((5-methyl-1,3,4-thiadiazol-2-yl)methyl)pyrimidine-2,4-diamine | C20H22FN7OS [M + H] calc 428.1663 obs 428.1665 |

Starting materials not previously illustrated were commercially available, described in the literature, or readily synthesized by one skilled in the art of organic synthesis without undue experimentation.

EXAMPLE 3A

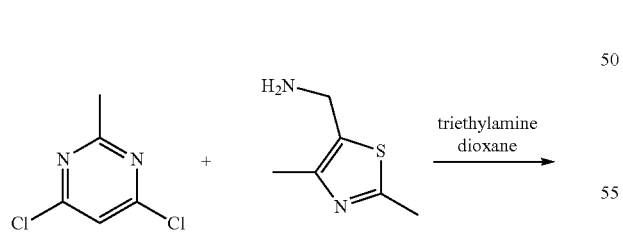

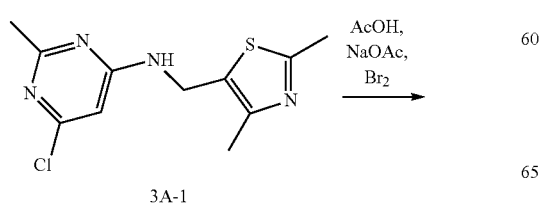

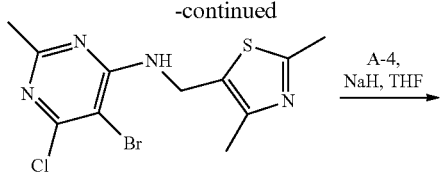

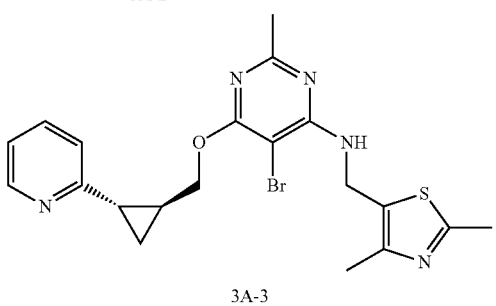

6-chloro-N-((2,4-dimethylthiazol-5-yl)methyl)-2-methylpyrimidin-4-amine 3A-1

The title compound was prepared from 4,6-dichloro-2-methylpyrimidine and (2,4-dimethylthiazol-5-yl)methanamine according to the protocol outlined in Example 1, to afford 3A-1 as a solid. LRMS (ES) (M+H)$^+$: observed=269.1, calculated=269.7.

5-bromo-6-chloro-N-((2,4-dimethylthiazol-5-yl)methyl)-2-methylpyrimidin-4-amine 3A-2

To a stirred solution of 3-1 (0.25 g, 0.93 mmol) in acetic acid (4 mL) was added sodium acetate (0.10 g, 1.21 mmol). To this solution was added bromine (0.05 mL, 1.02 mmol) dissolved in acetic acid (0.5 mL) dropwise. The resulting solution was stirred at room temperature for 30 minutes and concentrated. The residue was partitioned between ethyl acetate and a saturated sodium bicarbonate solution. The organic phase was concentrated and triturated in ether to give the title compound as a solid (0.28 g, 85%). LRMS (ES) (M+H)$^+$: observed=347.0/349.0, calculated=347.6/349.6.

5-bromo-N-((2,4-dimethylthiazol-5-yl)methyl)-2-methyl-6-(2-(pyridin-2-yl)cyclopropyl)methoxy)pyrimidin-4-amine 3A-3

The title compound was prepared from 3A-2 according to the protocol outlined in Example 1, to afford 3A-3 as a solid. HRMS (ES) (M+H)$^+$: observed=460.0814, calculated=460.0801.

EXAMPLE 4

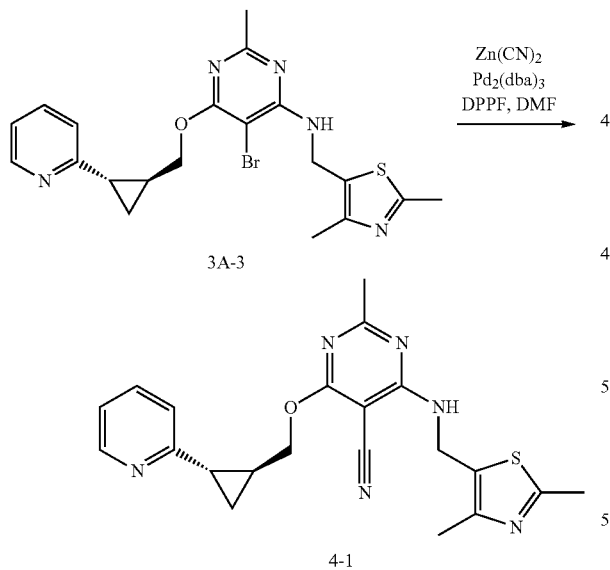

3A-3

4-1

4-((2,4-dimethylthiazol-5-yl)methylamino)-2-methyl-6-((2-(pyridin-2-yl)cyclopropyl)methoxy)pyrimidine-5-carbonitrile 4-1

To a stirred solution of 3A-3 (45 mg, 0.01 mmol), and zinc cyanide (6.9 mg, 0.06 mmol) in DMF (1 mL) under nitrogen was added Pd$_2$(dba)$_3$ (4.5 mg, 0.005 mmol) and DPPF (5.4 mg, 0.010 mmol) and the resulting mixture was heated to 120° C. for 3 days. The reaction was allowed to cool and partititioned between ethyl acetate and a saturated sodium bicarbonate solution. The organic phase was concentrated and purified using reverse phase chromatography (15-45%, 0.1% TFA in H$_2$O/acetonitrile) to give 4-1 as a solid (7.5 mg, 19%). HRMS (ES) (M+H)$^+$: observed=407.1650, calculated=407.1649.

EXAMPLE 5

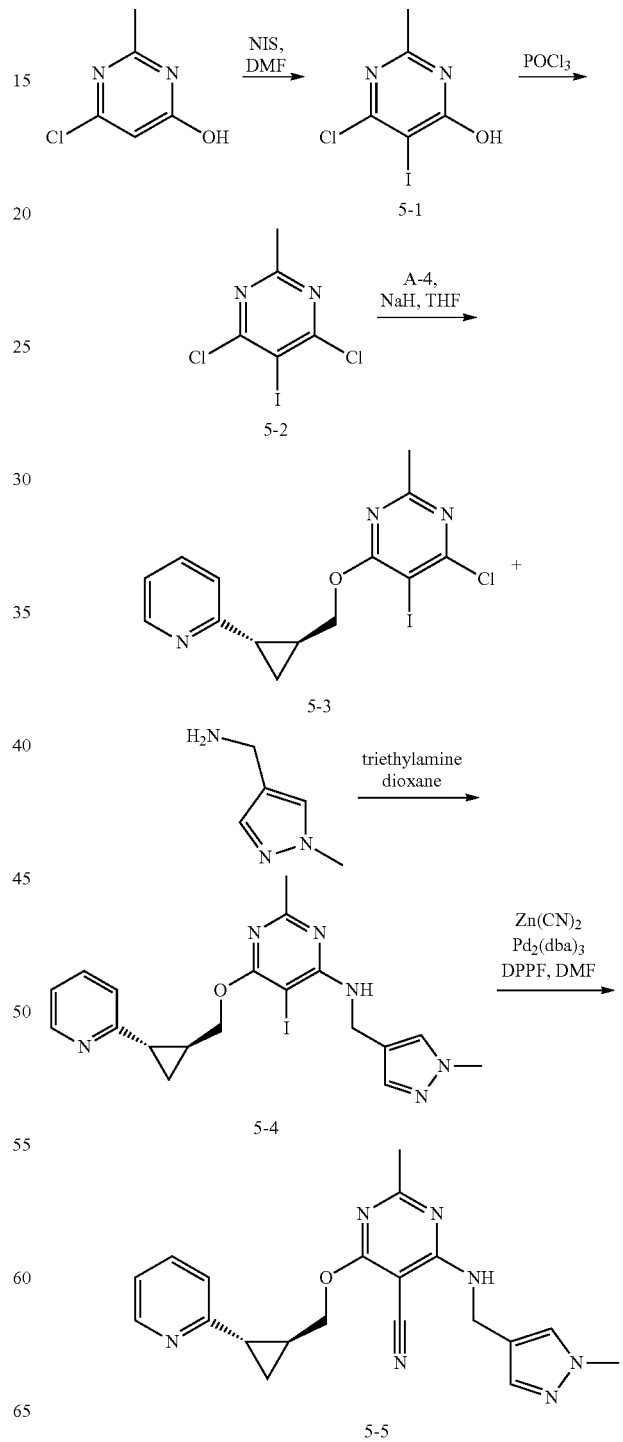

6-chloro-5-iodo-2-methylpyrimidin-4-ol 5-1

To a stirred solution of 6-chloro-2-methylpyrimidin-4-ol (1.45 g, 10.0 mmol) in DMF (19 mL) was added N-iodosuccinimide (6.78 g, 30.1 mmol). The mixture was heated to 80° C. for two hours. The reaction was allowed to cool and partitioned between ethyl acetate and a saturated ammonium chloride solution. The organic phase was concentrated and flash column separation using a 0-50% ethyl acetate/hexane gradient followed by trituration in hexane gave 5-1 as a solid. (1.83 g, 68%). LRMS (ES) (M+H)$^+$: observed=271.0, calculated=270.5.

4,6-dichloro-5-iodo-2-methylpyrimidine 5-2

To a RBF containing phosphorus oxychloride (10 mL, 107 mmol) was added 5-1 (1.83 g, 6.77 mmol) and the mixture was heated to reflux for 3 hours. The solution was concentrated, quenched with ice, and partitioned between ethyl acetate and a saturated sodium bicarbonate solution. The organic phase was concentrated and flash column separation using a 0-10% ethyl acetate/hexane gradient gave 5-2 as solid (1.38 g, 71%). LRMS (ES) (M+H)$^+$: observed=288.9, calculated=288.9.

4-chloro-5-iodo-2-methyl-6-((2-(pyridin-2-yl)cyclopropyl)methoxy)pyrimidine 5-3

To a stirred solution of A-4 (93 mg, 0.62 mmol) in THF (1.5 mL) was added sodium hydride 60% dispersion (31 mg, 0.76 mmol) and the resulting solution was stirred at room temperature for 20 minutes. To this was added 5-2 (200 mg, 0.69 mmol) and the resulting mixture was heated 60° C. for 2 hours. The reaction allowed to cool and partitioned between ethyl acetate and a saturated sodium bicarbonate solution. The organic phase was concentrated and flash column separation using a 0-30% ethyl acetate/hexane gradient gave 5-3 as a solid (208 mg, 75%). HRMS (ES) (M+H)$^+$: observed=401.9843, calculated=401.9865.

5-iodo-2-methyl-N-((1-methyl-1H-pyrazol-4-yl)methyl)-6-((2-(pyridin-2-yl)cyclopropyl)methoxy)pyrimidin-4-amine 5-4

The title compound was prepared from 5-3 according to the protocol outlined in Example 1, to afford 5-4 as a solid. LRMS (ES) (M+H)$^+$: observed=477.1, calculated=477.3.

2-methyl-4-((1-methyl-1H-pyrazol-4-yl)methylamino)-6-((2-(pyridin-2-yl)cyclopropyl)methoxy)pyrimidine-5-carbonitrile 5-5

The title compound was prepared from 5-4 according to the protocol outlined in Example 4, to afford 5-5 as a solid. HRMS (ES) (M+H)$^+$: observed=376.1869, calculated=376.1880.

EXAMPLE 6

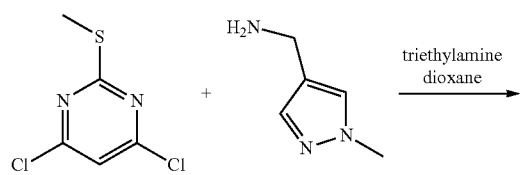

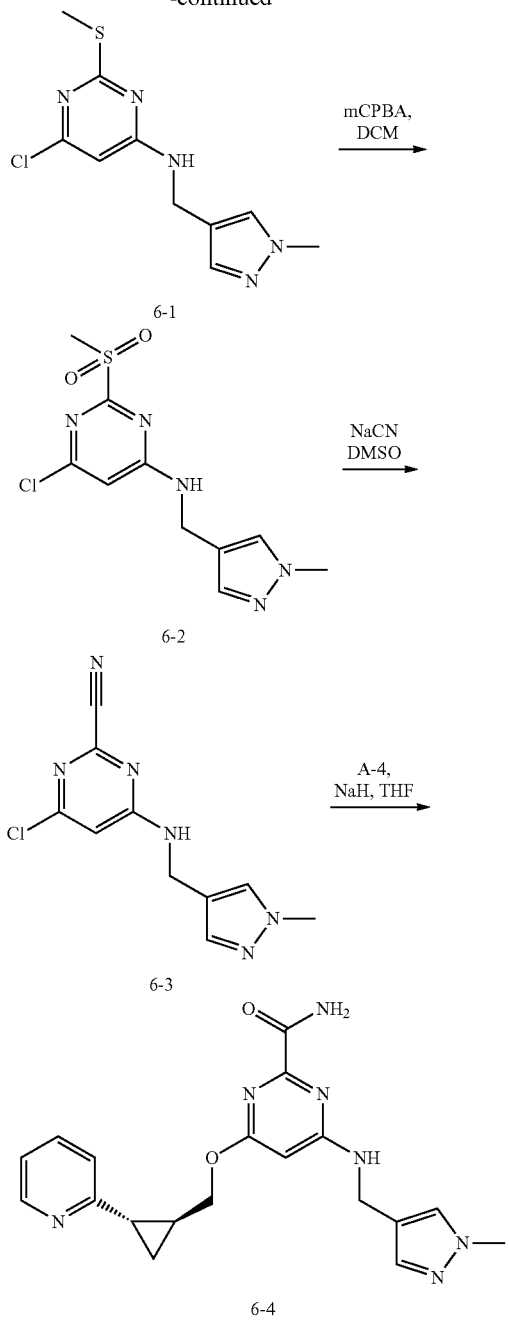

6-chloro-N-((1-methyl-1H-pyrazol-4-yl)methyl)-2-(methylthio)pyrimidin-4-amine 6-1

The title compound was prepared from 4,6-dichloro-2-(methylthio)pyrimidine according to the protocol outlined in Example 1, to afford 6-1 as a solid. LRMS (ES) (M+H)$^+$: observed=270.1, calculated=270.7.

6-chloro-N-((1-methyl-1H-pyrazol-4-yl)methyl)-2-(methylsulfonyl)pyrimidin-4-amine 6-2

To a stirred solution of 6-1 (0.25 g, 0.95 mmol) in dichloromethane (4 mL) was added mCPBA 70% (0.51 g, 2.08 mmol) and the resulting mixture was stirred at room temperature for 45 minutes. The reaction mixture was washed twice with 1N NaOH solution and concentrated to give 6-2 as a solid. (0.25 g, 70%) LRMS (ES) (M+H)$^+$: observed=302.1, calculated=302.7

4-chloro-6-((1-methyl-1H-pyrazol-4-yl)methylamino)pyrimidine-2-carbonitrile 6-3

To a stirred solution of 6-2 (0.13 g, 0.41 mmol) in DMSO (1 mL) was added sodium cyanide (0.02 g, 0.41 mmol) and the reaction was heated to 100° C. for 20 minutes. Purification using reverse phase chromatography (20-60%, 0.1% TFA in H$_2$O/acetonitrile) gave 6-3 as a solid (0.02 g, 19%). LRMS (ES) (M+H)$^+$: observed=249.1, calculated=249.6

4-((1-methyl-1H-pyrazol-4-yl)methylamino)-6-((2-(pyridin-2-yl)cyclopropyl)methoxy)-pyrimidine-2-carboxamide 6-4

The title compound was prepared from 6-3 according to the protocol outlined in Example 1, to afford 6-4 as a solid. HRMS (ES) (M+H)$^+$: observed=380.1830, calculated=380.1829.

EXAMPLE 7

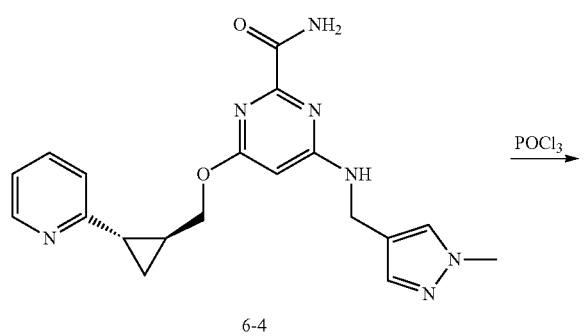

6-4

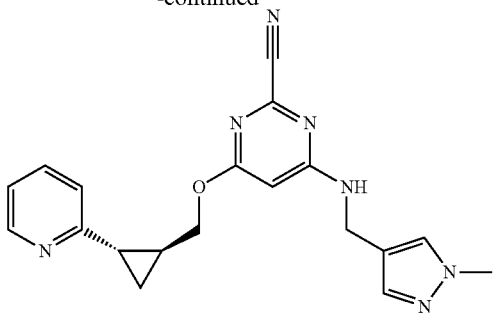

6-5

4-((1-methyl-1H-pyrazol-4-yl)methylamino)-6-((2-(pyridin-2-yl)cyclopropyl)methoxy)-pyrimidine-2-carbonitrile 6-5

To a vial containing phosphorus oxychloride (0.8 mL, 8.58 mmol) was added 6-4 (0.03 g, 0.08 mmol). The mixture was heated to 100° C. for 90 minutes. The mixture was concentrated and purified using reverse phase chromatography (10-35%, 0.1% TFA in H$_2$O/acetonitrile) to give 6-5 as a solid. (11 mg, 39%). FIRMS (ES) (M+H)$^+$: observed=362.1726, calculated=362.1724.

EXAMPLE 8

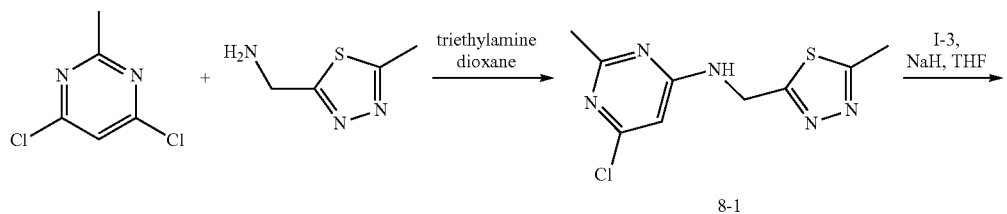

8-1

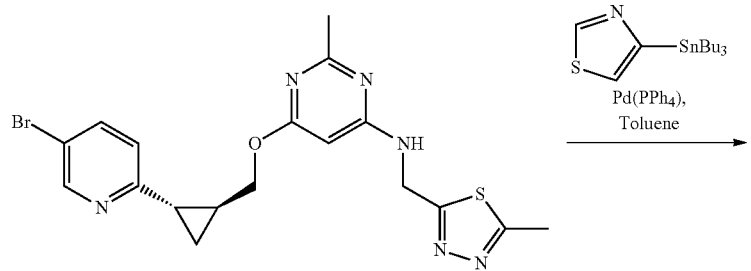

8-2

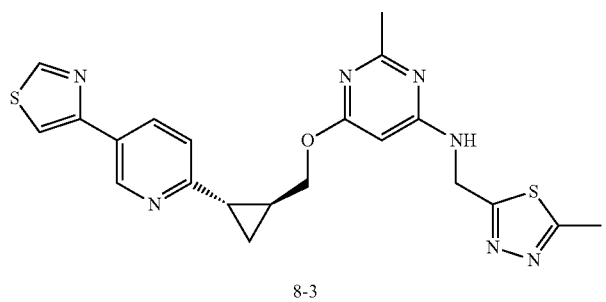

8-3

6-chloro-2-methyl-N-((5-methyl-1,3,4-thiadiazol-2-yl)methyl)pyrimidin-4-amine 8-1

The title compound was prepared from 4,6-dichloro-2-methylpyrimidine and (5-methyl-1,3,4-thiadiazol-2-yl)methanamine according to the protocol outlined in Example 1, to afford 8-1 as a solid. LRMS (ES) (M+H)$^+$: observed=256.1, calculated=256.7.

6-((2-(5-bromopyridin-2-yl)cyclopropyl)methoxy)-2-methyl-N-((5-methyl-1,3,4-thiadiazol-2-yl)methyl)pyrimidin-4-amine 8-2

The title compound was prepared from 8-1 according to the protocol outlined in Example 1, to afford 8-2 as a solid. LRMS (ES) (M+H)$^+$: observed=447.0/449.0, calculated=447.3/449.3.

2-methyl-N-((5-methyl-1,3,4-thiadiazol-2-yl)methyl)-6-((2-(5-(thiazol-4-yl)pyridin-2-yl)cyclopropyl)methoxy)pyrimidin-4-amine 8-3

To a stirred solution of 8-2 (50 mg, 0.11 mol) in toluene (0.8 mL) was added Pd(PPh$_3$)$_4$ (25 mg, 0.02 mmol) and 4-(tributylstannyl)thiazole (84 mg, 0.22 mmol) and the resulting mixture was microwave irradiated to 140° C. for 2 hours. The solution was concentrated and purified using reverse phase chromatography (10-30%, 0.1% TFA in H$_2$O/acetonitrile) to give 8-3 as a solid. (19 mg, 38%). HRMS (ES) (M+H)$^+$: observed=452.1322, calculated=452.1322.

TABLE 3

The following compounds were prepared in an analogous manner to Example 8, using the appropriate tin reagent.

| Cpd. | Name | HRMS/LRMS |
|---|---|---|
| 8-4 | 6-{[2-(2,3'-bipyridin-6'-yl)cyclopropyl]methoxy}-2-methyl-N-[(5-methyl-1,3,4-thiadiazol-2-yl)methyl]pyrimidin-4-amine | C23H23N7OS [M + H] calc 446.1758 obs 446.1760 |
| 8-5 | 2-methyl-N-[(5-methyl-1,3,4-thiadiazol-2-yl)methyl]-6-({2-[5-(1,3-thiazol-5-yl)pyridin-2-yl]cyclopropyl}methoxy)pyrimidin-4-amine | C21H21N7OS2 [M + H] calc 452.1322 obs 452.1321 |
| 8-6 | 6-{[2-(3,4'-bipyridin-6-yl)cyclopropyl]methoxy}-2-methyl-N-[(5-methyl-1,3,4-thiadiazol-2-yl)methyl]pyrimidin-4-amine | C23H23N7OS [M + H] calc 446.1758 obs 446.1762 |
| 8-7 | 2-methyl-N-[(5-methyl-1,3,4-thiadiazol-2-yl)methyl]-6-({2-[5-(1,3-thiazol-2-yl)pyridin-2-yl]cyclopropyl}methoxy)pyrimidin-4-amine | C21H21N7OS2 [M + H] calc 452.1322 obs 452.1328 |
| 8-8 | 6-{[2-(3,3'-bipyridin-6-yl)cyclopropyl]methoxy}-2-methyl-N-[(5-methyl-1,3,4-thiadiazol-2-yl)methyl]pyrimidin-4-amine | C23H23N7OS [M + H] calc 446.1758 obs 446.1761 |

TABLE 3-continued

The following compounds were prepared in an analogous manner to Example 8, using the appropriate tin reagent.

| Cpd. | Structure | Name | HRMS/LRMS |
|---|---|---|---|
| 8-9 | 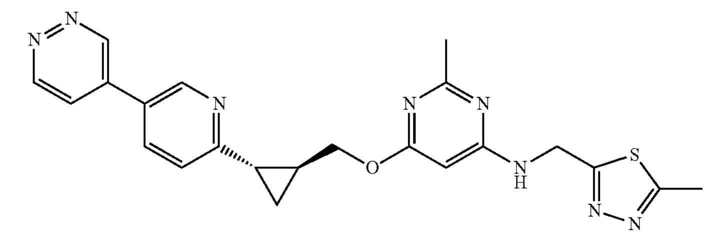 [SMILES: Cc1nc(NCc2nnc(C)s2)cc(OC[C@H]2C[C@@H]2c2ccc(-c3ccnnc3)cn2)n1] | 2-methyl-N-[(5-methyl-1,3,4-thiadiazol-2-yl)methyl]-6-{[2-(5-pyridazin-4-ylpyridin-2-yl)cyclopropyl]methoxy}pyrimidin-4-amine | C22H22N8OS [M + H] calc 447.1710 obs 447.1709 |

Starting materials not previously illustrated were commercially available, described in the literature, or readily synthesized by one skilled in the art of organic synthesis without undue experimentation.

EXAMPLE 9

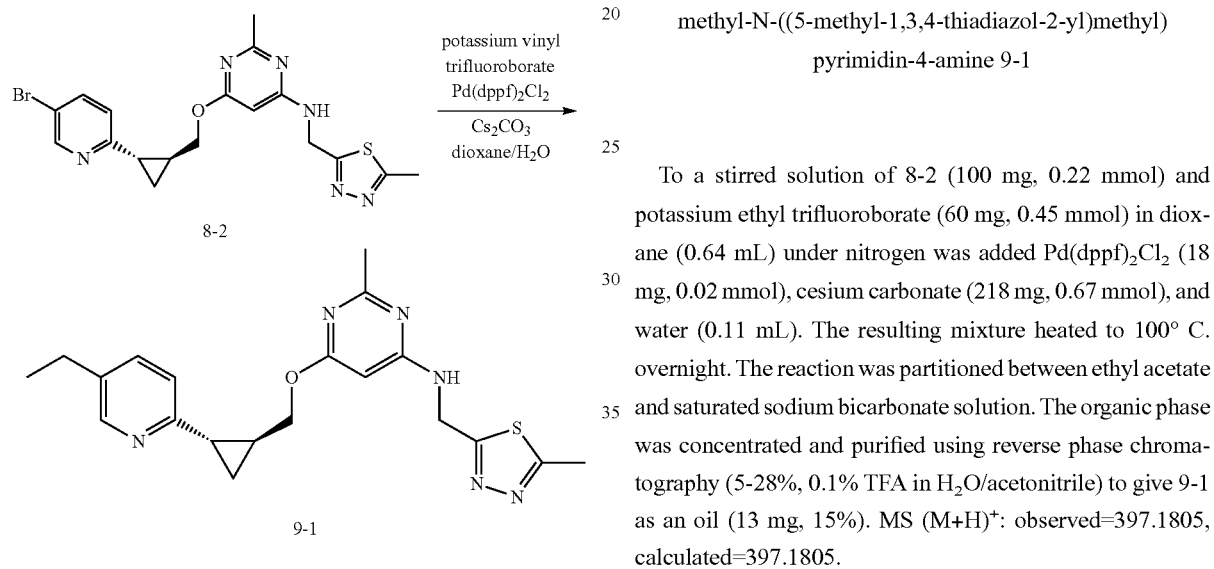

6-((2-(5-ethylpyridin-2-yl)cyclopropyl)methoxy)-2-methyl-N-((5-methyl-1,3,4-thiadiazol-2-yl)methyl)pyrimidin-4-amine 9-1

To a stirred solution of 8-2 (100 mg, 0.22 mmol) and potassium ethyl trifluoroborate (60 mg, 0.45 mmol) in dioxane (0.64 mL) under nitrogen was added Pd(dppf)$_2$Cl$_2$ (18 mg, 0.02 mmol), cesium carbonate (218 mg, 0.67 mmol), and water (0.11 mL). The resulting mixture heated to 100° C. overnight. The reaction was partitioned between ethyl acetate and saturated sodium bicarbonate solution. The organic phase was concentrated and purified using reverse phase chromatography (5-28%, 0.1% TFA in H$_2$O/acetonitrile) to give 9-1 as an oil (13 mg, 15%). MS (M+H)$^+$: observed=397.1805, calculated=397.1805.

TABLE 4

The following compounds were prepared in an analogous manner to Example 9, using the appropriate fluoroborate salt.

| Cpd. | Structure | Name | HRMS/LRMS |
|---|---|---|---|
| 9-2 | 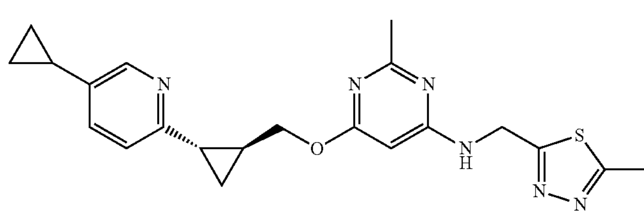 [SMILES: Cc1nc(NCc2nnc(C)s2)cc(OC[C@H]2C[C@@H]2c2ccc(C3CC3)cn2)n1] | 6-{[2-(5-cyclopropylpyridin-2-yl)cyclopropyl]methoxy}-2-methyl-N-[(5-methyl-1,3,4-thiadiazol-2-yl)methyl]pyrimidin-4-amine | C21H24N6OS [M + H] calc 409.1805 obs 409.1806 |

Starting materials not previously illustrated were commercially available, described in the literature, or readily synthesized by one skilled in the art of organic synthesis without undue experimentation.

EXAMPLE 10

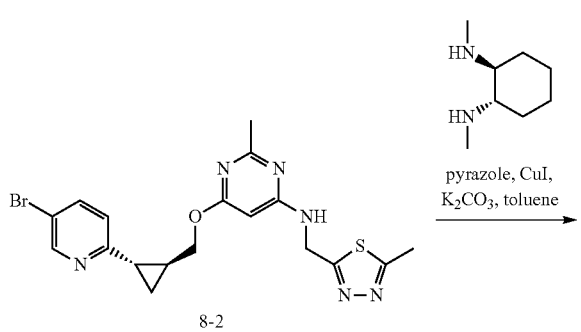

6-((2-(5-(1H-pyrazol-1-yl)pyridin-2-yl)cyclopropyl)methoxy)-2-methyl-N-((5-methyl-1,3,4-thiadiazol-2-yl)methyl)pyrimidin-4-amine 10-1

To a stirred solution of 8-2 (75 mg, 0.17 mmol) in toluene (0.8 mL) under nitrogen was added pyrazole (23 mg, 0.34 mmol), copper (I) iodide (6.3 mg, 0.03 mmol), 1,2-trans-N,N'-dimethyldiaminocyclohexane (10 mg, 0.07 mmol), and potassium carbonate (49 mg, 0.35 mmol). The resulting mixture was heated to 120° C. overnight. The reaction was concentrated and purified using reverse phase chromatography (10-30%, 0.1% TFA in H$_2$O/acetonitrile) to give 10-1 as a solid (36 mg, 49%). MS (M+H)$^+$: observed=435.1715, calculated=435.1710.

EXAMPLE 11

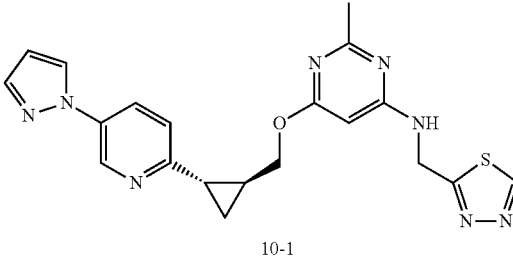

6-(2-((2-methyl-6-((5-methyl-1,3,4-thiadiazol-2-yl)methylamino)pyrimidin-4-yloxy)methyl)cyclopropyl)nicotinonitrile 11-1

The title compound was prepared from 8-2 according to the protocol outlined in Example 4, to afford 11-1 as a solid. HRMS (ES) (M+H)$^+$: observed=394.1440, calculated=394.1445.

EXAMPLE 12

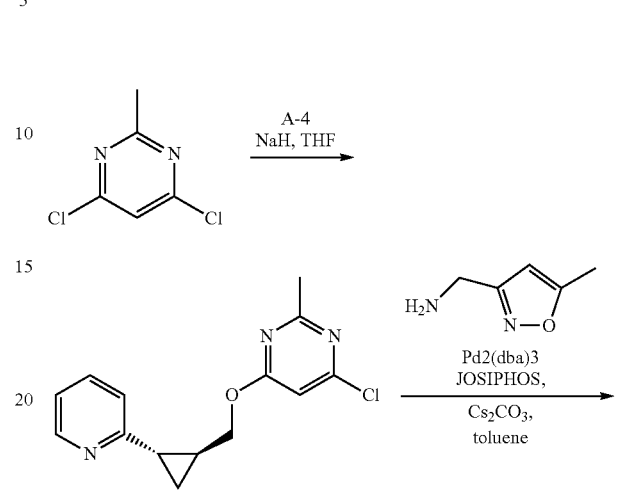

4-chloro-2-methyl-6-((2-(pyridin-2-yl)cyclopropyl)methoxy)pyrimidine 12-1

The title compound was prepared from 4,6-dichloro-2-methylpyrimidine according to the protocol outlined in Example 5, to afford 12-1 as an oil. LRMS (ES) (M+H)$^+$: observed=276.1, calculated=276.7.

2-methyl-N-((5-methylisoxazol-3-yl)methyl)-6-((2-(pyridin-2-yl)cyclopropyl)methoxy)-pyrimidin-4-amine 12-2

To a stirred solution of 12-1 (50 mg, 0.18 mmol) and (5-methylisoxazol-3-yl)methanamine (22 mg, 0.20 mmol) in toluene (1.0 mL) was added (R)-1-[(S)-2-(dicyclohexylphosphino)ferrocenyl]ethyldi-tert-butylphosphine (22 mg, 0.04 mmol), Pd$_2$(dba)$_3$ (17 mg, 0.02 mmol), and cesium carbonate (177 mg, 0.54 mmol). The resulting mixture was microwave irradiated to 140° C. for 2 hours. The reaction was partitioned between ethyl acetate and saturated sodium bicarbonate solution. The organic phase was concentrated and purified using reverse phase chromatography (10-35%, 0.1% TFA in H$_2$O/acetonitrile) to give 12-2 as an oil (15 mg, 24%). HRMS (ES) (M+H)$^+$: observed=352.1773, calculated=352.1768.

TABLE 5

The following compounds were prepared in an analogous manner to Example 12, using the appropriate amine.

| Cpd. | Structure | Name | HRMS/LRMS |
|---|---|---|---|
| 12-3 | 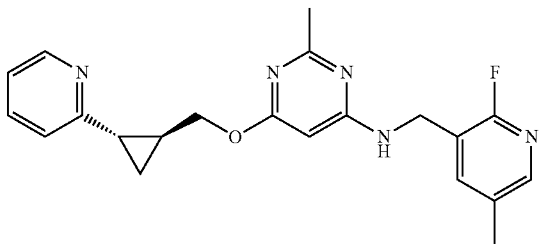 [SMILES: Cc1cnc(F)c(CNc2cc(OC[C@H]3C[C@@H]3c3ccccn3)nc(C)n2)c1] | N-[(2-fluoro-5-methyl-pyridin-3-yl)methyl]-2-methyl-6-[(2-pyridin-2-ylcyclopropyl)methoxy]pyrimidin-4-amine | C21H22FN5O [M + H] calc 380.1881 obs 380.1884 |
| 12-4 | 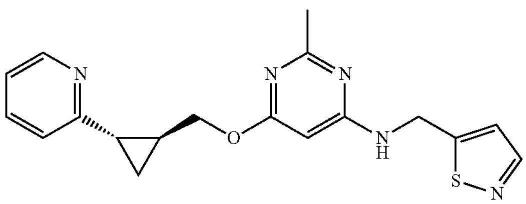 [SMILES: Cc1nc(NCc2ccns2)cc(OC[C@H]2C[C@@H]2c2ccccn2)n1] | S,S-N-(isothiazol-5-ylmethyl)-2-methyl-6-[(2-pyridin-2-ylcyclopropyl)-methoxy]pyrimidin-4-amine | C18H19N5OS [M + H] calc 354.1383 obs 354.1385 |
| 12-5 | 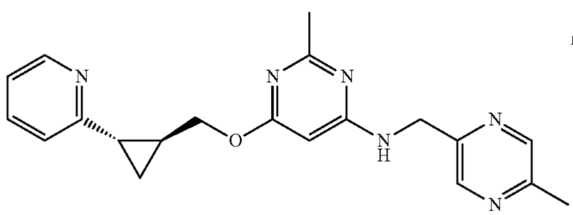 [SMILES: Cc1cnc(CNc2cc(OC[C@H]3C[C@@H]3c3ccccn3)nc(C)n2)cn1] | 2-methyl-N-[(5-methylpyrazin-2-yl)methyl]-6-[(2-pyridin-2-ylcyclopropyl)methoxy]-pyrimidin-4-amine | C20H22N6O [M + H] calc 363.1928 obs 363.1931 |
| 12-6 | 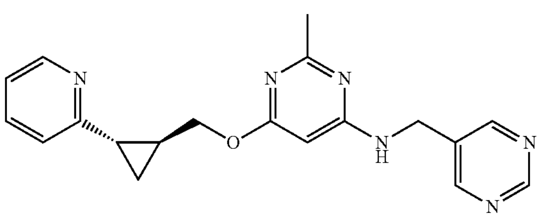 [SMILES: Cc1nc(NCc2cncnc2)cc(OC[C@H]2C[C@@H]2c2ccccn2)n1] | 2-methyl-6-[(2-pyridin-2-ylcyclopropyl)methoxy]-N-(pyrimidin-5-ylmethyl)-pyrimidin-4-amine | C19H20N6O [M + H] calc 349.1771 obs 349.1774 |

Starting materials not previously illustrated were commercially available, described in the literature, or readily synthesized by one skilled in the art of organic synthesis without undue experimentation.

EXAMPLE 13

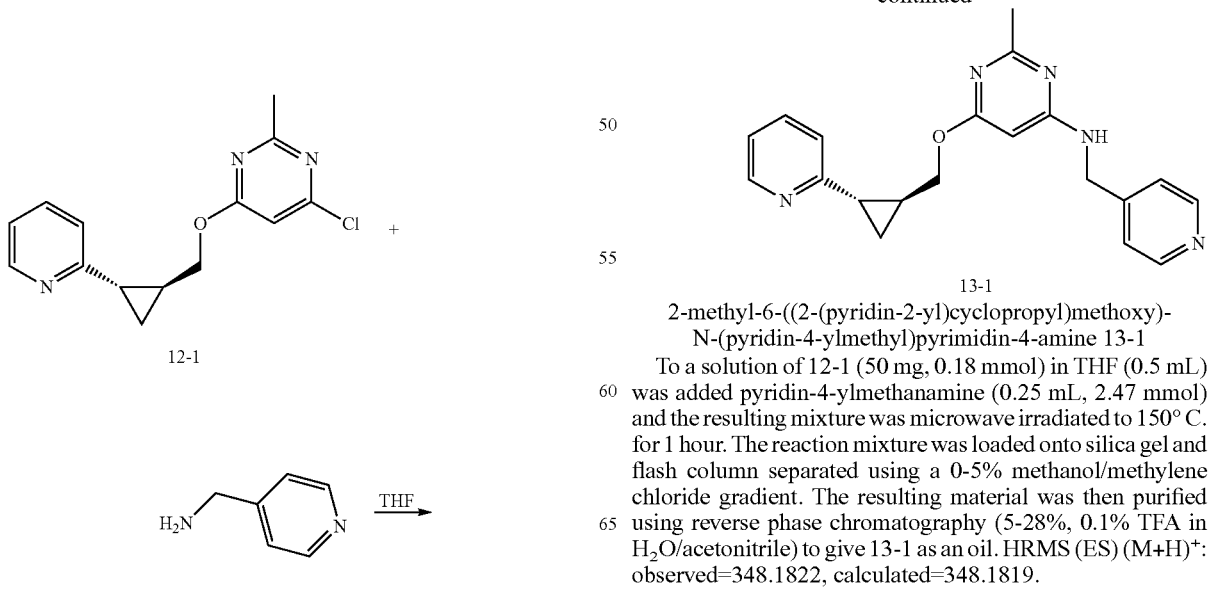

13-1

2-methyl-6-((2-(pyridin-2-yl)cyclopropyl)methoxy)-N-(pyridin-4-ylmethyl)pyrimidin-4-amine 13-1

To a solution of 12-1 (50 mg, 0.18 mmol) in THF (0.5 mL) was added pyridin-4-ylmethanamine (0.25 mL, 2.47 mmol) and the resulting mixture was microwave irradiated to 150° C. for 1 hour. The reaction mixture was loaded onto silica gel and flash column separated using a 0-5% methanol/methylene chloride gradient. The resulting material was then purified using reverse phase chromatography (5-28%, 0.1% TFA in H$_2$O/acetonitrile) to give 13-1 as an oil. HRMS (ES) (M+H)$^+$: observed=348.1822, calculated=348.1819.

TABLE 6

The following compounds were prepared in an analogous manner to Example 13, using the appropriate amine.

| Cpd. | Structure | Name | HRMS/LRMS |
|---|---|---|---|
| 13-2 | 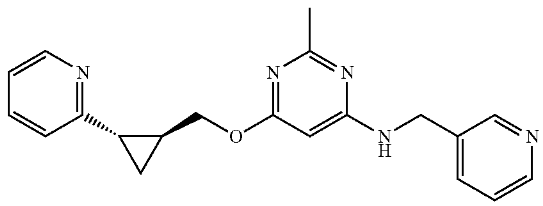 [SMILES: Cc1nc(NCc2cccnc2)cc(OC[C@H]2C[C@@H]2c2ccccn2)n1] | 2-methyl-6-[(2-pyridin-2-ylcyclopropyl)-methoxy]-N-(pyridin-3-ylmethyl)pyrimidin-4-amine | C20H21N5O [M + H] calc 348.1819 obs 348.1824 |

Starting materials not previously illustrated were commercially available, described in the literature, or readily synthesized by one skilled in the art of organic synthesis without undue experimentation.

EXAMPLE 14

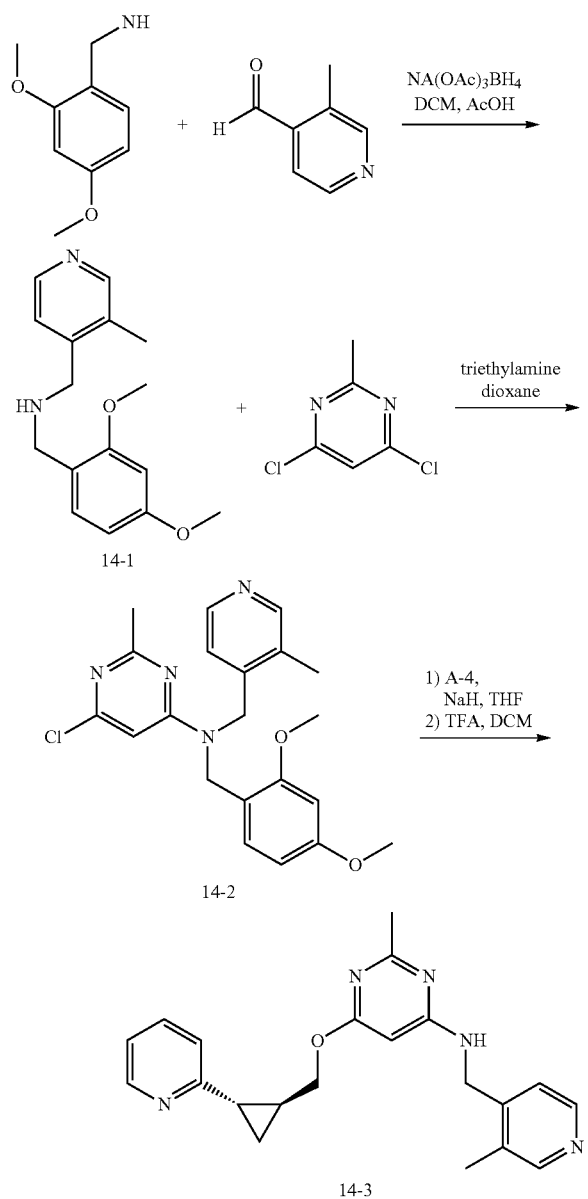

N-(2,4-dimethoxybenzyl)-1-(3-methylpyridin-4-yl)methanamine 14-1

To a stirred solution of 3-methylisonicotinaldehyde (0.30 g, 2.48 mmol) in DCM (7 mL) was added (2,4-dimethoxyphenyl)methanamine (0.41 g, 2.48 mmol) and acetic acid (0.7 mL). The resulting solution was stirred overnight at room temperature. To this was added sodium triacetoxyborohydride (1.05 g, 4.95 mmol). The reaction was quenched with a saturated sodium bicarbonate solution and extracted with DCM. The combined organic phase was concentrated and flash column separated using a 0-5% methanol/methylene chloride gradient to give 14-1 as a solid (0.18 g, 17%). LRMS (ES) (M+H)$^+$: observed=273.2, calculated=273.3.

6-chloro-N-(2,4-dimethoxybenzyl)-2-methyl-N-((3-methylpyridin-4-yl)methyl)pyrimidin-4-amine 14-2

The title compound was prepared from 14-1 and 4,6-dichloro-2-methylpyrimidine according to the protocol outlined in Example 1, to afford 14-2 as a solid. LRMS (ES) (M+H)$^+$: observed=399.1, calculated=399.8.

2-methyl-N-((3-methylpyridin-4-yl)methyl)-6-((2-(pyridin-2-yl)cyclopropyl)methoxy)pyrimidin-4-amine 14-3

To a stirred solution of A-4 (79 mg, 0.53 mmol) in THF (1 mL) was added sodium hydride 60% dispersion (28 mg, 0.70 mmol) and the resulting solution was stirred at room temperature for 20 minutes. To this was added 14-2 (140 mg, 0.35 mmol) and the resulting mixture was microwave irradiated at 100° C. for 90 minutes. The reaction was concentrated. The residue was taken up in trifluoroacetic acid (2 mL) and stirred at room temperature overnight. The reaction was concentrated and partitioned between ethyl acetate and a saturated sodium bicarbonate solution. The organic phase was concentrated and purified using reverse phase chromatography (5-28%, 0.1% TFA in H$_2$O/acetonitrile) to give 14-3 as a white solid (32 mg, 25%). HRMS (ES) (M+H)$^+$: observed=362.1985, calculated=362.1975.

EXAMPLE 15

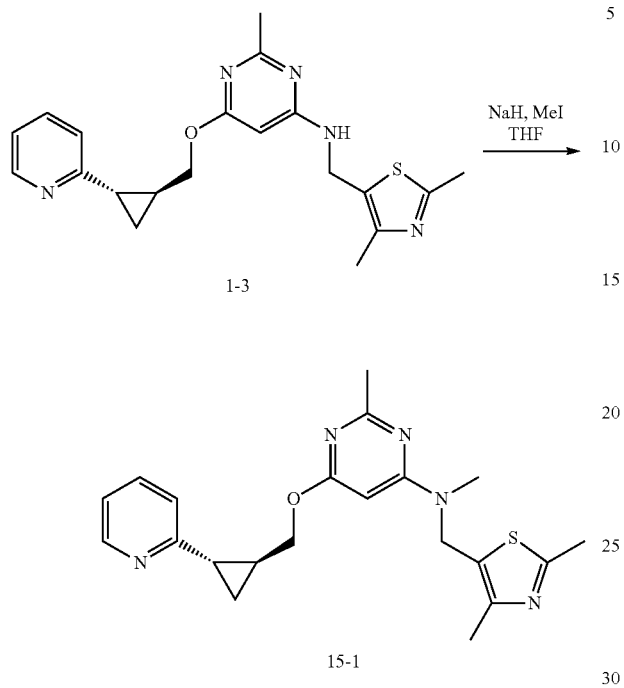

6-(2-((2-methyl-6-((5-methyl-1,3,4-thiadiazol-2-yl)
methylamino)pyrimidin-4-yloxy)methyl)cyclopro-
pyl)pyridine 15-1

To a stirred solution of 1-3 (25 mg, 0.07 mmol) in THF (1 mL) was added sodium hydride 60% dispersion (3.0 mg, 0.07 mmol) and the resulting solution was stirred at room temperature for 20 minutes. To this was added methyl iodide (9.3 mg, 0.07 mmol) and the resulting solution was stirred room temperature overnight. The reaction was concentrated and purified using reverse phase chromatography (5-60%, 0.1% TFA in H$_2$O/acetonitrile) to give 15-1 as a white solid (13 mg, 25%). HRMS (ES) (M+H)$^+$: observed=396.1858, calculated=396.1853.

EXAMPLE 16

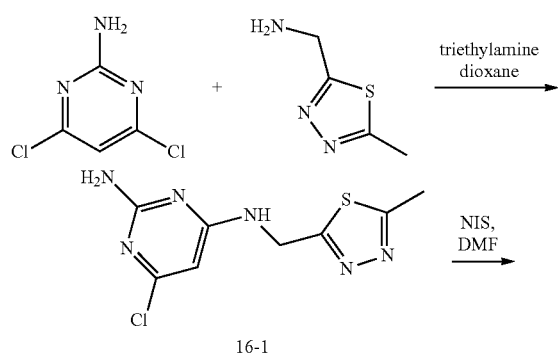

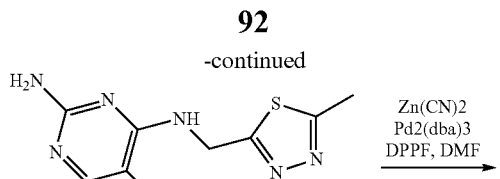

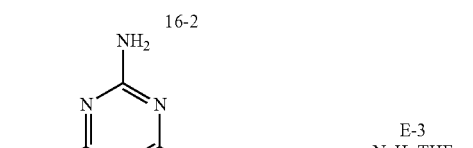

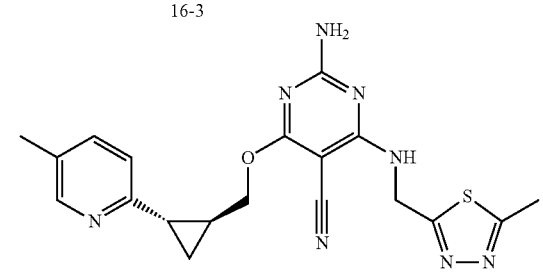

2-amino-4-{[(1S,2S)-2-(5-methylpyridin-2-yl)cyclo-
propyl]methoxy}-6-{[(5-methyl-1,3,4-thiadiazol-2-
yl)methyl]amino}pyrimidine-5-carbonitrile (16-4)

6-chloro-N-4-((5-methyl-1,3,4-thiadiazol-2-yl)me-
thyl)pyrimidine-2,4-diamine (16-1)

To a stirred solution of 4,6-dichloro-2-aminopyrimidine (800 mg, 4.88 mmol) in dioxane (10 mL) was added triethylamine (2.0 mL, 14.64 mmol) and (5-methyl-1,3,4-thiadiazol-2-yl)methanamine hydrochloride (1050 mg, 6.34 mmol). The resulting mixture was microwave irradiated at 150° C. for 30 minutes. The reaction was diluted with ethyl acetate and washed with saturated sodium bicarbonate solution. The organic phase was concentrated and flash column separation using a 10-100% ethyl acetate/hexane gradient gave 16-1 as a white solid (600 mg, 48%). MS (M+H)$^+$: observed=257.7, calculated=257.1.

6-chloro-5-iodo-N4-((5-methyl-1,3,4-thiadiazol-2-
yl)methyl)pyrimidine-2,4-diamine (16-2)

To a stirred solution of 16-1 (570 mg, 2.22 mmol) in DMF (6 mL) was added N-iodosuccinimide (1.25 g, 5.55 mmol) and the resulting mixture was heated to 80° C. for 15 minutes. The reaction was allowed to cool, poured into a saturated sodium bicarbonate solution and extracted several times with ethyl acetate. The combined organic layers were washed several times with a sodium thiosulfate solution, and concentrated. Flash column separation using a 30-100% ethyl acetate/hexane gradient gave 16-2 as a solid (639 mg, 75%). MS (M+H)$^+$: observed=383.1, calculated=363.6.

2-amino-4-chloro-6-((5-methyl-1,3,4-thiadiazol-2-
yl)methylamino)pyrimidine-5-carbonitrile (16-3)

To a stirred solution of 16-2 (639 mg, 1.67 mmol), and zinc cyanide (98 mg, 0.84 mmol) in DMF (6 mL) under nitrogen was added Pd$_2$(dba)$_3$ (76 mg, 0.08 mmol) and DPPF (93 mg, 0.17 mmol) and the resulting mixture was heated to 120° C. for 90 minutes. The reaction was allowed to cool and partitioned between ethyl acetate and a saturated sodium bicarbonate solution. The organic phase was concentrated and flash column separation using a 10-100% ethyl acetate/hexane gradient gave 16-3 as a solid (200 mg, 43%). MS (ES) (M+H)$^+$: observed=282.2, calculated=282.7.

2-amino-4-{[(1S,2S)-2-(5-methylpyridin-2-yl)cyclopropyl]methoxy}-6-{[(5-methyl-1,3,4-thiadiazol-2-yl)methyl]amino}pyrimidine-5-carbonitrile (16-4)

The title compound was prepared from 16-3 according to the protocol outlined in Example 1, to afford 16-4 as a solid. HRMS (ES) (M+H)$^+$: observed=409.1553, calculated=409.1554.

TABLE 7

The following compounds were prepared in an analogous manner to Example 16, using the appropriate amine.

| Cpd. | Structure | Name | HRMS/LRMS |
|---|---|---|---|
| 16-5 | 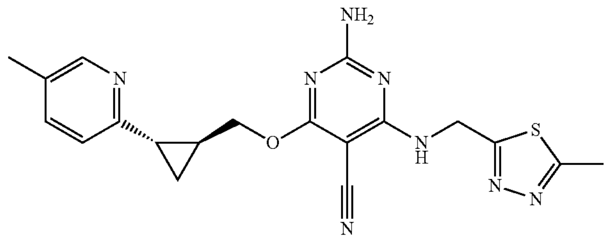 | S,S-2-amino-4-{[(1S,2S)-2-(5-methylpyridin-2-yl)cyclopropyl]methoxy}-6-{[(5-methyl-1,3,4-thiadiazol-2-yl)methyl]amino}pyrimidine-5-carbonitrile | C19H20N8OS [M + H] calc 409.1554 obs 409.1553 |
| 16-6 | 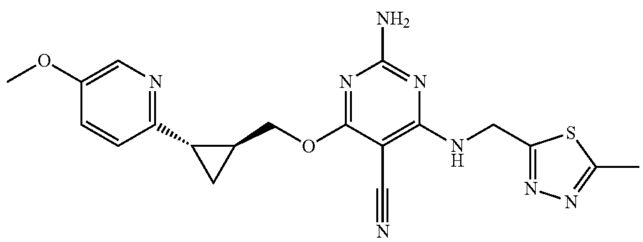 | S,S-2-amino-4-{[(1S,2S)-2-(5-methoxypyridin-2-yl)cyclopropyl]methoxy}-6-{[(5-methyl-1,3,4-thiadiazol-2-yl)methyl]amino}pyrimidine-5-carbonitrile | C19H20N8O2S [M + H] calc 425.1503 obs 425.1505 |

Starting materials not previously illustrated were commercially available, described in the literature, or readily synthesized by one skilled in the art of organic synthesis without undue experimentation.

EXAMPLE 17

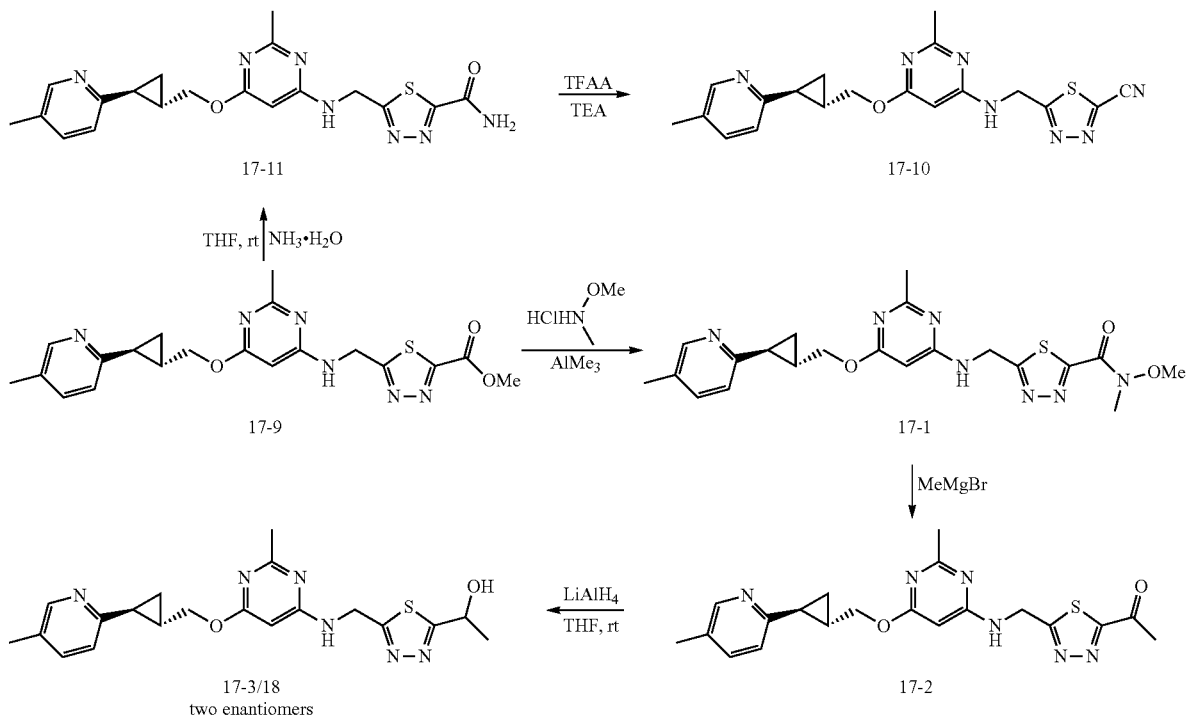

N-methoxy-N-methyl-5-((2-methyl-6-(((1S,2S)-2-(5-methylpyridin-2-yl)cyclopropyl)methoxy)pyrimidin-4-ylamino)methyl)-1,3,4-thiadiazole-2-carboxamide (17-1)

To the solution of N-methoxymethanamine hydrochloride (361 mg, 3.70 mmol) in dichloromethane (10 mL) was added trimethylaluminum in toluene (1.8 mL, 3.70 mmol) dropwise at 0° C. The mixture was stirred for 30 min before ethyl 5-((2-methyl-6-((1S,2S)-2-(5-methylpyridin-2-yl)cyclopropyl)methoxy)pyrimidin-4-ylamino)methyl)-1,3,4-thiadiazole-2-carboxylate (9) (355 mg, 0.74 mmol) in dichloromethane (10 mL) was added at 0° C. Then it was stirred for 1 h and quenched with saturated potassium phosphate (2 mL) to pH=9-10. The resulting mixture was extracted with ethyl acetate (20 mL*3). The combined organic phase was concentrated and purified by Pre-TLC (PE/EA=2/1) to yield product as a white solid (355 mg, 100%). $^1$H NMR (400 MHz, CDCl$_3$) δ 8.21 (s, 1H), 7.30 (dd, J=7.9, 1.2 Hz, 1H), 6.99 (d, J=7.9 Hz, 1H), 6.16 (s, 1H), 5.62 (s, 1H), 4.95 (t, J=9.3 Hz, 1H), 4.22 (qd, J=11.1, 7.0 Hz, 2H), 3.79 (s, 3H), 3.37 (s, 1H), 2.41 (s, 3H), 2.24 (d, J=11.2 Hz, 3H), 2.08-1.89 (m, 1H), 1.89-1.58 (m, 1H), 1.34-1.08 (m, 1H), 1.04-0.62 (m, 1H); LRMS (ESI) calculated M+H for C21H26N7O3S: 456.5. Found: 456.1.

1-(5-((2-methyl-6-(((1S,2S)-2-(5-methylpyridin-2-yl)cyclopropyl)methoxy)pyrimidin-4-ylamino)methyl)-1,3,4-thiadiazol-2-yl)ethanone (17-2)

To the solution of N-methoxy-N-methyl-5-((2-methyl-6-(((1S,2S)-2-(5-methylpyridin-2-yl)cyclopropyl)methoxy)pyrimidin-4-ylamino)methyl)-1,3,4-thiadiazole-2-carboxamide (17-1) (355 mg, 0.78 mmol) in THF (2 mL) was added CH$_3$MgBr (1.3 mL, 3.90 mmol) in toluene dropwise at 0° C. The mixture was stirred for 30 min. Then the solution was adjusted to pH=9-10 with saturated sodium bicarbonate and extracted with ethyl acetate (20 mL*3). The organic layers were combined, dried over anhydrous sodium sulfate and purified by Prep TLC (PE/EA=1:1). The product was obtained as a white solid (248 mg, 77%). $^1$H NMR (400 MHz, CDCl$_3$) δ 8.26 (s, 1H), 7.37 (d, J=7.6 Hz, 1H), 7.03 (d, J=7.9 Hz, 1H), 5.59 (s, 1H), 5.42 (s, 1H), 4.99 (d, J=6.3 Hz, 2H), 4.28 (m, 2H), 2.79 (s, 3H), 2.44 (s, 3H), 2.28 (s, 3H), 2.07 (m, 1H), 1.89-1.81 (m, 1H), 1.32-1.27 (m, 1H), 1.04-1.02 (m, 1H); LRMS (ES) calculated M+H for C20H23N6O2S: 411.5. Found:411.1.

1-(5-((2-Methyl-6-(((1S,2S)-2-(5-methylpyridin-2-yl)cyclopropyl)methoxy)pyrimidin-4-ylamino)methyl)-1,3,4-thiadiazol-2-yl)ethanol (17-3/18)

To the solution of 1-(5-((2-methyl-6-(((1S,2S)-2-(5-methylpyridin-2-yl)cyclopropyl)methoxy)pyrimidin-4-ylamino)methyl)-1,3,4-thiadiazol-2-yl)ethanone (17-2) (366 mg, 0.89 mmol) in THF (2 mL) was added LiAlH$_4$ (51 mg, 1.34 mmol) in small portions at 0° C. Then it was brought to rt and stirred for 1 h. The mixture was quenched in sequence with 1 mL of water, 0.5 mL of sodium hydroxyl aqueous (2.0M) and 1 mL of water. Anhydrous sodium sulfate was added and it was filtered. The filtrate was evaporated under reduced pressure to give the product as a white solid (180 mg, 49%). Enantiomers can be resolved by chiral preparative AS-H (4.6 cm i.d.×25 cm ChiralTech IC, 20% MeOH/CO$_2$, 2.4 mL/min) and analyzed by chiral analytical AS-H (4.6 mm i.d.×25 cm ChiralTech IC, 20% MeOH/CO$_2$, 2.4 mL/min) ent$_1$=3.08 min, ent$_2$=4.05 min.

ent1:
$^1$H NMR (400 MHz, CDCl$_3$) δ 8.27 (s, 1H), 7.38 (d, J=7.8 Hz, 1H), 7.04 (d, J=7.9 Hz, 1H), 5.58 (s, 1H), 5.50 (s, 1H), 5.27 (d, J=6.5 Hz, 1H), 4.90 (d, J=6.2 Hz, 1H), 4.34-4.22 (m, 2H), 2.44 (s, 3H), 2.26 (s, 3H), 2.02 (dd, J=8.7, 4.4 Hz, 1H), 1.85-1.82 (m, 1H), 1.66 (d, J=6.5 Hz, 3H), 1.31-1.07 (m, 1H), 1.05-1.02 (m, 1H); LRMS (ESI) calculated M+H for C20H25N6O2S: 413.5. Found: 413.2.

ent2:
$^1$H NMR (400 MHz, CDCl$_3$) δ 8.26 (s, 1H), 7.37 (d, J=7.2 Hz, 1H), 7.03 (d, J=8.0 Hz, 1H), 5.80 (s, 1H), 5.61 (s, 1H), 5.28 (q, J=6.5 Hz, 1H), 4.90 (d, J=6.0 Hz, 2H), 4.33-4.20 (m, 2H), 2.46 (s, 3H), 2.29 (s, 3H), 2.08-2.04 (m, 1H), 1.86-1.81 (m, 1H), 1.66 (d, J=6.5 Hz, 3H), 1.30-1.26 (m, 1H), 1.06-1.02 (m, 1H); LRMS (ESI) calculated M+H for C20H25N6O2S: 413.5. Found: 413.2.

5-((2-methyl-6-(((1S,2S)-2-(5-methylpyridin-2-yl)cyclopropyl)methoxy)pyrimidin-4-ylamino)methyl)-1,3,4-thiadiazole-2-carbonitrile (17-10)

To the solution of 5-((2-methyl-6-(((1S,2S)-2-(5-methylpyridin-2-yl)cyclopropyl)methoxy)pyrimidin-4-ylamino)methyl)-1,3,4-thiadiazole-2-carboxamide (17-11) (116 mg, 0.15 mmol) in THF was added NEt$_3$ (0.1 mL, 0.7037 mmol) and TFAA (74 mg, 0.35 mmol) at 0° C. The mixture was brought to rt and stirred for 1 h. Then it was concentrated under reduced pressure and purified on silica gel (eluent PE/EA/NEt$_3$=10/1/1%-5/1/1%) to give the product as a pale red solid (40 mg, 70%). $^1$H NMR (400 MHz, CDCl$_3$) δ 8.26 (s, 1H), 7.38 (dd, J=7.9, 1.7 Hz, 1H), 7.04 (d, J=7.9 Hz, 1H), 5.62 (s, 1H), 5.37 (t, J=5.9 Hz, 1H), 5.05 (d, J=6.2 Hz, 2H), 4.29 (ddd, J=27.7, 11.2, 7.0 Hz, 2H), 2.49 (s, 3H), 2.28 (s, 3H), 2.16-2.03 (m, 1H), 1.96-1.70 (m, 1H), 1.41-1.17 (m, 1H), 1.17-0.94 (m, 1H); LRMS (ESI) calculated M+H for C19H20N7OS: 394.4. Found: 394.1.

5-((2-methyl-6-(((1S,2S)-2-(5-methylpyridin-2-yl)cyclopropyl)methoxy)pyrimidin-4-ylamino)methyl)-1,3,4-thiadiazole-2-carboxamide (17-11)

The solution of ethyl 5-((2-methyl-6-(((1S,2S)-2-(5-methylpyridin-2-yl)cyclopropyl)methoxy)pyrimidin-4-ylamino)methyl)-1,3,4-thiadiazole-2-carboxylate (9) (80 mg, 0.18 mmol) in THF (2 mL) and 28% NH$_3$H$_2$O (2 mL) was stirred for overnight at room temperature. The solvent was removed under reduced pressure and the residue was purified by reverse phase column (Waters Sunfire Prep C18 OBD, 5-75% methanol in water with 0.1% NH$_3$H$_2$O modifier) to provide product as a white solid (25 mg, 21.4%). The title product was obtained as a white solid (60 mg, 80%). $^1$H NMR (500 MHz, CDCl$_3$) δ 8.25 (s, 1H), 7.46 (s, 1H), 7.34 (dd, J=7.9, 1.6 Hz, 1H), 7.01 (d, J=7.9 Hz, 1H), 6.76 (s, 1H), 6.16 (s, 1H), 5.60 (s, 1H), 4.97 (d, J=6.2 Hz, 2H), 4.25 (ddd, J=36.6, 11.1, 7.0 Hz, 2H), 2.44 (s, 3H), 2.25 (s, 3H), 2.08-2.01 (m, 1H), 1.91-1.71 (m, 1H), 1.30-1.19 (m, 1H), 1.02 (m, 1H); LRMS (ESI) calculated M+H for C19H22N7O2S: 412.4. Found: 412.1.

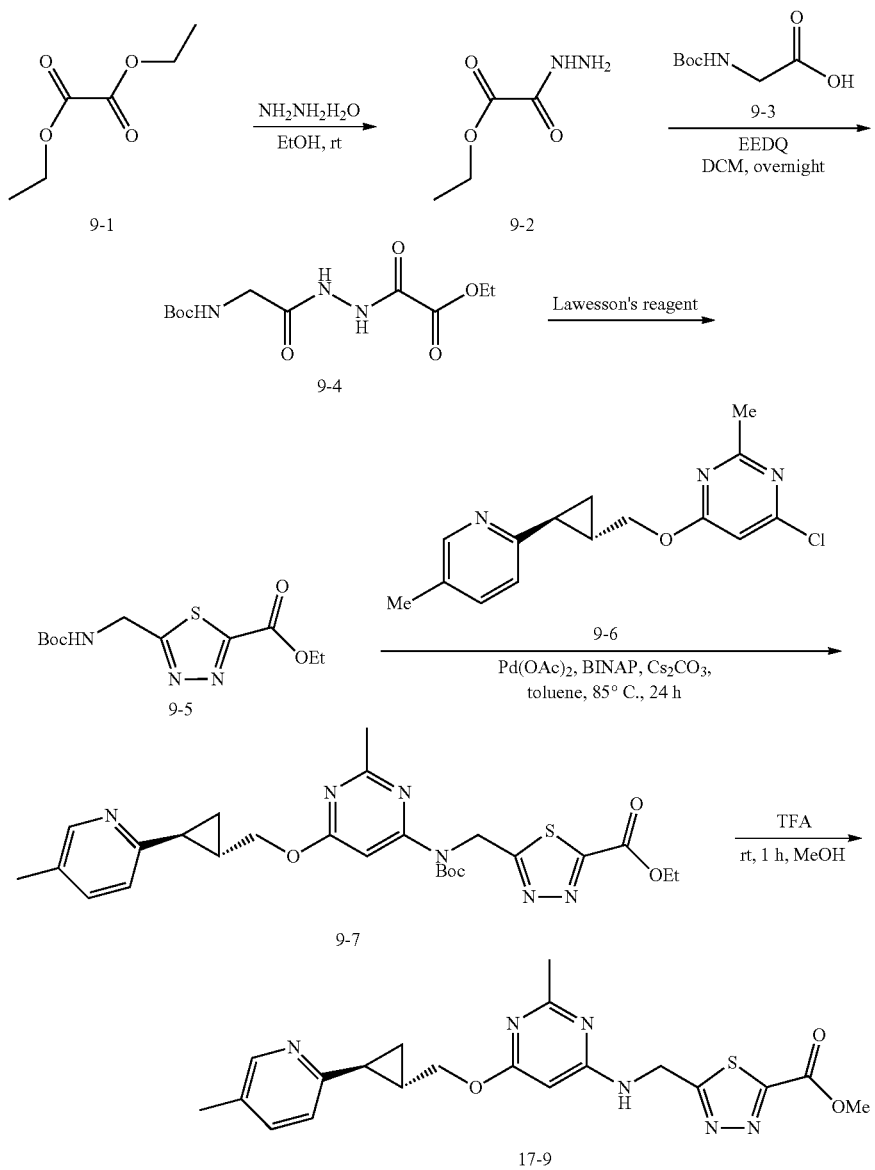

Ethyl 2-hydrazinyl-2-oxoacetate (9-2)

To a solution of diethyl oxalate (9-1) (6.0 g, 41.04 mmol) in alcohol (30 mL) was added hydrazine hydrate (2.4 mL, 49.26 mmol) dropwise at −20° C. After the addition was over, the solution was stirred for 30 min. The solution was filtered and the filtrate was evaporated to give the product as a white solid (3.0 g, 55%). The compound was used for the next step directly without further purification. LRMS (ESI) calculated M+H for C4H9N2O3: 133.1. Found: 133.3.

Ethyl 2-(2-(2-(tert-butoxycarbonylamino)acetyl) hydrazinyl)-2-oxoacetate (9-4)

To a solution of ethyl 2-hydrazinyl-2-oxoacetate (9-2) (0.516 g, 3.91 mmol) in dichloromethane (14 mL) was added EEDQ (0.78 g, 3.175 mmol) at room temperature and it was stirred for 15 min. Then 2-(tert-butoxycarbonylamino)acetic acid (9-3) (0.55 g, 3.175 mmol) was added. The mixture was stirred at room temperature for overnight. Solvent was removed under reduced pressure and the residue was purified by chromatography on silica gel with gradient eluant (PE/EA=3/1 to 1/1). The product was obtained as a white solid (0.787 g, 85%). $^1$H NMR (400 MHz, CDCl$_3$) δ 9.35 (s, 1H), 8.99 (s, 1H), 5.19 (s, 1H), 4.40 (dd, J=21.7, 7.2 Hz, 2H), 3.93 (d, J=6.1 Hz, 2H), 1.57-1.32 (m, 12H); LRMS (ESI) calculated M+Na for C11H19N3NaO6: 312.2. Found: 312.1.

Ethyl 5-((tert-butoxycarbonylamino)methyl)-1,3,4-thiadiazole-2-carboxylate (9-5)

To the solution of ethyl 2-(2-(2-(tert-butoxycarbonylamino)acetyl) hydrazinyl)-2-oxoacetate (9-4) (228 mg, 0.6913 mmol) in THF (10 mL) was added lawesson's reagent (354 mg, 0.8669 mmol). The solution was heated to reflux for 3 h. Then solvent was evaporated under reduced pressure and the residue was purified by chromatography on silica gel with the eluant (PE/EA/NEt$_3$=10/1/1%; 5/1/1%; 2/1/1%). The yellow solid was obtained as the product (520 mg, 69%). $^1$H NMR (500 MHz, CDCl$_3$) δ 5.31 (br, 1H), 4.76 (d, J=6.1 Hz, 2H), 4.51 (d, J=14, 7.1 Hz, 2H), 1.60-1.39 (m, 12H); LRMS (ESI) calculated M+H for C11H18N3O4S: 288.3; Found: 288.1.

Ethyl 5-((tert-butoxycarbonyl(2-methyl-6-(((1S,2S)-2-(5-methylpyridin-2-yl)cyclo propyl)methoxy)pyrimidin-4-yl)amino)methyl)-1,3,4-thiadiazole-2-carboxylate (9-7)

The mixture of ethyl 5-((tert-butoxycarbonylamino)methyl)-1,3,4-thiadiazole-2-carboxylate (9-5) (1.0 g, 3.48 mmol), 4-chloro-2-methyl-6-(((1S,2S)-2-(5-methylpyridin-2-yl)cyclopropyl)methoxy)pyrimidine (9-6), Pd(OAc)$_2$ (66 mg, 0.29 mmol), BINAP (199 mg, 0.319 mmol) and Cesium carbonate (1.133 g, 3.48 mmol) in toluene (10 mL) was heated to 85° C. under nitrogen for overnight. The solvent was removed under reduced pressure and the residue was purified by chromatography with gradient eluant (PE/EA=10/1; 5/1). The product was obtained as an orange syrup (1.0 g, 63%). $^1$H NMR (500 MHz, CDCl$_3$) δ 8.26 (s, 1H), 7.35 (dd, J=7.9, 1.8 Hz, 1H), 7.19 (s, 1H), 7.05 (d, J=7.9 Hz, 1H), 5.59 (s, 2H), 4.50 (q, J=7.1 Hz, 2H), 4.35 (m, 2H), 2.53 (s, 3H), 2.27 (s, 3H), 2.13-2.03 (m, 1H), 1.89-1.87 (m, 1H), 1.48-1.43 (m, 12H), 1.32-1.24 (m, 1H), 1.05-1.02 (m, 1H); LRMS (ESI) calculated M+H for C26H32N6O5S: 541.6. Found: 541.2.

Methyl 5-((2-methyl-6-(((1S,2S)-2-(5-methylpyridin-2-yl)cyclopropyl)methoxy)pyrimidin-4-ylamino)methyl)-1,3,4-thiadiazole-2-carboxylate (17-9)

The solution of ethyl 5-((tert-butoxycarbonyl(2-methyl-6-(((1S,2S)-2-(5-methylpyridin-2-yl)cyclopropyl)methoxy)pyrimidin-4-yl)amino)methyl)-1,3,4-thiadiazole-2-carboxylate (S-7) (70 mg, 0.1294 mmol) in TFA (1 mL) was stirred at room temperature for 1 h. The solvent was removed under reduced pressure and the residue was purified by reverse phase column (Waters Sunfire Prep C18 OBD, 5-75% methanol in water with 0.1% NH$_3$H$_2$O modifier) to provide product as a white solid (25 mg, 21.4%). $^1$H NMR (400 MHz, CDCl$_3$) δ 8.26 (s, 1H), 7.35 (dd, J=7.9, 1.7 Hz, 1H), 7.03 (d, J=7.9 Hz, 1H), 5.60 (s, 1H), 5.48 (s, 1H), 5.02 (d, J=6.3 Hz, 1H), 4.27 (ddd, J=24.1, 11.1, 7.0 Hz, 2H), 4.03 (s, 3H), 2.48 (d, J=5.8 Hz, 3H), 2.19 (s, 3H), 1.87-1.85 (m, 1H), 1.85-1.80 (m, 1H), 1.32-1.29 (m, 1H), 1.06-1.02 (m, 1H); LRMS (ESI) calculated M+H for C20H23N6O3S: 427.5. Found: 427.1.

2-(5-((2-Methyl-6-(((1S,2S)-2-(5-methylpyridin-2-yl)cyclopropyl)methoxy)pyrimidin-4-ylamino)methyl)-1,3,4-thiadiazol-2-yl)propan-2-ol (17-6)

To the solution of 17-9 (60 mg, 0.1364 mmol) in THF (1 mL) was added CH$_3$MgBr (3 M in ether, 0.24 mL, 0.68 mmol)

dropwise at 0° C. The mixture was brought to rt and stirred for 16 h. Then it was quenched with potassium phosphate aqueous to PH 9-10 and extracted with ethyl acetate (20 mL*3). The organic layers were combined, dried over anhydrous sodium sulfate and purified by column chromatography on silica gel (EtOAc/Hexane=1/3 to 1/2) to give the target compound (20 mg, 34%). $^1$H NMR (500 MHz, CDCl$_3$) δ 8.28 (s, 1H), 7.37 (dd, J=8.0, 2.0 Hz, 1H), 7.05 (d, J=7.9 Hz, 1H), 5.63 (s, 1H), 4.91 (d, J=6.2 Hz, 2H), 4.35-4.24 (m, 2H), 3.02 (s, 1H), 2.48 (s, 3H), 2.29 (s, 3H), 2.04 (m, 1H), 1.88-1.84 (m, 1H), 1.86 (s, 9H), 1.32-1.28 (m, 1H), 1.07-1.03 (m, 1H); LRMS (ESI) calculated M+H for C21H27N6O2S: 427.5. Found: 427.1.

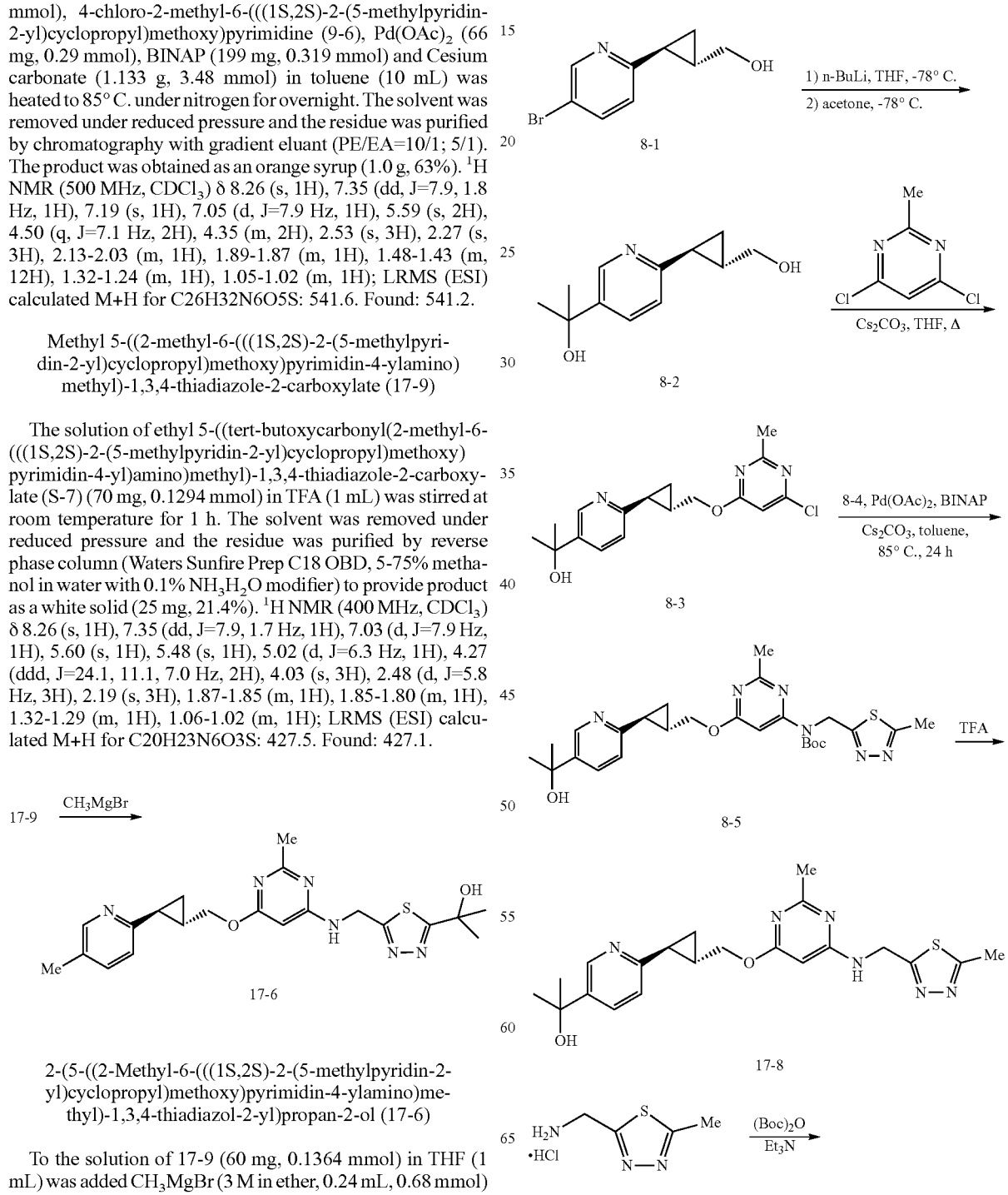

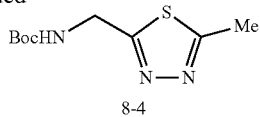

8-4

2-(6-((1S,2S)-2-(Hydroxymethyl)cyclopropyl)pyridin-3-yl)propan-2-ol (8-2)

To the solution of 8-1 (267 mg, 1.18 mmol) in THF (10 mL) was added n-BuLi (1.41 mL, 3.53 mmol) at −78° C. under nitrogen. The mixture was stirred for 1 h before acetone (0.341 mg, 5.88 mmol) was added and it was stirred for 2 h. The mixture was quenched with ammonium chloride aqueous solution and extracted with EtOAc (20 mL*4), dried over MgSO$_4$, filtered and concentrated under reduced pressure. The residue was purified by column chromatography on silica gel (Petroleum ether:ethyl acetate=3:1-1:1) to give the title product as a yellow oil (135 mg, 55%). LRMS (ES) calculated M+H for C$_6$H$_9$BrN$_2$O: 208.13. Found: 208.2.

2-(6-((1S,2S)-2-((6-chloro-2-methylpyrimidin-4-yloxy)methyl)cyclopropyl)pyridin-3-yl)propan-2-ol (8-3)

A solution of compound 8-2 (135 mg, 0.652 mmol) and 4,6-dichloro-2-methylpyrimidine (106.3 mg, 0.65 mmol) in THF (3.0 mL) was treated with Cs$_2$CO$_3$ (281 mg, 0.86 mmol) and heated to reflux for 12 h. The reaction mixture was filtrated and the filtrate was concentrated and purified directly by gradient elution on silica gel (Petroleum ether:ethyl acetate=2:1-1:1) to afford the title compound as a colorless oil (60 mg, 28%). LRMS (ES) calculated M+H for C$_{17}$H$_{20}$ClN$_3$O$_2$: 334.12. Found: 334.1.

tert-Butyl (5-methyl-1,3,4-thiadiazol-2-yl)methylcarbamate (8-4)

A solution of (5-methyl-1,3,4-thiadiazol-2-yl)methanamine hydrochloride (500 mg, 3.0 mmol), di-tert-butyl dicarbonate (794 mg, 3.64 mmol) and triethylamine (460 mg, 4.55 mmol) in CH$_2$Cl$_2$ (15.0 mL) stirred for overnight at room temperature. The mixture was diluted with EtOAc (50 mL), washed with sat. NaHCO$_3$ aq (50 mL) and brine (50 mL), dried over MgSO$_4$, filtered, and concentrated in vacuo to yield the title product (560 mg, 81%). LRMS (ES) calculated M+H for C$_9$H$_{15}$N$_3$O$_2$S: 230.09. Found: 230.2.

tert-Butyl-6-(((1S,2S)-2-(5-(2-hydroxypropan-2-yl)pyridin-2-yl)cyclopropyl)methoxy)-2-methylpyrimidin-4-yl((5-methyl-1,3,4-thiadiazol-2-yl)methyl)carbamate (8-5)

The mixture of 8-3 (60 mg, 0.18 mmol), 8-4 (50 mg, 0.22 mmol), Cs$_2$CO$_3$ (88 mg, 0.27 mmol), Pd(OAc)$_2$ (8.1 mg, 0.036 mmol), BINAP (25 mg, 0.040 mmol) in toluene (2.0 mL) was heated at 85° C. for overnight. Then the reaction mixture was diluted with EtOAc (20 mL), filtered and concentrated in vacuo to give crude product (94 mg) which was used for next step without further purification. LRMS (ES) calculated M+H for C$_{26}$H$_{34}$N$_6$O$_4$S: 527.24. Found: 527.2.

2-(6-((1S,2S)-2-((2-methyl-6-((5-methyl-1,3,4-thiadiazol-2-yl)methylamino)pyrimidin-4-yloxy)methyl)cyclopropyl)pyridin-3-yl)propan-2-ol (17-8)

Crude 8-5 mixture was treated with TFA (2.0 mL) and the mixture was stirred for 1 h at room temperature. After concentration, the residue was purified with reverse phase column (Waters Sunfire Prep C18 OBD, 5-75% methanol in water with 0.1% NH$_3$H$_2$O modifier) to give the title product (10 mg, 21%). $^1$H NMR (400 MHz, CDCl$_3$) δ 8.57 (d, J=2.0 Hz, 1H), 7.72 (dd, J=8.2, 2.3 Hz, 1H), 7.12 (d, J=8.2 Hz, 1H), 5.70 (s, 1H), 4.86 (d, J=6.2 Hz, 2H), 4.37 (dd, J=11.2, 6.4 Hz, 1H), 4.24 (dd, J=11.1, 7.4 Hz, 1H), 2.74 (s, 3H), 2.49 (s, 3H), 2.14-2.09 (m, 1H), 1.89 (d, J=6.5 Hz, 1H), 1.58 (s, 6H), 1.33 (dd, J=9.0, 4.6 Hz, 1H), 1.10-1.03 (m, 1H). LRMS (ES) calculated M+H for C$_{21}$H$_{26}$N$_6$O$_2$S: 427.18. Found: 427.2.

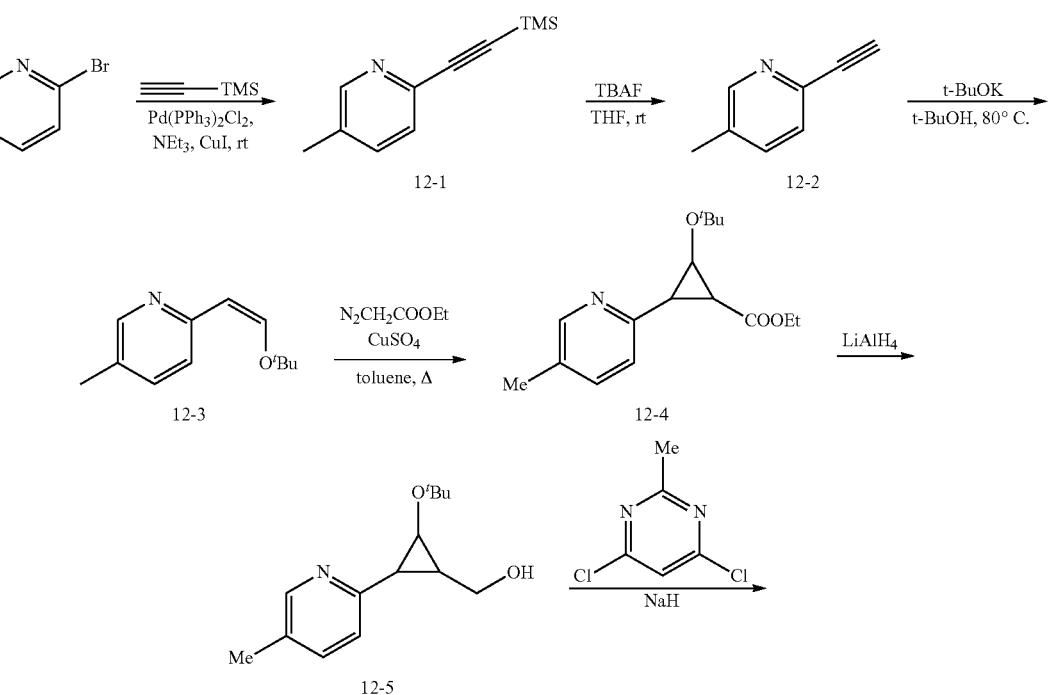

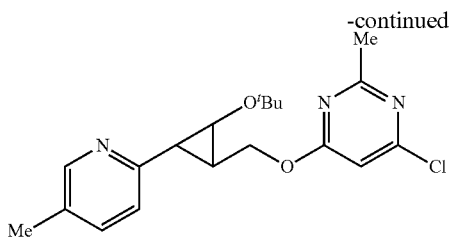
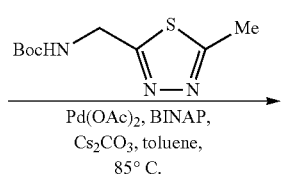

12-6

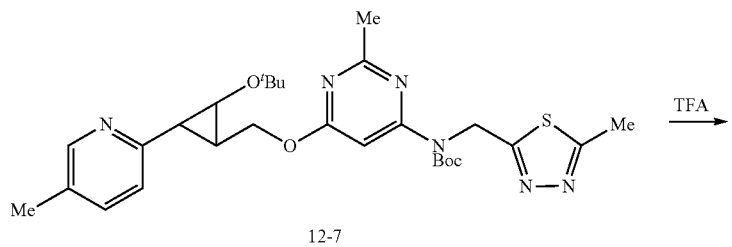

12-7

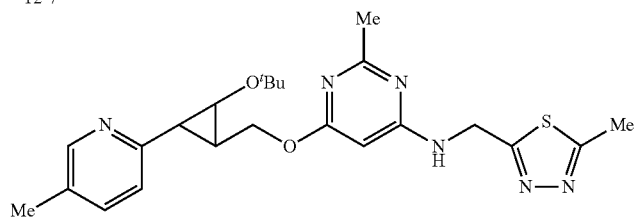

17-12

5-Methyl-2-((trimethylsilyl)ethynyl)pyridine (12-1)

The mixture of 2-bromo-5-methylpyridine (5.0 g, 29.1 mmol), ethynyltrimethylsilane (3.42 g, 34.88 mmol), Copper iodide (0.61 g, 332 mg) and Pd(PPh$_3$)$_2$Cl$_2$ (0.61 g, 0.871 mmol) was dissolved in triethylamine (6.4 mL, 261 mmol). The solution was purged with N$_2$ 3 times. The solution was stirred for overnight under 25° C. The solvent was removed under reduced pressure. The residue was separated by silca gel chromatography with the eluent of PE/EA=20/1. The product was obtained as a yellow solid (4.15 g, 76%). $^1$H NMR (400 MHz, CDCl$_3$) δ 8.41 (s, 1H), 7.46 (dd, J=7.9, 1.5 Hz, 1H), 7.36 (d, J=7.9 Hz, 1H), 2.35 (s, 3H), 0.28 (s, 9H); LRMS (ES) calculated M+H for C11H16NSi: 190.3. Found: 190.2.

2-Ethynyl-5-methylpyridine (12-2)

To the solution of 5-methyl-2-((trimethylsilyl)ethynyl)pyridine (12-1) (4.16 g, 22 mmol) in THF was added tetra-n-butylammonium fluoride (44 mL, 44 mmol) at rt and the solution was stirred for 1 h. The solvent was removed under reduced pressure. The residue was purified by silca gel chromatography with eluent of PE/EA (20/1). The product was obtained as yellow oil (1.78 g, 69%). $^1$H NMR (400 MHz, CDCl$_3$) δ 8.42 (s, 1H), 7.46 (d, J=7.9 Hz, 1H), 7.38 (d, J=7.9 Hz, 1H), 3.10 (s, 1H), 2.35 (s, 3H); LRMS (ES) calculated M+H for C8H8N, 118.2. Found: 118.3.

(Z)-2-(2-tert-butoxyvinyl)-5-methylpyridine (12-3)

To the solution of 2-ethynyl-5-methylpyridine (12-2) (1.38 g, 11.8 mmol) in tert-butyl alcohol (4.734 g, 63.9 mmol) was added potassium tert-butoxide (531 mg, 4.7 mmol) under nitrogen. The solution was heated to reflux for overnight. The solvent was removed under reduced pressure. The residue was purified by silca gel chromatography with the gradient eluent (PE/EA/NEt$_3$=10/1/1%; 5/1/1%). The product (Z)-2-(2-tert-butoxyvinyl)-5-methylpyridine (12-3) was obtained as yellow oil (1.40 g, 62%) and by product was (E)-2-(2-tert-butoxyvinyl)-5-methylpyridine (0.3 g, 13%).

(12-3): $^1$H NMR (400 MHz, CDCl$_3$) δ 8.31 (s, 1H), 7.94 (d, J=8.2 Hz, 1H), 7.42 (d, J=1.5 Hz, 1H), 6.63 (d, J=7.3 Hz, 1H), 5.53 (d, J=7.3 Hz, 1H), 2.28 (s, 3H), 1.40 (s, 9H); LRMS (ES) calculated M+H for C12H18NO: 192.3. Found: 192.3.

(E)-2-(2-tert-butoxyvinyl)-5-methylpyridine $^1$H NMR (400 MHz, CDCl$_3$) δ 8.28 (s, 1H), 7.60 (d, J=12.0 Hz, 1H), 7.32 (dd, J=8.0, 1.5 Hz, 1H), 6.89 (d, J=8.0 Hz, 1H), 5.97 (d, J=12.0 Hz, 1H), 2.27 (s, 3H), 1.39 (s, 9H); LRMS (ES) calculated M+H for C12H18NO: 192.3. Found: 192.3.

Ethyl 2-tert-butoxy-3-(5-methylpyridin-2-yl)cyclopropanecarboxylate (12-4)

The solution of (Z)-2-(2-tert-butoxyvinyl)-5-methylpyridine (12-3) (1.20 g, 6.27 mmol) in toluene (20 mL) and anhydrous copper sulfate (100 mg, 0.63 mmol) was heated to 75° C. Then the solution of ethyl diazoacetate (2.17 g, 18.8 mmol) in toluene (10 mL) was added dropwise over 2 h. It was heated for another 2 h after the addition was completed. The mixture was restored to room temperature for overnight. The solvent was removed under reduced pressure and the residue was purified by silca gel chromatography with gradient eluent (PE/EA=40/1; 20/1; 10/1). The product was obtained as a yellow oil (500 mg, 34%). LRMS (ES) calculated M+H for C16H24NO3: 278.3. Found: 278.2.

(2-tert-butoxy-3-(5-methylpyridin-2-yl)cyclopropyl)methanol (12-5)

The solution of ethyl 2-tert-butoxy-3-(5-methylpyridin-2-yl)cyclopropanecarboxylate (12-4) (350 mg, 1.26 mmol) in THF (2 mL) was cooled to 0° C. Then lithium aluminium tetrahydride (72 mg, 1.89 mmol) was added to the solution at 0° C. and it was stirred for 30 min before restored to the room temperature for 1 h. The reaction was quenched in sequence with 0.1 mL water, 0.05 mL 15% NaOH aqueous, 0.1 mL water. The resulting mixture was dried over anhydrous sodium sulfate and filtered. The filtrate was concentrated under reduced pressure and purified by Pre-TLC (PE/EA=1/1). The product was obtained as a white solid (200 mg, 68%). $^1$H NMR (400 MHz, MeOD) δ 8.24 (s, 1H), 7.55 (dd, J=8.2, 1.7 Hz, 1H), 7.11 (d, J=8.2 Hz, 1H), 3.66-3.58 (m, 3H), 2.33 (s, 3H), 2.13 (t, J=6.6 Hz, 1H), 1.80 (dd, J=6.4, 3.7 Hz, 1H), 1.06 (s, 9H); LRMS (ES) calculated M+H for C14H22NO2: 236.3. Found: 236.2.

4-((2-Tert-butoxy-3-(5-methylpyridin-2-yl)cyclopropyl)methoxy)-6-chloro-2-methylpyrimidine (12-6)

To a solution of (2-tert-butoxy-3-(5-methylpyridin-2-yl)cyclopropyl)-methanol (12-5) (130 mg, 0.55 mmol) in THF, sodium hydride (28 mg, 0.69 mmol) was added at 0° C. and it was allowed to stir for 30 min whereupon a solution of 4,6-dichloro-2-methylpyrimidine (113 mg, 0.69 mmol) in THF was added. The solution was heated to reflux overnight. After cooling, it was quenched with water, extracted with EtOAc, dried over sodium sulfate, concentrated under reduced pressure and purified by Pre-TLC (PE/EA=1:1) to afford the product as a white solid (111 mg, 56%). $^1$H NMR (500 MHz, CDCl$_3$) δ 8.35 (s, 1H), 7.41 (d, J=6.6 Hz, 1H), 7.04 (d, J=8.1 Hz, 1H), 6.59 (s, 1H), 4.49-4.40 (m, 2H), 3.62 (dd, J=6.9, 3.6 Hz, 1H), 2.60 (s, 3H), 2.30 (s, 3H), 2.27 (m, 1H), 2.04 (dd, J=6.7, 3.7 Hz, 1H), 1.08 (s, 9H); LRMS (ES) calculated M+H for C19H25ClN3O2: 362.8. Found: 362.1.

Tert-Butyl 6-((2-tert-butoxy-3-(5-methylpyridin-2-yl)cyclopropyl)methoxy)-2-methylpyrimidin-4-yl ((5-methyl-1,3,4-thiadiazol-2-yl)methyl)carbamate (12-7)

The mixture of 12-6 (160 mg, 0.4421 mmol), tert-butyl (5-methyl-1,3,4-thiadiazol-2-yl)methylcarbamate (122 mg, 0.53 mmol), BINAP (31 mg, 0.049 mmol) and cesium carbonate (173 mg, 0.53 mmol) in toluene (2 mL) was stirred for 5 min before Pd(OAc)$_2$ (10 mg, 0.044 mmol) was added. The mixture was degassed with nitrogen for 5 min, then it was heated to 80° C. for overnight. The solvent was removed under reduced pressure and the residue was purified by Pre-TLC (PE/EA=1/1). The product was obtained as a white solid (120 mg, 49%). $^1$H NMR (400 MHz, CDCl$_3$) δ 8.34 (s, 1H), 7.39 (d, J=7.9 Hz, 1H), 7.17 (s, 1H), 7.03 (d, J=8.1 Hz, 1H), 5.52 (s, 2H), 4.52-4.18 (m, 2H), 3.64 (dd, J=6.8, 3.6 Hz, 1H), 2.73 (s, 1H), 2.69 (s, 3H), 2.52 (s, 3H), 2.30 (s, 3H), 2.27 (m, 1H), 2.04 (m, 1H), 1.50 (s, 9H), 1.07 (s, 9H); LRMS (ES) calculated M+H for C28H39N6O4S: 555.7. Found: 555.1.

6-((2-Tert-butoxy-3-(5-methylpyridin-2-yl)cyclopropyl)methoxy)-2-methyl-N-((5-methyl-1,3,4-thiadiazol-2-yl)methyl)pyrimidin-4-amine (17-12)

The solution of 12-7 (41 mg, 0.074 mmol) in TFA (0.5 mL) was stirred for 1 h at rt. The excess TFA was removed under reduced pressure. The residue was dissolved in dichloromethane (10 mL) and adjusted to pH=9-10 with saturated NaHCO$_3$ aqueous solution. The mixture was extracted with EtOAc, dried over sodium sulfate, concentrated under reduced pressure and purified by reverse phase column (Waters Sunfire Prep C18 OBD, 5-95% methanol in water with 0.1% NH$_3$H$_2$O modifier). The product was obtained as a white solid (22 mg, 65%). $^1$H NMR (500 MHz, CDCl$_3$) δ 8.36 (s, 1H), 7.51 (s, 1H), 7.12 (d, J=4.8 Hz, 1H), 5.63 (s, 1H), 5.43 (s, 1H), 4.91 (d, J=6.3 Hz, 2H), 4.36 (d, J=6.8 Hz, 2H), 3.66 (s, 1H), 2.73 (s, 3H), 2.47 (s, 3H), 2.33 (m, 4H), 2.03 (m, 1H), 1.06 (s, 9H); LRMS (ES) calculated M+H for C23H31N6O2S: 455.6. Found:455.2.

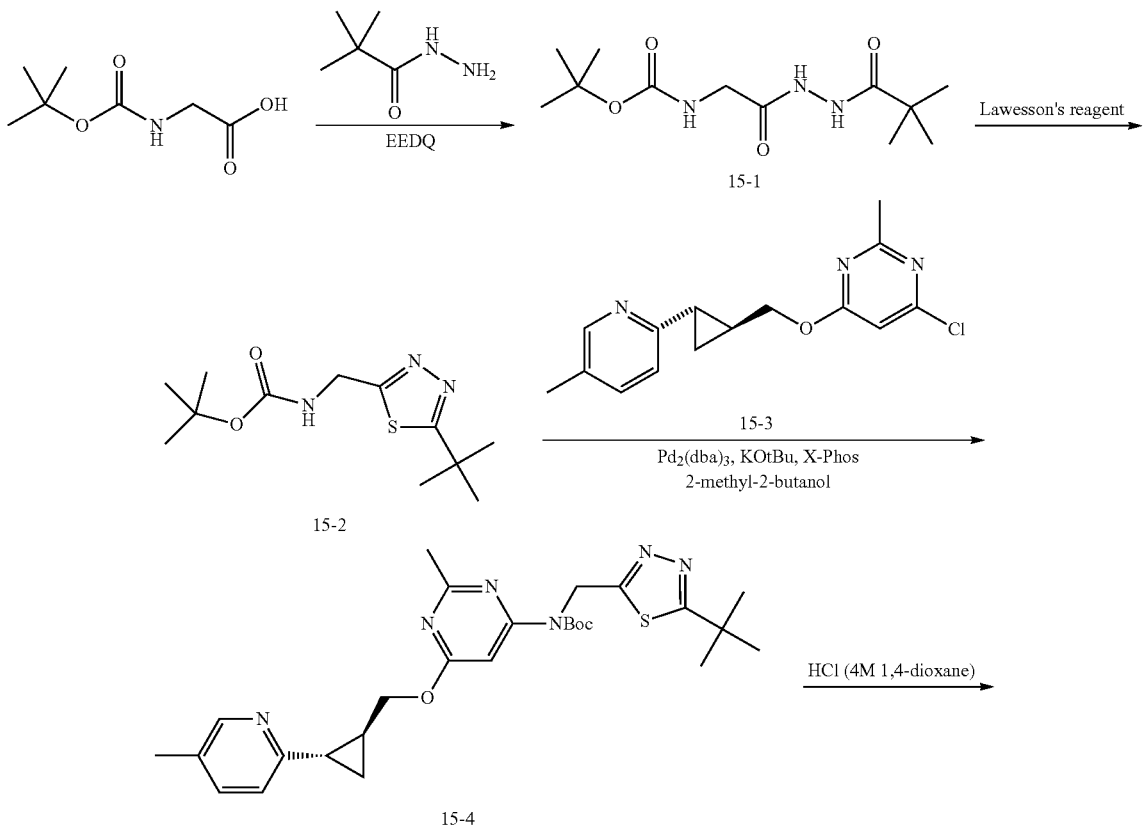

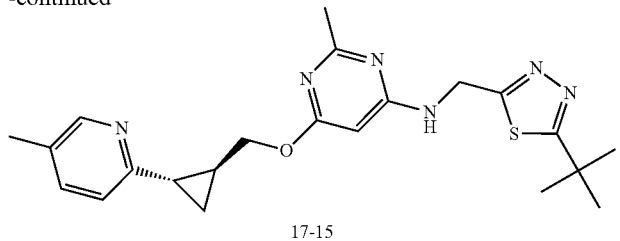

17-15

Tert-butyl 2-oxo-2-(2-pivaloylhydrazinyl)ethylcarbamate (15-1)

A mixture of 2-(tert-butoxycarbonylamino)acetic acid (200 mg, 1.14 mmol) and EEDQ (282 mg, 1.26 mmol) in DCM (5 mL) was stirred at room temperature for 15 min, then pivalohydrazide (145 mg, 1.26 mmol) was added and the mixture was continued stirring overnight. The reaction mixture was concentrated and purified by reverse phase chromatography to afford the title compound (100 mg, 32%) as a white solid. $^1$H NMR (400 MHz, CDCl$_3$) δ 8.98 (s, 1H), 8.28 (s, 1H), 5.24 (s, 1H), 3.92 (d, J=5.8 Hz, 2H), 1.46 (s, 9H), 1.26 (s, 9H); LRMS (ES) calculated M+Na for $C_{21}H_{25}N_5O_4$: 296.2. Found: 296.0.

Tert-butyl (5-tert-butyl-1,3,4-thiadiazol-2-yl)methylcarbamate (15-2)

To a solution of 15-1 (100 mg, 0.37 mmol) in THF (10 mL) was added lawesson's reagent (153 mg, 0.38 mmol) and it was refluxed for 3 h. The reaction mixture was concentrated and purified by gradient elution on silica gel (0 to 50% EtOAc in petroleum) to afford the title compound (93 mg, 92%). LRMS (ES) calculated M+H for $C_{12}H_{21}N_3O_2S$: 272.4. Found: 272.2.

Tert-butyl(5-tert-butyl-1,3,4-thiadiazol-2-yl)methyl (2-methyl-6-(((1S,2S)-2-(5-methylpyridin-2-yl)cyclopropyl)methoxy)pyrimidin-4-yl)carbamate (15-4)

15-2 (181 mg, 0.67 mmol) and (15-3) (200 mg, 0.69 mmol) was combined in 2-Methyl-2-butanol (3 ml) and purged with N$_2$ for 3 min. The solution was then warmed up to 50° C. After addition of KO$^t$Bu (92 mg, 0.83 mmol), X-Phos (16 mg, 0.03 mmol) and Pd$_2$(dba)$_3$ (31 mg, 0.03 mmol), the mixture was heated at 60° C. for 60 min. Then it was quenched with sat. NH$_4$Cl (2 mL) and extracted with EtOAc (15 mL×4). Combined organic phases were washed with water (5 mL) and brine (5 mL), dried and concentrated. The residue was purified by gradient elution on silica gel (20% to 30% EtOAc/Petroleum) to afford the title compound (70 mg, 20%). LRMS (ES) calculated M+H for $C_{27}H_{36}N_6O_3S$:525.7. Found: 525.0.

N-((5-tert-butyl-1,3,4-thiadiazol-2-yl)methyl)-2-methyl-6-(((1R,2R)-2-(5-methylpyridin-2-yl)cyclopropyl)methoxy)pyrimidin-4-amine (17-15)

15-4 (40 mg, 0.06 mmol) was treated with HCl (4 M in 1,4-dioxane) (2 mL) and the mixture was stirred at room temperature for 6 h. Then it was concentrated, diluted with water (1 mL), and adjusted to pH 11 with aq NaOH (4 N). The resulting mixture was extracted with DCM (10 mL×4) and the organic layer was dried over Na$_2$SO$_4$, concetrated to afford the title compound (30 mg, 93%). $^1$H NMR (400 MHz, MeOD) δ 8.08 (s, 1H), 7.40 (d, J=7.8 Hz, 1H), 7.03 (d, J=8.0 Hz, 1H), 5.60 (s, 1H), 4.16 (dd, J=10.9, 6.5 Hz, 1H), 4.03 (dd, J=10.8, 7.5 Hz, 1H), 3.02 (s, 2H), 2.26 (s, 3H), 2.18 (s, 3H), 2.05-1.96 (m, 1H), 1.69 (d, J=6.2 Hz, 1H), 1.34 (s, 9H), 1.15-1.04 (m, 1H), 1.04-0.91 (m, 1H). LRMS (ES) calculated M+H for $C_{22}H_{28}N_6OS$: 425.6. Found: 425.2.

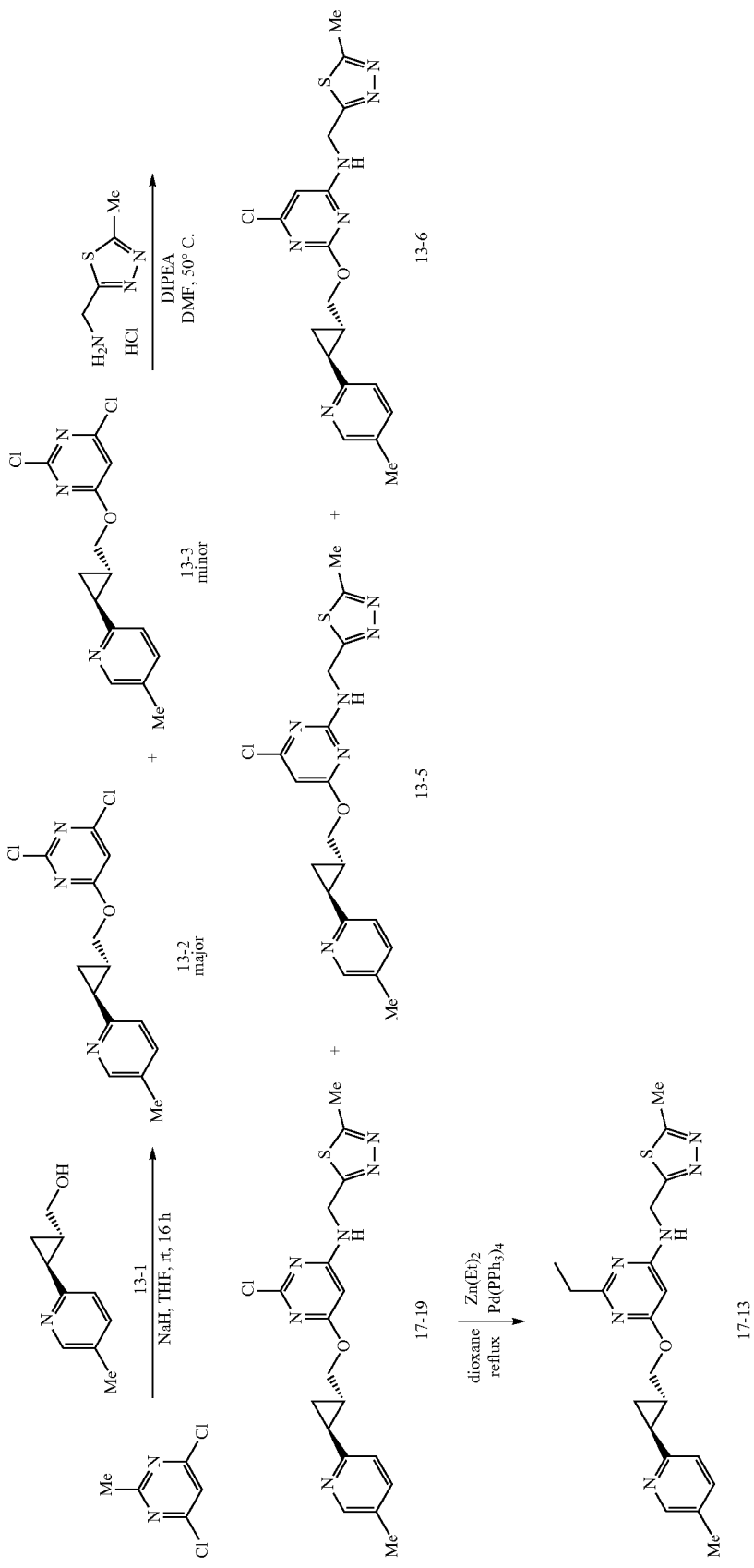

2-chloro-N-((5-methyl-1,3,4-thiadiazol-2-yl)methyl)-6-(((1S,2S)-2-(5-methylpyridin-2-yl)cyclopropyl)methoxy)pyrimidin-4-amine (17-19) and 4-chloro-N-((5-methyl-1,3,4-thiadiazol-2-yl)methyl)-6-(((1S,2S)-2-(5-methylpyridin-2-yl)cyclopropyl)methoxy)pyrimidin-2-amine (13-5) and 6-chloro-N-((5-methyl-1,3,4-thiadiazol-2-yl)methyl)-2-(((1S,2S)-2-(5-methylpyridin-2-yl)cyclopropyl)methoxy)pyrimidin-4-amine (13-6)

A 50 mL reaction flask was charged with (((1S,2S)-2-(5-methylpyridin-2-yl)cyclopropyl)methanol (13-1) (890 mg, 5.5 mmol), NaH (196 mg, 8.2 mmol) and THF (20 mL). The mixture was stirred at rt for 30 min. Then it was added to the solution of 2,4,6-trichloropyrimidine (1 g, 5.6 mmol) in THF (20 mL) and the mixture was stirred at rt for 16 h. Aqueous sodium bicarbonate (20 mL) was carefully added and the mixture was extracted with EtOAc (2×50 mL). The combined organics were dried over MgSO$_4$, filtered and concentrated to afford the title compound as a yellow oil, which was one spot on TLC and one peak on LCMS. LRMS (ES) calculated M+H for C$_{14}$H$_{14}$Cl$_2$N$_3$O: 310.0. Found: 310.0. This crude 13-2 and 13-3 mixture was used in the subsequent step without further purification.

A 100 mL flask was charged with the above mixture of 13-2 and 13-3 (2.0 g, 6.0 mmol), (5-methyl-1,3,4-thiadiazol-2-yl)methanamine hydrochloride (990 mg, 6.0 mmol), DIPEA (2.4 g, 17.6 mmol) and DMF (30 mL). The reaction mixture was heated to 50° C. with stirring for 24 h. Water (100 mL) was added and the mixture was extracted with EtOAc (2×50 mL). The combined organics were washed with brine (30 mL), dried over Na$_2$SO$_4$, filtered, and concentrated in vacuo. The resulting residue was purified by silica gel column chromatogaphy (Petroleum ether/EtOAc=1/2) to afford 17-19 (70 mg, 3%): $^1$H NMR (400 MHz, DMSO) δ 8.40 (s, 1H), 8.23 (s, 1H), 7.45 (dd, J=7.9, 1.7 Hz, 1H), 7.18 (d, J=7.9 Hz, 1H), 5.85 (s, 1H), 4.80 (d, J=3.6 Hz, 2H), 4.24 (dd, J=11.1, 6.8 Hz, 1H), 4.16 (dd, J=11.1, 7.6 Hz, 1H), 2.67 (s, 3H), 2.22 (s, 3H), 2.17-2.08 (m, 1H), 1.76-1.67 (m, 1H), 1.14 (m, J=8.7, 4.4 Hz, 1H), 1.04-0.97 (m, 1H). ppm; LRMS m/z (M+H) 403.0 found, 403.1 required. 13-5 (860 mg, 36%): $^1$H NMR (400 MHz, DMSO) δ 8.41 (d, J=30.9 Hz, 1H), 8.22 (s, 1H), 7.45 (d, J=6.9 Hz, 1H), 7.16 (s, 1H), 6.24 (s, 1H), 4.76 (s, 2H), 4.27 (d, J=33.3 Hz, 2H), 2.65 (s, 3H), 2.22 (s, 3H), 2.18-1.98 (m, 1H), 1.70 (m, 1H), 1.12 (m, 1H), 0.97 (m, 1H). ppm; LRMS m/z (M+H) 403.0 found, 403.1 required. 13-6 (750 mg, 30%): $^1$H NMR (400 MHz, DMSO) δ 8.58 (s, 1H), 8.23 (s, 1H), 7.45 (dd, J=7.9, 1.7 Hz, 1H), 7.18 (d, J=7.9 Hz, 1H), 6.28 (s, 1H), 4.86 (d, J=5.5 Hz, 2H), 4.28 (dd, J=11.3, 6.7 Hz, 1H), 4.13 (dd, J=11.3, 7.7 Hz, 1H), 2.66 (s, 3H), 2.22 (s, 3H), 2.09 (m, 1H), 1.72 (m, 1H), 1.12 (m, 1H), 1.03-0.94 (m, 1H). LRMS m/z (M+H) 403.0 found, 403.1 required.

2-ethyl-N-((5-methyl-1,3,4-thiadiazol-2-yl)methyl)-6-(((1S,2S)-2-(5-methylpyridin-2-yl)cyclopropyl)methoxy)pyrimidin-4-amine (17-13)

Diethylzinc (0.4 mL, 0.4 mmol)) was added dropwise to a solution of (17-19) (70 mg, 0.17 mmol) and Pd(dppf)Cl$_2$ (7 mg, 0.009 mmol) in dioxane (5 mL). The mixture was stirred at rt for 2 h then at reflux for 16 h under argon. The mixture was poured into sat. NaCl aq. and extracted with EtOAc (3×20 mL). The combined organic phases were washed with NaCl (sat., aq.; 100 mL), dried over Na$_2$SO$_4$ and concentrated. The residue was purified by Pre-TLC (Petroleum ether/EtOAc=1/2) to give the title compound (40 mg, 60%). $^1$H NMR (500 MHz, CD3OD) δ 8.06 (s, 1H), 7.37 (dd, J=8.0, 1.8 Hz, 1H), 7.00 (d, J=8.0 Hz, 1H), 5.59 (s, 1H), 4.77 (d, J=6.2 Hz, 2H), 4.18 (dt, J=10.9, 5.4 Hz, 1H), 4.04 (dd, J=10.9, 7.4 Hz, 1H), 2.59 (d, J=7.5 Hz, 3H), 2.52 (q, J=7.6 Hz, 2H), 2.17 (s, 3H), 2.02-1.96 (m, 1H), 1.71-1.65 (m, 1H), 1.15-1.05 (m, 4H), 1.00-0.93 (m, 1H); LRMS m/z (M+H) 397.1 found, 397.1 required.

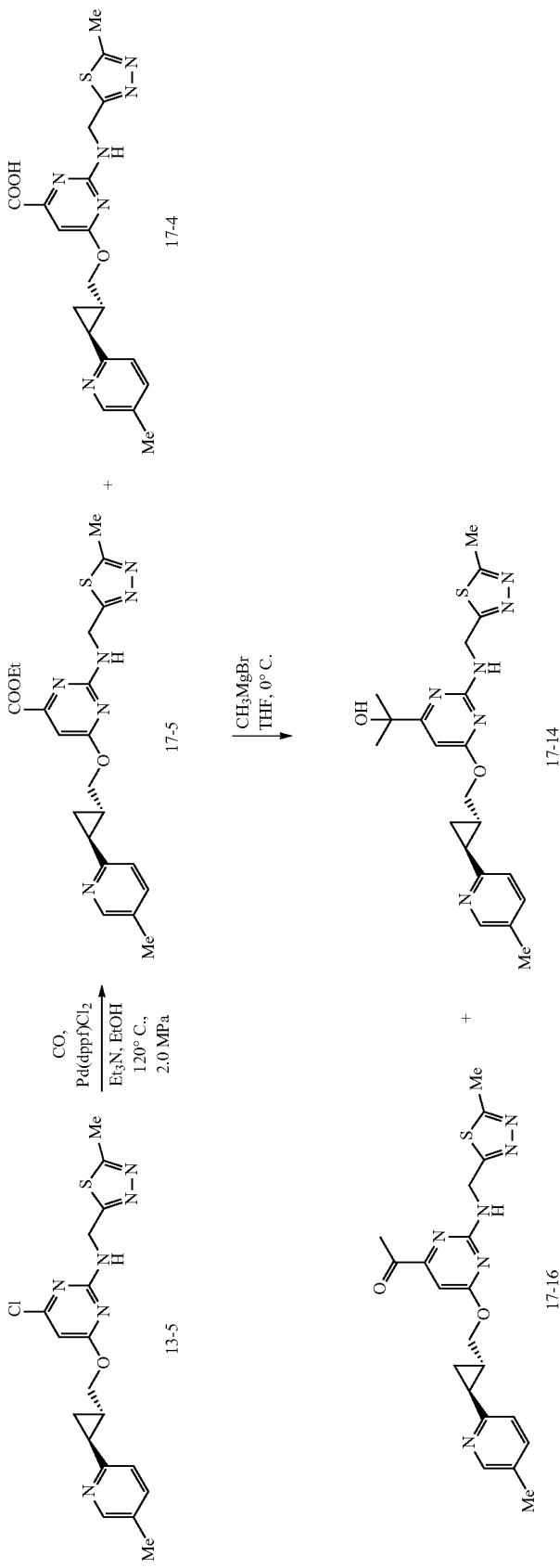

ethyl2-((5-methyl-1,3,4-thiadiazol-2-yl)methylamino)-6-(((1S,2S)-2-(5-methylpyridin-2-yl)cyclopropyl)methoxy)pyrimidine-4-carboxylate (17-5)

4-chloro-N-((5-methyl-1,3,4-thiadiazol-2-yl)methyl)-6-(((1S,2S)-2-(5-methylpyridin-2-yl)cyclopropyl)methoxy)pyrimidin-2-amine (13-5) (567 mg, 1.4 mmol), Pd(dppf)Cl$_2$ (57 mg, 0.07 mmol), was suspended in EtOH (60 mL) and Et$_3$N (6 mL) in a steal pressure vessel. The mixture was heated at 120° C. under 2.0 MPa pressure of carbon monoxide for 36 h. The mixture was concentrated and purified by Prep-HPLC to give 5 (250 mg, 41%) and 17-4 (110 mg, 20%). 17-5: $^1$H NMR (400 MHz, DMSO) δ 8.22 (s, 1H), 7.44 (d, J=7.2 Hz, 1H), 7.17 (s, 1H), 6.58 (s, 1H), 4.79 (d, J=6.0 Hz, 2H), 4.41-4.17 (m, 4H), 2.64 (s, 4H), 2.22 (s, 3H), 2.12-2.01 (m, 1H), 1.73 (m, 1H), 1.28 (t, J=7.1 Hz, 3H), 1.12 (m, 1H), 0.97 (m, 1H). LRMS m/z (M+H) 441.1 found, 441.1 required. 17-4: $^1$H NMR (400 MHz, MeOD) δ 8.05 (s, 1H), 7.36 (d, J=7.1 Hz, 1H), 6.98 (d, J=8.0 Hz, 1H), 5.88 (s, 1H), 4.87 (s, 3H), 4.28 (m, 2H), 2.58 (s, 3H), 2.17 (s, 3H), 2.05 (m, 2H), 1.67 (m, 1H), 1.11 (m, 1H), 0.98 (m, 1H). LRMS m/z (M+H) 413.1 found, 413.1 required.

2-(2-((5-methyl-1,3,4-thiadiazol-2-yl)methylamino)-6-(((1S,2S)-2-(5-methylpyridin-2-yl)cyclopropyl)methoxy)pyrimidin-4-yl)propan-2-ol (17-14)

A 50 mL reaction flask was charged with ethyl-((5-methyl-1,3,4-thiadiazol-2-yl)methylamino)-6-(((1S,2S)-2-(5-methylpyridin-2-yl)cyclopropyl)methoxy)pyrimidine-4-carboxylate (17-5) (100 mg, 0.23 mmol) and THF (5 mL) and cooled to 0° C. Then methylmagnesium bromide (0.57 mL, 1.0 M in THF, 0.57 mmol) was added dropwise to the mixture. The mixture was stirred at room temperature for 2 h. The mixture was filtered, concentrated and purified by Pre-TLC (Petroleum ether/EtOAc=0/1) to give 17-14 (30 mg, 30%) and 17-16 (19 mg, 20%). 17-14: $^1$H NMR (400 MHz, CD3OD) δ 8.41 (s, 1H), 8.19 (d, J=8.4 Hz, 1H), 7.50 (d, J=8.5 Hz, 1H), 6.40 (s, 1H), 5.00 (s, 2H), 4.46 (dd, J=11.5, 6.6 Hz, 1H), 4.38 (d, J=6.8 Hz, 1H), 2.64 (s, 3H), 2.39 (d, J=8.5 Hz, 3H), 2.35 (dd, J=8.6, 4.8 Hz, 1H), 1.99 (dd, J=12.8, 6.6 Hz, 1H), 1.53-1.32 (m, 8H); LRMS m/z (M+H) 427.1 found, 427.1 required. 17-16: $^1$H NMR (500 MHz, MeOD) δ 8.07 (s, 1H), 7.39 (dd, J=8.0, 1.9 Hz, 1H), 7.01 (d, J=8.0 Hz, 1H), 6.44 (s, 1H), 4.81 (d, J=9.4 Hz, 2H), 4.27 (m, 1H), 4.20 (m, 1H), 2.59 (d, J=4.1 Hz, 3H), 2.41 (s, 3H), 2.18 (s, 3H), 2.02 (m, 1H), 1.68 (m, 1H), 1.13 (m, 1H), 0.96 (m, 1H); LRMS m/z (M+H) 411.2 found, 411.1 required.

TABLE 8

The compounds in Table 8 were prepared in accordance with the example 17 below or an analogous manner to the examples of example 17, using the appropriate starting materials.

| Cpd. | Structure | Name | LRMS (M + H) |
| --- | --- | --- | --- |
| 17-1 | 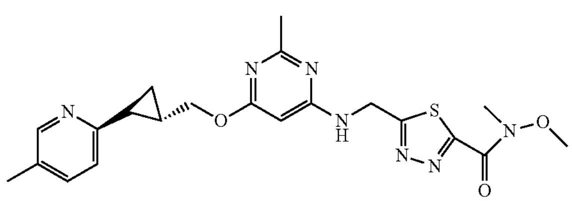 | N-methoxy-N-methyl-5-((2-methyl-6-(((1S,2S)-2-(5-methylpyridin-2-yl)cyclopropyl)methoxy)pyrimidin-4-ylamino)methyl)-1,3,4-thiadiazole-2-carboxamide | 456.5 |
| 17-2 | 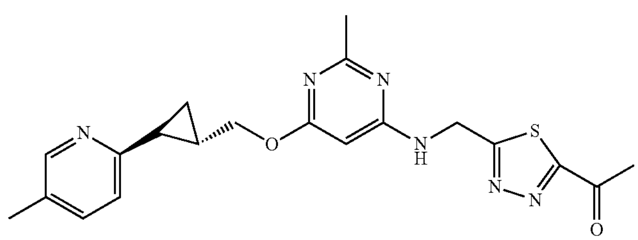 | 1-(5-((2-methyl-6-(((1S,2S)-2-(5-methylpyridin-2-yl)cyclopropyl)methoxy)pyrimidin-4-ylamino)methyl)-1,3,4-thiadiazol-2-yl)ethanone | 411.5 |
| 17-3 | 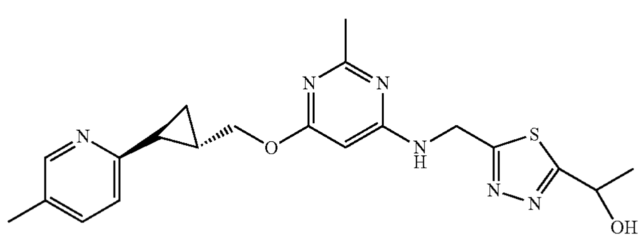 | 1-(5-((2-methyl-6-(((1S,2S)-2-(5-methylpyridin-2-yl)cyclopropyl)methoxy)pyrimidin-4-ylamino)methyl)-1,3,4-thiadiazol-2-yl)ethanol (ent1) | 413.5 |

TABLE 8-continued

The compounds in Table 8 were prepared in accordance with the example 17 below or an analogous manner to the examples of example 17, using the appropriate starting materials.

| Cpd. | Structure | Name | LRMS (M + H) |
|---|---|---|---|
| 17-4 | 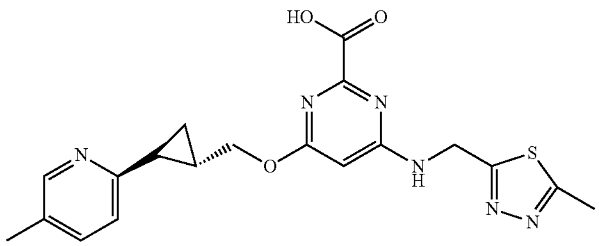 | 4-((5-methyl-1,3,4-thiadiazol-2-yl)methylamino)-6-(((1R,2R)-2-(5-methylpyridin-2-yl)cyclopropyl)methoxy)pyrimidine-2-carboxylic acid | 413.1 found, 413.1 required |
| 17-5 | 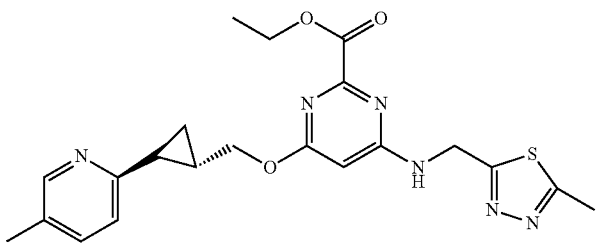 | ethyl 4-((5-methyl-1,3,4-thiadiazol-2-yl)methylamino)-6-(((1R,2R)-2-(5-methylpyridin-2-yl)cyclopropyl)methoxy)pyrimidine-2-carboxylate | 441.1 found, 441.1 required |
| 17-6 | 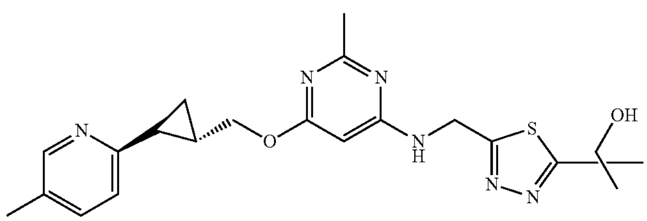 | 2-(5-((2-methyl-6-(((1S,2S)-2-(5-methylpyridin-2-yl)cyclopropyl)methoxy)pyrimidin-4-ylamino)methyl)-1,3,4-thiadiazol-2-yl)propan-2-ol | 427.5 |
| 17-8 | 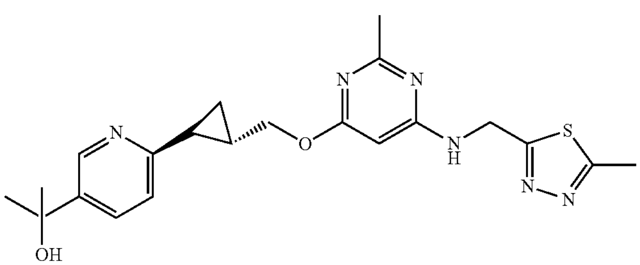 | 2-(6-((1S,2S)-2-((2-methyl-6-((5-methyl-1,3,4-thiadiazol-2-yl)methylamino)pyrimidin-4-yloxy)methyl)cyclopropyl)pyridin-3-yl)propan-2-ol | 427.2 |
| 17-9 | 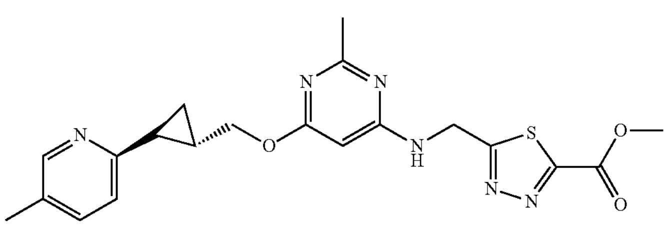 | methyl 5-((2-methyl-6-(((1S,2S)-2-(5-methylpyridin-2-yl)cyclopropyl)methoxy)pyrimidin-4-ylamino)methyl)-1,3,4-thiadiazole-2-carboxylate | 427.5 |
| 17-10 | 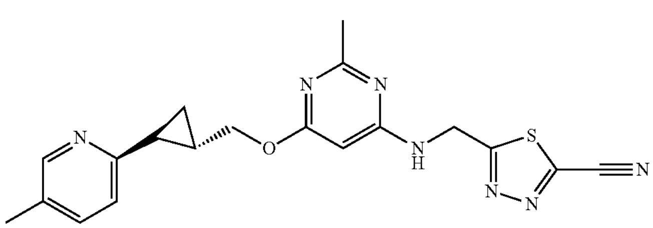 | 5-((2-methyl-6-(((1S,2S)-2-(5-methylpyridin-2-yl)cyclopropyl)methoxy)pyrimidin-4-ylamino)methyl)-1,3,4-thiadiazole-2-carbonitrile | 394.4 |

TABLE 8-continued

The compounds in Table 8 were prepared in accordance with the example 17 below or an analogous manner to the examples of example 17, using the appropriate starting materials.

| Cpd. | Structure | Name | LRMS (M + H) |
|---|---|---|---|
| 17-11 | 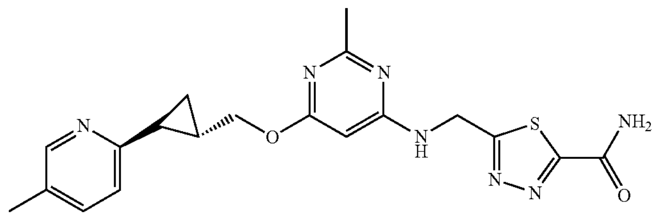 | 5-((2-methyl-6-(((1S,2S)-2-(5-methylpyridin-2-yl)cyclopropyl)methoxy)pyrimidin-4-ylamino)methyl)-1,3,4-thiadiazole-2-carboxamide | 412.4 |
| 17-12 | 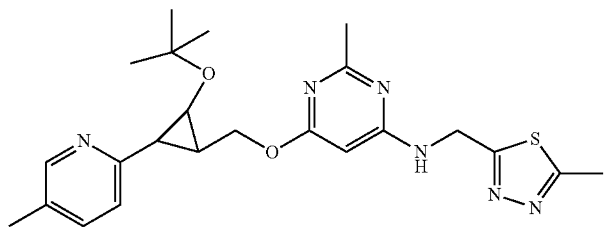 | 6-(((1S,3S)-2-tert-butoxy-3-(5-methylpyridin-2-yl)cyclopropyl)methoxy)-2-methyl-N-((5-methyl-1,3,4-thiadiazol-2-yl)methyl)pyrimidin-4-amine | 455.6 |
| 17-13 | 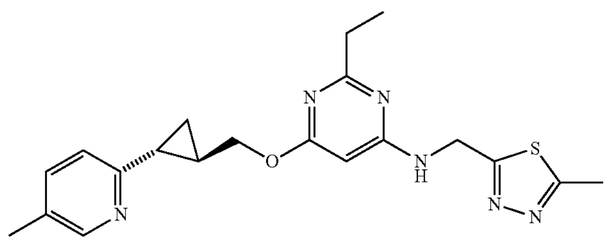 | 2-ethyl-N-((5-methyl-1,3,4-thiadiazol-2-yl)methyl)-6-(((1S,2S)-2-(5-methylpyridin-2-yl)cyclopropyl)methoxy)pyrimidin-4-amine | 397.1 |
| 17-14 | 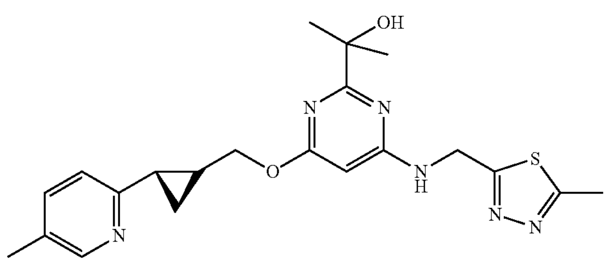 | 2-(4-((5-methyl-1,3,4-thiadiazol-2-yl)methylamino)-6-(((1R,2R)-2-(5-methylpyridin-2-yl)cyclopropyl)methoxy)pyrimidin-2-yl)propan-2-ol | 427.1 found, 427.1 required |
| 17-15 | 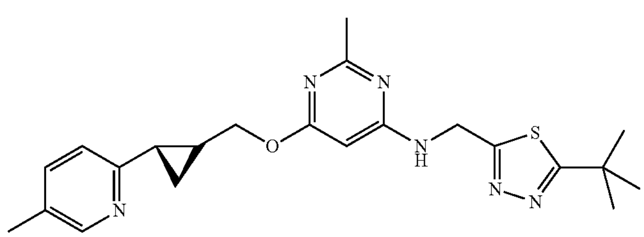 | N-((5-tert-butyl-1,3,4-thiadiazol-2-yl)methyl)-2-methyl-6-(((1S,2S)-2-(5-methylpyridin-2-yl)cyclopropyl)methoxy)pyrimidin-4-amine | 425.6 |
| 17-16 | 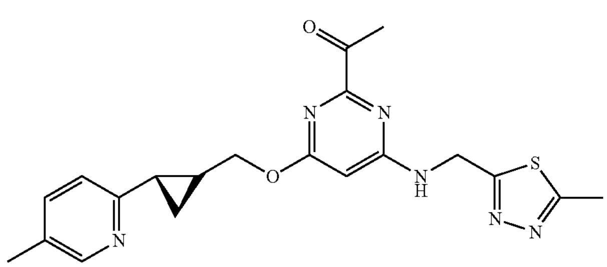 | 1-(4-((5-methyl-1,3,4-thiadiazol-2-yl)methylamino)-6-(((1R,2R)-2-(5-methylpyridin-2-yl)cyclopropyl)methoxy)pyrimidin-2-yl)ethanone | 411.2 found, 411.1 required |

TABLE 8-continued

The compounds in Table 8 were prepared in accordance with the example 17 below or an analogous manner to the examples of example 17, using the appropriate starting materials.

| Cpd. | Structure | Name | LRMS (M + H) |
|---|---|---|---|
| 17-18 | 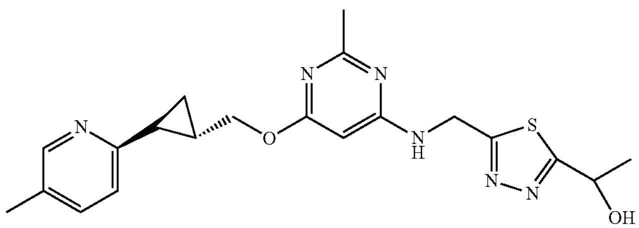 | 1-(5-((2-methyl-6-(((1S,2S)-2-(5-methylpyridin-2-yl)cyclopropyl)methoxy)pyrimidin-4-ylamino)methyl)-1,3,4-thiadiazol-2-yl)ethanol | 413.5 |
| 17-19 | 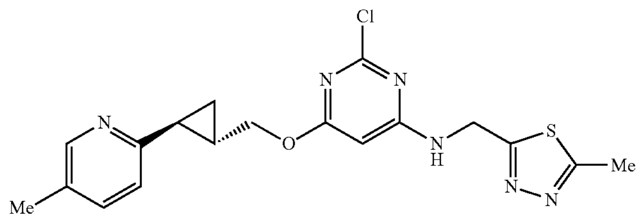 [SMILES: Cc1ccc([C@H]2C[C@@H]2COc2cc(NCc3nnc(C)s3)nc(Cl)n2)nc1] | 2-chloro-N-((5-methyl-1,3,4-thiadiazol-2-yl)methyl)-6-(((1S,2S)-2-(5-methylpyridin-2-yl)cyclopropyl)methoxy)pyrimidin-4-amine | 403.0 found, 403.1 required |

Starting materials not previously illustrated were commercially available, described in the literature, or readily synthesized by one skilled in the art of organic synthesis without undue experimentation.

The compounds of the following examples had activity in inhibiting the human PDE10 enzyme in the aforementioned assays with an Ki of about 0.001 nM to about 100 nM: 1-2, 2-3", 2 4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-21, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 3-4, 3-5, 3-6, 3-7, 3-8, 3-9, 3-10, 3-11, 3-12, 3-13, 3-14, 3-15, 3-16, 3-17, 3-18, 3-19, 3-10, 3-11, 3-12, 3-13, 3-14, 3-15, 3-16, 3-17, 3-18, 3-19, 3-20, 3-21, 3-"-22, 3-23, 3-24, 3-25, 3A-3, 4-1, 5-5, 6-4, 8-5, 8-3, 8-4, 8-5, 8-6, 8-7, 8-8, 8-9, 9-1, 9-2, 10-1, 11-1, 12-2, 12-3, 12-4, 12-5, 12-6, 13-1, 13-2, 14-3, 15-1, 16-4, 16-5, 16-6.

"The compounds of the following examples had activity in inhibiting the human PDE10 enzyme in the aforementioned assays with an Ki of about 0.001 nM to about 10 nM: 1-2, 2-3", 2-4, 2-6, 2-7, 2-8, 2-12, 2-14, 2-17, 2-27, 2-38, 2-54, 2-59, 3-8 , 3-11, 3-13, 3-14, 3-15, 3-19, 3-23, 3-25, 4-1, 5-5, 8-8, 9-1, 9-2, 12-2, 13-1, 14-3, 16-4."

The following table shows representative data for the compounds of the Examples as PDE10 inhibitors as determined by the foregoing assays wherein the PDE10 Ki is a measure of the ability of the test compound to inhibit the action of the PDE10 enzyme. Representative compounds of the invention had the Ki values specified in parentheses immediately following the compound number in the above-described assay.

| Compound | PDE10A Ki (nM) |
|---|---|
| 1-2 | 0.03 |
| 2-3" | 0.04 |
| 2-4 | 0.6 |
| 2-14 | 3.6 |
| 2-17 | 3.5 |
| 2-27 | 0.02 |
| 2-37 | 3.8 |
| 2-47 | 41.7 |
| 2-53 | 0.05 |
| 2-58 | 3.9 |

-continued

| Compound | PDE10A Ki (nM) |
|---|---|
| 3-8 | 1.1 |
| 3-11 | 1.6 |
| 3-13 | 0.5 |
| 3-19 | 3.6 |
| 3-25 | 0.09 |
| 8-8 | 1.0 |
| 9-2 | 0.08 |
| 12-2 | 1.1 |
| 14-3 | 5.3 |
| 16-4 | 1.6 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound selected from the group consisting of
2-Methyl-6-{2-(5-methylpyridin-2-yl)cyclopropyl]methoxy}-N-[(5-methyl-1,3,4-thiadiazol-2-yl)methyl]pyrimidin-4-amine,
2-Methyl-6-{[(1S,2S)-2-(5-methylpyridin-2-yl)cyclopropyl]methoxy}-N-[(5-methyl-1,3,4-thiadiazol-2-yl)methyl]pyrimidin-4-amine,
S,S-2-methyl-N-[(5-methyl-1,3,4-thiadiazol-2-yl)methyl]-6-{[2-(1,5-naphthyridin-2-yl)cyclopropyl]methoxy}pyrimidin-4-amine,
6-{[(1S,2 S)-2-(5-methoxypyridin-2-yl)cyclopropyl]methoxy}-N-4-[(5-methyl-1,3,4-thiadiazol-2-yl)methyl]pyrimidine-2,4-diamine,
5-fluoro-6-{[(1S,2S)-2-(5-methoxypyridin-2-yl)cyclopropyl]methoxy}-N-4-[(5-methyl-1,3,4-thiadiazol-2-yl)methyl]pyrimidine-2,4-diamine,
6-{[2-(3,3'-bipyridin-6-yl)cyclopropyl]methoxy}-2-methyl-N-[(5-methyl-1,3,4-thiadiazol-2-yl)methyl]pyrimidin-4-amine, 6-{[2-(5-cyclopropylpyridin-2-yl)cyclopropyl]methoxy}-2-methyl-N-[(5-methyl-1,3,4-thiadiazol-2-yl)methyl]pyrimidin-4-amine, and 2-amino-4-{[(1S,2S)-2-(5-methylpyridin-2-yl)cyclopropyl]methoxy}-6-{[(5-methyl-1,3,4-thiadiazol-2-yl)methyl]amino}pyrimidine-5-carbonitrile, or a pharmaceutically acceptable salt thereof.

2. A compound of structural formula:

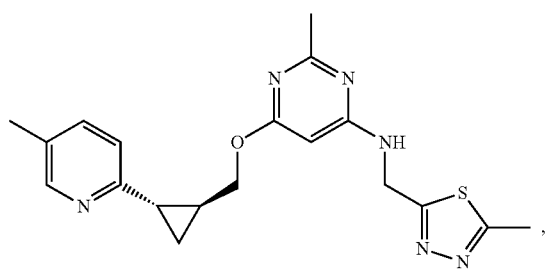

or a pharmaceutically acceptable salt thereof.

3. The compound according to claim 2 which is.

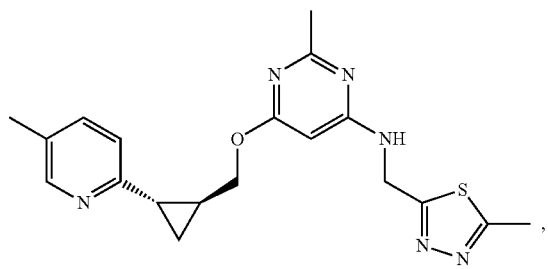

4. The compound according to claim 2 which is

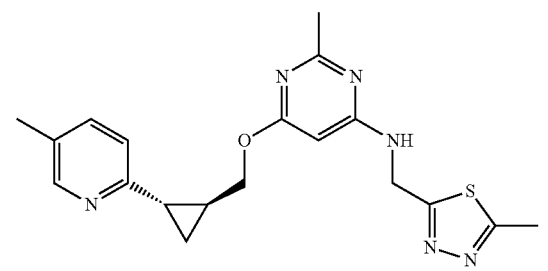

in the form of a pharmaceutically acceptable salt.

5. A compound which is

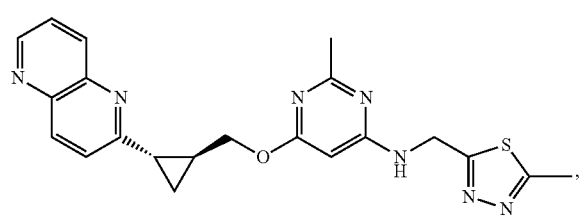 [SMILES: Cc1nc(NCc2nnc(C)s2)cc(OC[C@H]2C[C@@H]2c2ccc3ncccc3n2)n1]

or a pharmaceutically acceptable salt thereof.

6. The compound according to claim 5 which is

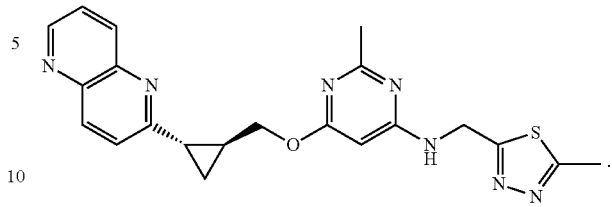

7. The compound according to claim 5 which is

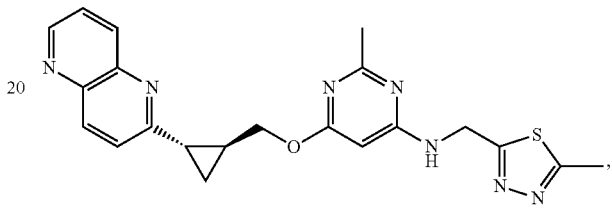

in the form of a pharmaceutically acceptable salt.

8. A compound which is

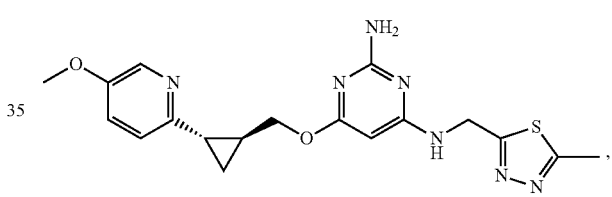

or a pharmaceutically acceptable salt thereof.

9. The compound according to claim 8 which is

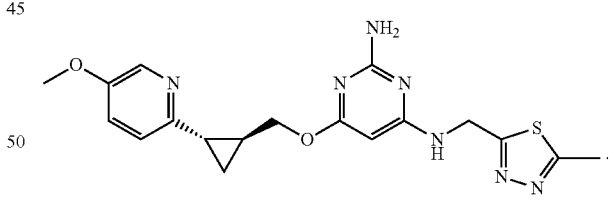

10. The compound according to claim 8 which is

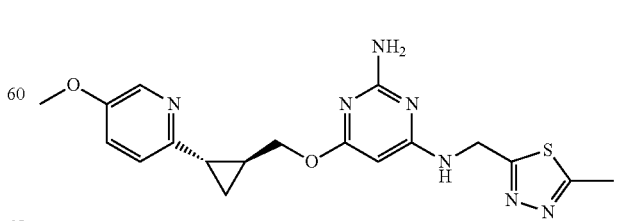

in the form of a pharmaceutically acceptable salt.

11. A compound which is

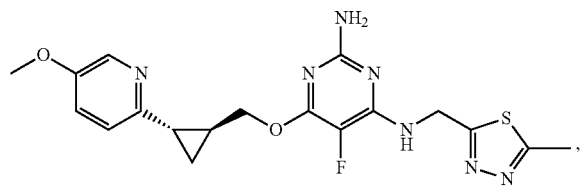

or a pharmaceutically acceptable salt thereof.
12. The compound according to claim 11 which is

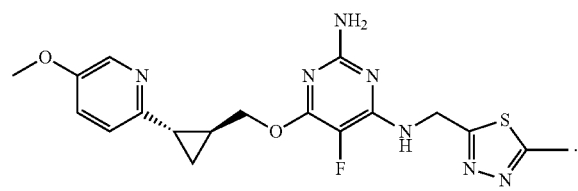

13. The compound according to claim 11 which is

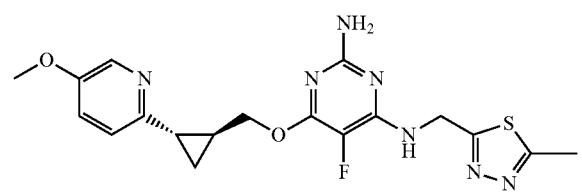

in the form of a pharmaceutically acceptable salt.
14. A compound which is

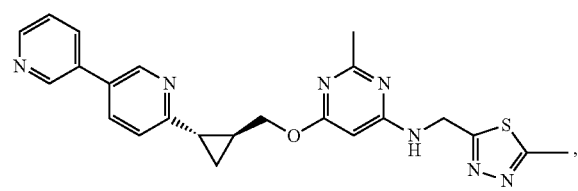 [SMILES: Cc1nc(NCc2nnc(C)s2)cc(OC[C@H]2C[C@@H]2c2ccc(-c3cccnc3)cn2)n1]

or a pharmaceutically acceptable salt thereof.
15. The compound according to claim 14 which is

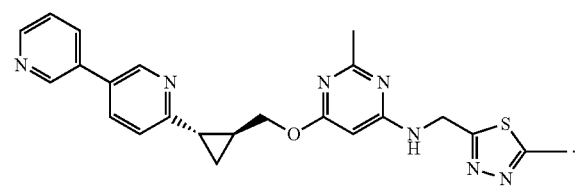 [SMILES: Cc1nc(NCc2nnc(C)s2)cc(OC[C@H]2C[C@@H]2c2ccc(-c3cccnc3)cn2)n1]

16. The compound according to claim 14 which is

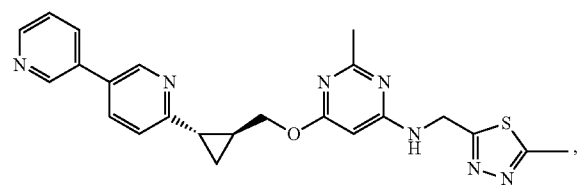 [SMILES: Cc1nc(NCc2nnc(C)s2)cc(OC[C@H]2C[C@@H]2c2ccc(-c3cccnc3)cn2)n1]

in the form of a pharmaceutically acceptable salt.

17. A compound which is

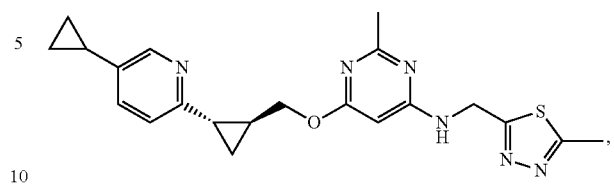

or a pharmaceutically acceptable salt thereof.
18. The compound according to claim 17 which is

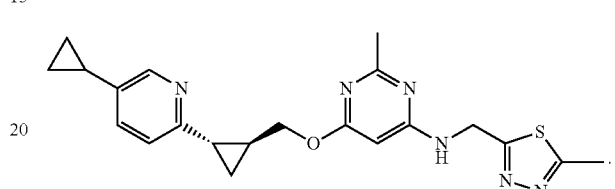

19. The compound according to claim 17 which is

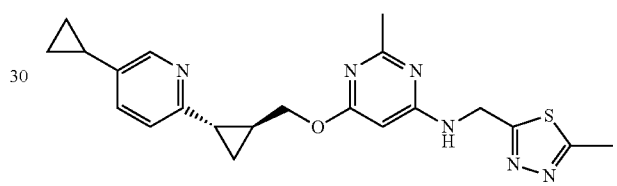

in the form of a pharmaceutically acceptable salt.
20. A compound which is

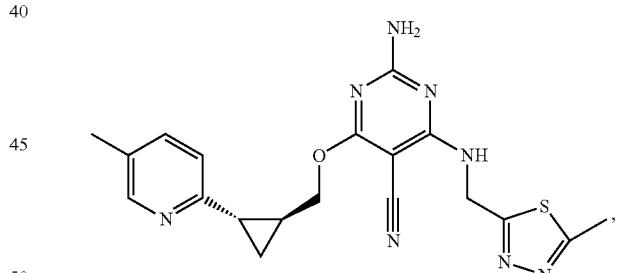

or a pharmaceutically acceptable salt thereof.
21. The compound according to claim 20 which is

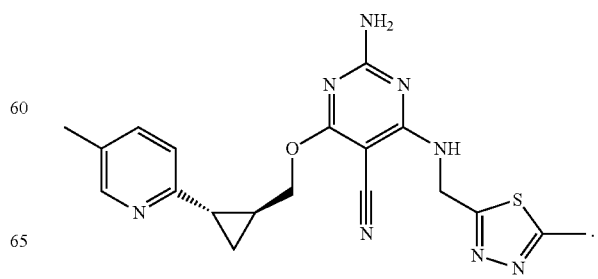

22. The compound according to claim 20 which is

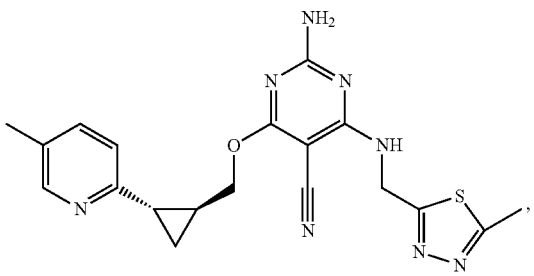

in the form of a pharmaceutically acceptable salt.

23. A pharmaceutical composition which comprises a pharmaceutically acceptable carrier and a compound of claim 1 or a pharmaceutically acceptable salt thereof.

24. A pharmaceutical composition which comprises a pharmaceutically acceptable carrier and the compound of claim 3.

25. A pharmaceutical composition which comprises a pharmaceutically acceptable carrier and the compound according to claim 4.

26. A pharmaceutical composition which comprises a pharmaceutically acceptable carrier and the compound of claim 6.

27. A pharmaceutical composition which comprises a pharmaceutically acceptable carrier and the compound according to claim 7.

28. A pharmaceutical composition which comprises a pharmaceutically acceptable carrier and the compound of claim 9.

29. A pharmaceutical composition which comprises a pharmaceutically acceptable carrier and the compound according to claim 10.

30. A pharmaceutical composition which comprises a pharmaceutically acceptable carrier and the compound of claim 12.

31. A pharmaceutical composition which comprises a pharmaceutically acceptable carrier and the compound according to claim 13.

32. A pharmaceutical composition which comprises a pharmaceutically acceptable carrier and the compound of claim 15.

33. A pharmaceutical composition which comprises a pharmaceutically acceptable carrier and the compound according to claim 16.

34. A pharmaceutical composition which comprises a pharmaceutically acceptable carrier and the compound of claim 18.

35. A pharmaceutical composition which comprises a pharmaceutically acceptable carrier and the compound according to claim 19.

36. A pharmaceutical composition which comprises a pharmaceutically acceptable carrier and the compound of 21.

37. A pharmaceutical composition which comprises a pharmaceutically acceptable carrier and the compound according to claim 22.

* * * * *